US008153583B2

(12) United States Patent
Carton et al.

(10) Patent No.: US 8,153,583 B2
(45) Date of Patent: Apr. 10, 2012

(54) TOLL LIKE RECEPTOR 3 ANTAGONISTS, METHODS AND USES

(76) Inventors: Jill M. Carton, Malvern, PA (US); Shizhong Chen, San Diego, CA (US); Mark Cunningham, Kennett Square, PA (US); Anuk Das, Wayne, PA (US); Karen Duffy, Trappe, PA (US); Jill M. Giles-Komar, Downingtown, PA (US); Theresa J. Goletz, King of Prussia, PA (US); David M. Knight, Berwyn, PA (US); Roberta Lamb, Wynnewood, PA (US); Mouhamadou L. Mbow, King of Prussia, PA (US); Kristen Picha, Malvern, PA (US); Gopalan Raghunathan, San Diego, CA (US); Lani San Mateo, Devon, PA (US); Robert T. Sarisky, Lansdale, PA (US); Vedrana Stojanovic-Susulic, Princeton Junction, NJ (US); Nicole Stowell, Havertown, PA (US); Raymond Sweet, Bryn Mawr, PA (US); Shanrong Zhao, San Diego, CA (US)

(*) Notice: Subject to any disclaimer, the term of this patent is extended or adjusted under 35 U.S.C. 154(b) by 549 days.

(21) Appl. No.: 11/291,140

(22) Filed: Nov. 30, 2005

(65) Prior Publication Data

US 2006/0115475 A1 Jun. 1, 2006

Related U.S. Application Data

(60) Provisional application No. 60/631,815, filed on Nov. 30, 2004, provisional application No. 60/639,399, filed on Dec. 15, 2004, provisional application No. 60/641,877, filed on Jan. 6, 2005, provisional application No. 60/713,195, filed on Aug. 31, 2005, provisional application No. 60/727,610, filed on Oct. 18, 2005.

(51) Int. Cl.
*A61K 38/00* (2006.01)
*C07K 16/00* (2006.01)
(52) U.S. Cl. ...... 514/1.4; 514/6.9; 514/12.2; 530/387.1; 530/387.3; 530/388.1; 530/388.15
(58) Field of Classification Search .................. None
See application file for complete search history.

(56) References Cited

U.S. PATENT DOCUMENTS

| 4,816,567 | A | 3/1989 | Cabilly et al. |
| 5,225,539 | A | 7/1993 | Winter et al. |
| 7,271,248 | B2* | 9/2007 | Hardiman et al. ......... 530/387.1 |
| 2005/0106142 | A1 | 5/2005 | Marshak-Rothstein et al. |
| 2005/0119273 | A1* | 6/2005 | Lipford et al. ............ 514/252.17 |

FOREIGN PATENT DOCUMENTS

| EP | 1495756 A1 | 1/2005 |
| WO | WO 98/50547 A2 | 11/1998 |
| WO | WO 00/53165 A2 | 9/2000 |
| WO | WO 00/53224 A2 | 9/2000 |
| WO | WO 01/47543 A2 | 7/2001 |
| WO | WO 03/031573 A2 | 4/2003 |
| WO | WO 03/106499 A1 | 12/2003 |

OTHER PUBLICATIONS

Kanzler et al. 2007, Nature Medicine, vol. 13, No. 5, pp. 552-559.*
Matsumoto, 2002, Biochemical and Biophysical Research Communications, vol. 293, pp. 1364-1369.*
Duffy, 2007, Cellular Immunology, vol. 248, pp. 103-114.*
Shizuo Akira, "Toll-like Receptors and Innate Immunity," Advances in Immunology, 78: 1-56 (2001).
Akira, et al., "Recognition of pathogen-associated molecular patterns by TLR family," Immunology Letters, 85: 85-95 (2003).
Murthy, et al., "Combination therapy of pentoxifylline and TNFα monoclonal antibody in dextran sulphate-induced mouse colitis," Ailment Pharmacology Therapy, 13: 251-260 (1999).
Kleinerman, et al., "Effect of Virus Infection on the Inflammatory Response," American Journal of Pathology, 85: 373-382 (1976).
Gern, et al., "Double-Stranded RNA Induces the Synthesis of Specific Chemokines by Bronchial Epithelial Cells," American Journal of Respiratory and Cell Molecular Biology, 28: 731-737 (2003).
Sha, et al, "Activation of Airway Epithelial Cells by Toll-Like Receptor Agonists," American Journal of Respiratory and Cell Molecular Biology, 31:358-364 (2004).
Parronchi, et al., "Type 1 T-Helper Cell Predominance and Interleukin-12 Expression in the Gut of Patients with Crohn's Disease," American Journal of Pathology, 150(3): 823-832 (1997).
Coultas, et al., "The Epidemiology of Interstitial Lung Diseases," American Journal of Respiratory and Critical Care Medicine, 150: 967-972 (1994).
Plotkowski, et al., "Adherence of Type 1 *Streptococcus pneumoniae* to Tracheal Epithelium of Mice Infected with Influenza A/PR8 Virus," American Review of Respiratory Disease, 134: 1040-1044 (1986).
Hancock, et al., "Production of Interleukin 13 by Alveolar Macrophages from Normal and Fibrotic Lung," American Journal of Respiratory and Cell Molecular Biology, 18: 60-65 (1998).
Belperio, et al., "Interaction of IL-13 and C10 in the Pathogenesis of Bleomycin-Induced Pulmonary Fibrosis," American Journal of Respiratory and Cell Molecular Biology, 27: 419-427 (2002).
Braegger, et al., "Immune mechanisms in chronic inflammatory bowel disease", Annals of Allergy, 72: 135-141 (1994).
Banchereau, et al., "Immunobiology of Dendritic Cells," Annual Review of Immunology, 18: 767-811 (2000).
Barton, et al., "Toll-Like Receptor Signaling Pathways," Science, 300: 1524-1525 (2003).
Ieki, et al., "Double-stranded RNA activates RANTES gene transcription through co-operation of nuclear factor κB and interferon regulatory factors in human airway epithelial cells," Clinical and Experimental Allergy, 34: 745-752 (2004).

(Continued)

*Primary Examiner* — Robert Landsman
*Assistant Examiner* — Ian Dang
(74) *Attorney, Agent, or Firm* — Kirk Baumeister

(57) ABSTRACT

Toll Like Receptor 3 (TLR3) antagonists, polynucleotides encoding TLR3 antagonists, and methods of making and using the foregoing are disclosed.

9 Claims, 48 Drawing Sheets

OTHER PUBLICATIONS

Keating, et al., "Infliximab: An Updated Review of its Use in Crohn's Disease and Rheumatoid Arthritis," BioDrugs, 16(2): 111-148 (2002).

Blair, et al., "Double-Stranded RNA-Dependent Protein Kinase Is Not Required for Double-Stranded RNA-Induced Nitrix Oxide Synthase Expression or Nuclear Factor-κB Activation by Islets," Diabetes, 50: 283-290 (2001).

F.Q.B Alenzi, "Links between apopotosis, proliferation and the cell cycle," British Journal of Biomedical Science, 61(2): 99-102 (2004).

Charles E. Samuel, "Antiviral Actions of Interferons," Clinical Microbiology Reviews, 14(4): 778-809 (2001).

Angus, et al., "Epidemiology of severe sepsis in the United States: Analysis of incidence, outcome, and associated costs of care," Critical Care Medicine, 29(7): 1303-1310 (2001).

Ayala, et al., "Mechanisms of immune resolution," Critical Care Medicine, 31: S558-S571 (2003).

Obermeier, et al., "Interferon-gamma (IFN-γ- and tumour necrosis factor (TNF)-induced nitric oxide as toxic effector molecule in chronic dextran sulphate sodium (DSS)-induced colitis in mice," Clinical and Experimental Immunology, 116: 238-245 (1999).

Dieleman, et al., "Chronic experimental colitis induced by dextran sulphate sodium (DSS) is characterized by Th1 and Th2 cytokines," Clinical and Experimental Immunology, 114: 385-391 (1998).

Kojouharoff, et al., "Neutralization of tumour necrosis factor (TNF) but not of IL-1 reduces inflammation in chronic dextran sulphate sodium-induced colitis in mice," Clinical and Experimental Immunology, 107: 353-358 (1997).

Hendrickson, et al., "Clinical Aspects and Pathophysiology of Inflammatory Bowel Disease," Clinical Microbiology Reviews, 15(1): 79-94 (2002).

Van Amersfoort, et al., "Receptors, Mediators, and Mechanisms Involved in Bacterial Sepsis and Septic Shock," Clinical Microbiology Reviews, 16(3): 379-414 (2003).

Luke AJ O'Neill, et al., "Therapeutic targeting of Toll-like receptors for inflammatory and infectious diseases," Current Opinion in Pharmacology, 3: 396-403 (2003).

Panina-Bordignon, et al., "Chemokines and their receptors in asthma and chronic obstructive pulmonary disease," Current Opinions in Pulmonary Medicine, 9: 104-110 (2003).

Pierre Miossec, "An update on the cytokine network in rheumatoid arthritis," Current Opinions in Rheumatology, 16: 218-222 (2004).

Donelan, et al., "The N- and C-Terminal Domains of the NS1 Protein of Influenza B Virus Can Independently Inhibit IRF-3 and Beta Interferon Promoter Activation," Journal of Virology, 78(21): 11574-11582 (2004).

Liu, et al., "Double-Stranded RNA Cooperates with Interferon-γ and IL-1β to Induce Both Chemokine Expression and Nuclear Factor-κB-Dependent Apoptosis in Pancreatic β-Cells: Potential Mechanisms for Viral-Induced Insulitis and β-Cell Death in Type 1 Diabetes Mellitus," Endocrinology, 143(4): 1225-1234 (2002).

Bausinger, et al., "Endotoxin-free heat-shock protein 70 fails to induce APC activation," European Journal of Immunology, 32: 3708-3713 (2002).

Köhler, et al., "Derivation of specific antibody-producing tissue culture and tumor lines by cell fusion," European Journal of Immunology, 6: 511-519 (1976).

Krug, et al., "Toll-like receptor expression reveals CpG DNA as a unique microbial stimulus for plasmacytoid dendritic cells which synergizes with CD40 ligand to induce high amounts of IL-12," European Journal of Immunology, 31: 3026-3037 (2001).

Jarrossay, et al., "Specialization and complementarity in microbial molecule recognition by human myeloid and plasmacytoid dencritic cells," European Journal of Immunology, 31: 3388-3393 (2001).

Bachar, et al., "Toll-like receptor stimulation induces airway hyperresponsiveness to bradykinin, an effect mediated by JNK and NF-κB signaling pathways," European Journal of Immunology, 34: 1196-1207 (2004).

Köhler, et al., "Fusion between immunoglobulin-secreting and nonsecreting myeloma cell lines," European Journal of Immunology, 6: 292-295 (1976).

Fuss, et al., "Disparate CD4+ Lamina Propria (LP) Lymphokine Secretion Profiles in Inflammatory Bowel Disease," The Journal of Immunology, 157: 1261-1270 (1996).

R. Balfour Sartor, "Current Concepts of the Etiology and Pathogenesis or Ulcerative Colitis and Crohn's Disease," Inflammatory Bowel Disease, 24(3): 475-507 (1995).

Okayasu, et al., "A Novel Method in the Induction of Reliable Experimental Acute and Chronic Ulcerative colitis in Mice," Gastroenterology, 98:694-702 (1990).

Guidotti, et al., "Noncytolytic Control of Viral Infections by the Innate and Adaptive Immune," Annual Review of Immunology, 19: 65-91 (2001).

Hanauer, et al., "The State of the Art in the Management of Inflammatory Bowel Disease," Review in Gastroenterological Disorders, 3(2): 81-92 (2003).

Harte, et al., "The Poxvirus Protein A52R Targets Toll-like Receptor Signaling Complexes to Suppress Host Defense," Journal of Experimental Medicine, 197(3): 343-351 (2003).

Hartmann, et al., "Mechanism and Function of a Newly Identified CpG DNA Motif in Human Primary B Cells," The Journal of Immunology, 164: 944-952 (2000).

Baumforth, et al., "Molecular and Immunological Aspects of Cell Proliferation," Molecular Biology in Cellular Pathology, John Wiley & Sons, Ltd., 105-135 (2003).

Heil, et al., Species-Specific Recognition of Single-Stranded RNA via Toll-like Receptor 7 and 8, Science, 303: 1526-1529 (2004).

Hendrix, et al., "Biologic Effects after a Single Dose of Poly(I):poly($C_{12}U$) in Healthy Volunteers," Antimicrobial Agents and Chemotherapy, 37(3): 429-435 (1993).

Hinshaw, et al., "Apoptosis: a Mechanism of Cell Killing by Influenza A and B Viruses," Journal of Virology, 68(6): 3667-3673 (1994).

Hogaboam, et al., "Differential Monocyte Chemoattractant Protein-1 and Chemokine Receptor 2 Expression by Murine Lung Fibroblasts Derived from Th1- and Th2-Type Pulmonary Granuloma Models," The Journal of Immunology, 163: 2193-2201 (1999).

Jakubzick, et al., "Therapeutic Targeting of IL-4- and IL-13-Responsive Cells in Pulmonary Fibrosis," Immunologic Research, 30(3): 339-349 (2004).

Medzhitov, et al., "Innate Immune Recognition: Mechanisms and Pathways," Immunological Reviews, 173: 89-97 (2000).

Horner, et al., "DNA-based immunotherapeutics for the Treatment of Allergic Disease," Immunological Reviews, 179: 102-118 (2001).

Andreakos, et al., "Is targeting Toll-like receptors and their signaling pathway a useful therapeutic approach to modulating cytokine-driven inflammation?" Immunological Reviews, 202: 250-265 (2004).

Aalberse, et al., "IgG4 breaking the rules," Immunology, 105: 9-19 (2002).

Shaun R. McColl, "Chemokines and dendritic cells: A crucial alliance," Immunology and Cell Biology, 80: 489-496 (2002).

Cario, et al., "Differential Alteration in Intestinal Epithelial Cell Expression of Toll-Like Receptor 3 (TLR3) and TLR4 in Inflammatory Bowel Disease," Infection and Immunity, 68(12): 7010-7017 (2000).

Deckert, et al., "Pharmacokinetics and Microdistribution of Polyethylene Glycol-Modified Humanized A33 Antibody Targeting Colon Cancer Xenografts," International Journal of Cancer, 87:382-390 (2000).

Giantonio, et al., "Toxicity and response evaluation of the interferon inducer poly ICLC administered at low dose in advanced renal carcinoma and relapsed or refractory lymphoma: A report of two clinical tirals of the Eastern Cooperative Oncology Group," Investigational New Drugs, 19: 89-92 (2001).

Daniel N. Sauder, et al., "Immunomodulatory and pharmacologic properties of imiquimod," Journal of American Academic Dermatology, 43: S6-S11 (2000).

Brent E. Wisse, "The Inflammatory Syndrome: The Role of Adipose Tissue Cytokines in Metabolic Disorders Linked to Obesity," Journal of American Society of Nephrology, 15: 2792-2800 (2004).

Tang, et al., "Herpesvirus DNA Is Consistently Detected in Lungs of Patients with Idiopathic Pulmonary Fibrosis," Journal of Clinical Microbiology, 41(6): 2633-2640 (2003).

Jakubzick, et al., "Augmented pulmonary IL-4 and IL-13 receptor subunit expression in idiopathic interstitial pneumonia," Journal of Clinical Pathology, 57: 477-486 (2004).

Krebs, et al., "High-throughput generation and engineering of recombinant human antibodies," Journal of Immunological Methods, 254: 67-84 (2001).

Glezen, et al., "Mortality and Influenza," The Journal of Infectious Diseases, 146(3): 313-321 (1982).

Scheiblauer, et al., "Interactions between Bacteria and Influenza A Virus in the Development in Influenza Pneumonia," The Journal of Infectious Diseases, 166: 783-791 (1992).

LeVine, et al., "Decreased pulmonary clearance of S. pneumoniae following influenza A infection in mice," Journal of Virological Methods, 94: 173-186 (2001).

Karikó, et al., "mRNA Is an Endogenous Ligand for Toll-like Receptor 3," The Journal of Biological Chemistry, 279(13): 12542-12550 (2004).

Zhou, et al., Human Blood Dendeitic Cells Selectively Express CD83, A Member of the Immunoglobulin Superfamily, 154: 3821-3835 (1995).

Tsan, et al., "Endogenous ligands of Toll-like receptors," Journal of Leukocyte Biology, 76: 514-519 (2004).

Wen, et al., "The Effect of Innate Immunity on Autoimmune Diabetes and the Expression of Toll-Like Receptors on Pancreatic Islets," The Journal of Immunology, 172: 3173-3180 (2004).

Jakubzick, et al., "Therapeutic Attenuation of Pulmonary Fibrosis Via Targeting of IL-4- and IL-13-Responsivle Cells," The Journal of Immunology, 171: 2684-2693 (2003).

Janeway, et al., "Innate Immune Recognition," Annual Review of Immunology, 20: 197-216 (2002).

Kabashima, et al., "The prostaglandin receptor EP4 suppresses colitis, mucosal damage and CD4 cell activation in the gut," Journal of Clinical Investigation, 109: 883-893 (2002).

Kadowaki, et al., "Subsets of Human Dendritic Cell Precursors Express Different Toll-like Receptors and Respond to Different Microbial Antigens," Journal of Experimental Medicine, 194 (6): 863-869 (2001).

Karin, et al., "The IKK NF-κB System: A Treasure Trove for Drug Development," Nature Reviews, 3: 17-26 (2004).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).

Kolodsick, et al., "Protection from Fluorescein Isothiocyanate-Induced Fibrosis in IL-13-Deficient, but Not IL-4-Deficient, Mice Results from Impaired Collagen Synthesis by Fibroblasts," The Journal of Immunology, 172: 4068-4076 (2004).

Arthur M. Krieg, "CpG Motifs in Bacterial DNA and their Immune Effects," Annual Review of Immunology, 20: 709-760 (2002).

Leong, et al., "Adapting Pharmacokinetic Properties of a Humanized Anti-Interleukin-8 Antibody for Therapeutic Applications Using Site-Specific Pegylation," Cytokine, 16(3): 106-119 (2001).

Medzhitov, et al., "A human homologue of the Drosophila Toll protein signals activation of adaptive immunity," Nature, 388: 394-397 (1997).

Mapel, et al., "The cost of Chronic Obstructive Pulmonary Disease and Its Effects on Managed Care," Managed Care Interface, p. 61-66 (2004).

Manns, et al., "Peginterferon alfa-2b plus ribavirin compared with interferon alfa-2b plus ribavirin for initial treatment of chronic hepatitis C: a randomised trial," The Lancet, 358: 958-965 (2001).

Matsumoto, et al.,, "Establishment of a monoclonal antibody against human Toll-like receptor 3 that blocks double-stranded RNA-mediated signaling," Biochemical and Biophysical Research Communications, 293: 1364-1369 (2002).

McCullers, et al. "Lethal Synergism between Influenza Virus and Stroptococcus pneumoniae: Characterization of a Mouse Model and the Role of Platelet-Activating Factor Receptor," The Journal of Infectious Diseases, 186: 341-350 (2002).

Monteleone, et al., "Interleukin 12 is Expressed and Actively Released by Crohn's Disease Intestinal Lamina Propria Mononuclear Cells," Gastroenterology, 112: 1169-1178 (1997).

Bouma, et al., "The Immunological and Genetic Basis of Inflammatory Bowel Disease," Nature Reviews, 3: 521-533 (2003).

Lonberg, et al., "Antigen-specific human antibodies from mice comprising four distinct genetic modifications," Nature, 368: 856-859 (1994).

Köhler, et al., "Continuous cultures of fused cells secreting antibody of predefined specificity," Nature, 256: 495-497 (1975).

Banchereau, et al., "Dendritic cells and the control of immunity," Nature, 392: 245-252 (1998).

Alexopoulou, et al., "Recognition of double-stranded RNA and activation of NF-κB by Toll-like receptor 3," Nature, 413: 732-738 (2001).

Fishwild, et al., "High-avidity human IgGκ monoclonal antibodies from a novel strain of minilocus transgenic mice," Nature Biotechnology, 14: 845-851 (1996).

Mendez, et al., "Functional transplant of megabase human immunoglobulin loci recapitulates human antibody response in mice," Nature Genetics, 15: 146-156 (1997).

Douglas T. Fearon, "Seeking wisdom in innate immunity," Nature, 388: 323-324 (1997).

Gross, et al., Idiopathic Pulmonary Fibrosis, New England Journal of Medicine, 345 (7): 517-525 (2001).

Pasare, et al., "Toll-like receptors: linking innate and adaptive immunity," Microbes and Infection 6: 1382-1387 (2004).

Gerald B. Pier, "Role of the cystic fibrosis transmembrane conductance regulator in innate immunity to Pseudomonas aeruginosa infections," Proceedings of the National Academy of Science USA, 97: 8822-8828 (2000).

Knight, et al., "Pharmacodynamic enhancement of the anti-platelet antibody Fab abciximab by site-specific pegylation," Platelets, 15 (7): 409-418 (2004).

Yang, et al., "Tailoring structure-function and pharmacokinetic properties of single-chain Fv proteins by site-specific PEGylation," Protein Engineering, 16 (10): 761-770 (2003).

Queen, et al., "A Humanized Antibody that Binds to the Interleukin 2 Receptor," Proceedings of the National Academy of Sciences USA, 86: 10029-10033 (1989).

Rachmilewitz, et al., "Immunostimulatory DNA Ameliorates Experimental and Spontaneous Murine Colitis," Gastroenterology, 122: 1428-1441 (2002).

Rakoff-Nahoum, et al., "Recognition of Commensal Microflora by Toll-Like Receptors is Required for Intestinal Homeostasis," Cell, 118: 229-241 (2004).

Rincón, et al., "Interleukin (IL)-6 Directs the Differentiation of IL-4 Producing CD4+ T Cells," Journal of Experimental Medicine, 185 (3): 461-469 (1997).

Sabroe, et al., "Toll-Like Receptors in Health and Disease: Complex Questions Remain," The Journal of Immunology, 15 (171): 1630-1635 (2003).

Schetter, et al., "Toll-like receptors involved in the response to microbial pathogens: Development of agonists for toll-like receptor 9," Current Opinion in Drug Discovery & Development, 7 (2): 204-210 (2004).

Siegal, et al., "The Nature of the Principal Type 1 Interferon-Producing Cells in Human Blood," Science, 284: 1835-1837 (1999).

Staats, et al., "IL-1 Is an Effective Adjuvant for Mucosal and Systemic Immune Responses When Coadministered with Protein Immunogens," The Journal of Immunology, 162: 6141-6147 (1999).

Stark, et al., "How Cells Respond to Interferons," Annual Review of Biochemistry, 67: 227-264 (1998).

Lothar Steidler, "Microbiological and immunological strategies for treatment for inflammatory bowel disease," Microbes and Infection, 3: 1157-1166 (2001).

Stewart, et al., "The Detection of Epstein-Barr Virus DNA in Lung Tissue from Patients with Idiopathic Pulmonary Fibrosis," American Journal of Respiratory and Critical Care Medicine, 159: 1336-1341 (1999).

Sun, et al., "Negative Regulation of Liver Regeneration by Innate Immunity (Natural Killer Cells/Interferon-γ)," Gastroenterology, 127 1525-1539 (2004).

Tabeta, et al., "Toll-like receptors 9 and 3 as essential components of innate immune defense against mouse cytomegalovirus infection," Proceedings of the National Academy of Science USA, 101: 3516-3521 (2004).

Takeda, et al., "Microbial recognition by Toll-like receptors," Journal of Dermatological Science, 34: 73-82 (2004).

Wong, et al., "Prophylactic and Therapeutic Efficacies of Poly(IC—LC) against Respiratory Influenza A Virus Infection in Mice," Antimicrobial Agents and Chemotherapy, 39 (11): 2574-2576 (1995).

Zarember, et al., "Tissue Expression of Human Toll-Like Receptors and Differential Regulation of Toll-Like Receptor mRNAs in Leukocytes in Resonse to Microbes, Their Products, and Cytokines," The Journal of Immunology, 168: 554-561 (2002).

Zhou, et al., "CD14+ blood monocytes can differentiate into functionally mature CD83+ dendritic cells," Proceedings of the National Academy of Science USA, 93: 2588-2592 (1996).

O''Neill, et al., "The Toll-IL-1 receptor adaptor family grows to five members," Trends in Immunology, 24 (6): 286-289 (2003).

Hampe, et al., "A Genomewide Analysis Provides Evidence for Novel Linkages in Inflammatory Bowel Disease in a Large European Cohort," American Journal of Human Genetics, 64: 808-816 (1999).

Hodgson, et al., "Making Monoclonals in Microbes," Bio/Technology, 9: 421-421 (1991).

Bandi, et al., "Infectious exacerbations of chronic obstructive pulmonary disease associated with respiratory viruses and non-typeable *Haemophilus influenzae*," FEMS Immunology and Medical Microbiology, 37: 69-75 (2003).

Hament, et al., "Respiratory viral infection predisposing for bacterial disease: a concise review," FEMS Immunology and Medical Microbiology, 26: 189-195 (1999).

Tuomanen, et al., "The Biology of Pneumoccal Infection," Pediatric Research, 42(3): 253-258 (1997).

Natanson, et al., "The sirens' song of confirmatory sepsis trials: Selection bias and sampling error," Critical Care Medicine, 26(12): 1927-1931 (1998).

GenBank Accession No. HSU88879, Sep. 3, 1998.

Kabat, et al., Sequences of Proteins of Immunological Interest, U.S. Department of Health, vii-xix (1987).

Lok, et al., "Viruses and idiopathic pulmonary fibrosis," Monaldi Archives for Chest Disease, 55(2): 146-150 (2000).

Joshua A. Boyce, "The role of mast cells in asthma," Prostaglandins Leukotrienes and Essential Fatty Acids, 69: 195-205 (2003).

Ogata, et al., "Cytokine and Anti-cytokine Therapies for Inflammatory Bowel Disease," Current Pharmaceutical Design, 9: 1107-1113 (2003).

Sebastian L. Johnston, "Natural and Experimental Rhinovirus Infections of the Lower Respiratory Tract," American Journal of Respiratory and Critical Care Medicine, 152: 546-552 (1995).

"Death and death rates for the 10 leading causes of death in specified age groups, by race and sex: United States, 1997," National Vital Statistics Reports, 47(19): 27-37 (1999).

Duffy, et al., "Down modulation of human TLR3 function by a monoclonal antibody," Cellular Immunology, 248: 103-114 (2007).

Supplementary European Search Report dated Oct. 19, 2009.

Robert G. Hamilton, "Molecular Engineering: Applications to the Clinical Laboratory," Clinical Chemistry, 39(9): 1988-1997 (1993).

Matsushima, et al., "TLR3-, TLR7-, and TLR9-Mediated Production of Proinflammatory Cytokines and Chemokines from Murine Connective Tissue Type Skin-Derived Mast Cells but Not from Bone Marrow-Derived mast Cells," The Journal of Immunology, 173(1): 531-541 (2004).

Francesco M. Veronese, "Peptide and protein PEGylation: a review of problems and solutions," Biomaterials, 22(5): 405-417 (2001).

Winter, et al., "Humanized antibodies," Immunology Today, 14(6): 243-246 (1993).

* cited by examiner

Figure 1

Nucleotide sequence for 1068 heavy chain variable region
ATGGGATGGAGCTATATCATCCTCTTTTTGGTAGCAACAGCTACAGATGTCCACTCCCAGGTCCA
ACTGCAGCAGCCTGGGGCTGAACTGGTGCAGCCTGGGACTTCAGTGAGGCTGTCCTGCAAGGCTT
CTGGCTACATCTTCACCACCTACTGGATTCACTGGGTGAAACAGAGGCCTGGACAGGGCCTTGAG
TGGATTGGAGAGATTAACCCTAACAACGGTCGTATTAACTACAATGAGAAATTCAAGACCAAGGC
CACACTGACTGTAGACAAATCCTCCAGCACAGCCTACATGCAACTCAGCAGCCTGACATCTGAGG
ACTCTGCGGTCTATTACTGTACAAGAGTAGGGGTTATGATTACGACGTTTCCTTACTGGGGCCAA
GGGACTCTGGTCACTGTCTCTGCA (SEQ ID NO: 5)

Amino Acid sequence for 1068 heavy chain variable region
MGWSYIILFLVATATDVHSQVQLQQPGAELVQPGTSVRLSCKASGYIF<u>TTYWIH</u>WVKQRPGQGLE
WIG<u>EINPNNGRINYNEKFKT</u>KATLTVDKSSSTAYMQLSSLTSEDSAVYYCTR<u>VGVMITTFPY</u>WGQ
GTLVTVSA (SEQ ID NO: 6)

Signal Sequence
MGWSYIILFLVATATDVHS (SEQ ID NO: 7)

FR1
QVQLQQPGAELVQPGTSVRLSCKASGYIF (SEQ ID NO: 8)

CDR1
TTYWIH (SEQ ID NO: 9)

FR2
WVKQRPGQGLEWIG (SEQ ID NO: 10)

CDR2
EINPNNGRINYNEKFKT (SEQ ID NO: 11)

FR3
KATLTVDKSSSTAYMQLSSLTSEDSAVYYCTR (SEQ ID NO: 12)

CDR3
VGVMITTFPY (SEQ ID NO: 13)

FR4
WGQGTLVTVSA (SEQ ID NO: 14)

Figure 2

Nucleotide sequence for 1068 light chain variable region
ATGAGTGTGCTCACTCAGGTCCTGGCGTTGCTGCTGCTGTGGCTTACAGGTGCCAGATGTGACAT
CCAGATGACTCAGTCTCCAGCCTCCCTATCTGCATCTGTGGGAGAAACTGTCACCATCACATGTC
GAGCAAGTGGGAATATTCACAATTATTTAGCATGGTATCAGCAGAAACAGGGAAAATCTCCTCAG
CTCCTGGTCTATAATGCAAAAACCTTAGCAGATGGTGTGCCATCAAGATTCAGTGGCAGTGAATC
AGGAACACAATATTCTCTCAAGATCAACAGCCTGCAGCCTGAAGATTTTGGGAGTTATTACTGTC
AACATTTTTGGAGTACTCCATTTACGTTCGGCTCGGGGACAAAGTTGGAACTAAAA (SEQ ID
NO: 15)

Amino Acid sequence for 1068 light chain variable region
MSVLTQVLALLLLWLTGARCDIQMTQSPASLSASVGETVTITC<u>RASGNIHNYLA</u>WYQQKQGKSPQ
LLVY<u>NAKTLAD</u>GVPSRFSGSESGTQYSLKINSLQPEDFGSYYC<u>QHFWSTP</u>FTFGSGTKLELK
(SEQ ID NO: 16)

Signal sequence
MSVLTQVLALLLLWLTGARC (SEQ ID NO: 17)

FR1
DIQMTQSPASLSASVGETVTITC (SEQ ID NO: 18)

CDR1
RASGNIHNYLA (SEQ ID NO: 19)

FR2
WYQQKQGKSPQLLVY (SEQ ID NO: 20)

CDR2
NAKTLAD (SEQ ID NO: 21)

FR3
GVPSRFSGSESGTQYSLKINSLQPEDFGSYYC (SEQ ID NO: 22)

CDR3
QHFWSTP (SEQ ID NO: 23)

FR4
FTFGSGTKLELK (SEQ ID NO: 24)

TOLL LIKE RECEPTOR 3 ANTAGONISTS, METHODS AND USES

CROSS REFERENCE TO RELATED APPLICATIONS

This application claims the benefit of U.S. Provisional Application No. 60/631,815, filed 30 Nov. 2004 and U.S. Provisional Application No. 60/636,399, filed 15 Dec. 2004 and U.S. Provisional Application No. 60/641,877, filed 6 Jan. 2005 and U.S. Provisional Application No. 60/713,195, filed 31 Aug. 2005 and U.S. Provisional Application No. 60/727,610, filed 18 Oct. 2005, the entire contents of which are incorporated herein by reference.

FIELD OF THE INVENTION

The present invention relates to Toll Like Receptor 3 (TLR3) antagonists, polynucleotides encoding TLR3 antagonists or fragments thereof, and methods of making and using the foregoing.

BACKGROUND OF THE INVENTION

Pathologies associated with inflammatory conditions represent a significant challenge in health care and can be painful, debilitating and lethal. For example, sepsis and sepsis-associated conditions affect more than 750,000 people annually in the U.S. with mortality rates of 28-50%, resulting in 215,000 annual deaths (Natanson et al., *Crit. Care Med.* 26:1927-1931 (1998); Angus et al., *Crit. Care Med.* 29:1303-1310 (2001)). Other inflammatory conditions such as the inflammatory bowel diseases (IBD) Crohn's disease and ulcerative colitis affect more than 1 million people per year in the U.S. (Hanauer et al., *Rev. Gastroenterol. Disord.* 3:81-92 (2003)).

Inflammatory pulmonary conditions affecting lung function such as chronic obstructive pulmonary disease (COPD), asthma and lung infections also affect significant numbers of people in the U.S. COPD, for example, affects an estimated 10 million adult Americans and the prevalence is rising (Mapel et al., *Manag. Care Interface* 17:61-66 (2004)). Pathologies associated with these inflammatory conditions and exacerbations of these conditions have significant health and economic impacts.

Exacerbation in pulmonary diseases such as asthma and COPD is characterized by the worsening of symptoms and a decline in lung function. Viral infections are associated with exacerbations of many pulmonary diseases (Johnston, *Am. J. Respir. Crit. Care Med.* 152: S46-52 (1995); Bandi et al, *FEMS Immunol. Med. Microbiol.* 37: 69-75 (2003)) and are believed to be a major cause of exacerbations. Secretion of pro-inflammatory cytokines in the lungs following viral infection represents a crucial step in promoting the inflammatory response in various lung diseases (Gern et al., *Am. J. Respir. Cell. Mol. Biol.* 28:731-737 (2003); Panina-Bordignon et al., *Curr. Opin. Pulm. Med.* 9:104-110 (2003)).

Insulin resistance has been recognized as an integral feature of metabolic syndrome, which includes glucose intolerance, insulin resistance, obesity, hypertriglyceridemia, low HDL cholesterol, hypertension, and accelerated atherosclerosis (Wisse, *J. Am. Soc. Nephrol.* 15:2792-800 (2004)). While the predisposition between obesity, Type 2 diabetes and insulin resistance is well established, the molecular and cellular mechanisms controlling obesity-associated insulin resistance and Type 2 diabetes still remain nebulous.

The fact that obese individuals exhibit elevated levels of pro-inflammatory cytokines such as TNF-α, IL-1b and IL-6 has prompted the hypothesis that obesity-induced insulin resistance is an inflammatory condition (Karin et al., *Nat. Rev. Drug Discov.* 3:17-26 (2004)). Thus, inflammation, obesity, insulin resistance and aberrant lipid metabolism may constitute common features of the metabolic syndrome. In fact, non-steroidal drugs such as cyclooxygenase inhibitors, which may interfere with key inflammatory transcription factors such as NF-kβ and IKKβ, increase insulin sensitivity in Type 2 diabetes animal models and human patients (Karin et al., supra). Furthermore, recent data lend support to the link between insulin-resistance and inflammation, as shown by the ability of IKKb conditional knock-out mice in myeloid cells to display global insulin sensitivity and become protected against insulin resistance as well as mice that overexpress IKKb in liver develop systemic insulin resistance (Arkan et al., *Nat. Med.* 11:191-198 (2005); Cai et al., *Nat. Med.* 11:183-90 (2005)). Altogether, these results provide a strong rationale for linking obesity, insulin resistance and Type 2 diabetes to inflammatory diseases.

Recognition of microbial antigens by the host immune system is mediated through innate immune receptors, whose activation represents an important step in the initiation of an inflammatory response. Toll-Like Receptors (TLR) represent a family of innate immune receptors that play a crucial role in mediating an immune response to foreign antigens. TLR3, for example, is a mammalian pattern recognition receptor that recognizes double-stranded (ds) RNA as well as the synthetic ds RNA analog poly-riboinosinic-ribocytidylic acid (poly(I:C)), (Alexopoulou et al., *Nature* 413: 732-238 (2001)). Moreover, TLR3 has been shown to recognize endogenous ligands such as mRNA released from necrotic cells (Kariko et al., *J. Biol. Chem.* 26: 12542-12550 (2004)) suggesting that necrotic cell death at inflammation sites may contribute to activation of TLR3.

Activation of TLR3 by poly(I:C) or by endogenous mRNA ligands induces secretion of pro-inflammatory cytokines and chemokines, a finding that suggests that TLR3 agonists modulate disease outcome during infection-associated inflammation. Thus, TLR3 ligation in vivo is thought to occur in the context of viral infection (Tabeta et al., *Proc. Natl. Acad. Sci. USA* 101:3516-3521 (2004)) or necrosis associated with inflammation (Kariko et al., *J. Biol. Chem.* 26: 12542-12550 (2004)). Overall, these data demonstrate that ligation of TLR3 initiates cascades of phosphorylation and transcriptional activation events that result in the production of numerous inflammatory cytokines that are thought to contribute to innate immunity (reviewed by Takeda and Akira, *J. Derm. Sci.* 34:73-82 (2004)). Further, these data suggest that sustained TLR3 activation can be a critical component in the modulation of infection-associated inflammatory diseases. Published data lend support to this hypothesis as shown by findings that associate over-production of pro-inflammatory cytokines to systemic inflammatory response syndrome, infection-associated acute cytokine storms (reviewed by Van Amersfoort et al., *Clin. Microbiol. Rev.* 16: 379-414 (2003)) and immune-mediated chronic conditions such as rheumatoid arthritis (reviewed by Miossec et al., *Curr. Opin. Rheumatol.* 16:218-222 (2004)) and inflammatory bowel diseases (reviewed by Ogata and Hibi, *Curr. Pharm. Des.* 9: 1107-1113 (2003)).

Although in vitro studies have demonstrated that stimulation of lung epithelial cells with poly(I:C) elicited the secretion of multiple cytokines, chemokines and the induction of transcription factors and increased expression of TLRs (Ieki et al., *Clin. Exp. Allergy* 34: 745-52 (2004); Sha et al., *Am. J.*

Respir. Cell. Mol. Biol. 31: 358-64 (2004)), the physiological relevance of such events remain unclear.

These pathologies associated with inflammatory conditions and others, such as those associated with infections, have significant health and economic impacts. Yet, despite advances in many areas of medicine, comparatively few treatment options and therapies are available for many of these conditions.

For example, pulmonary disease exacerbations are treated with high dose corticosteroids and anti-IgE, such as XOLAIR® brand of omalizumab. Inhaled corticosteroids in combination with β2 agonists have been shown to be effective in reducing the incidence of exacerbations. However, since these therapeutics only reduce the risk of developing exacerbations and are associated with significant side effects, alternative therapeutic modalities for the prevention and treatment of pulmonary disease exacerbations are needed.

Thus, a need exists to understand the role of TLR3 in inflammatory conditions and exploit this role to develop agents, such as antagonists, that effectively treat those conditions.

BRIEF DESCRIPTION OF THE DRAWINGS

FIG. 1 shows heavy chain variable region sequences from an anti-human TLR3 (hTLR3) monoclonal antibody antagonist (CDRs are underlined).

FIG. 2 shows light chain variable region sequences from an anti-hTLR3 monoclonal antibody antagonist (CDRs are underlined).

SUMMARY OF THE INVENTION

Figure 3:
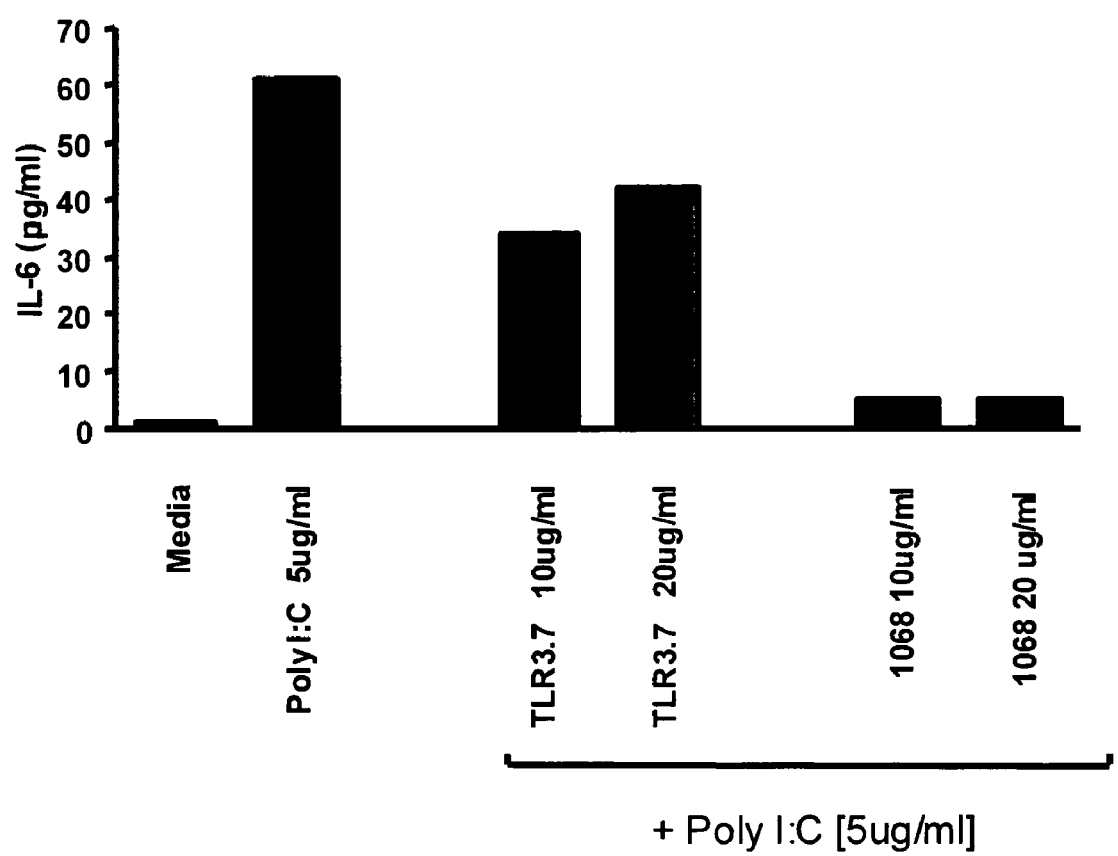
FIG. 3 shows inhibition of poly(I:C) induced IL-6 cytokine production in human lung epithelium derived cells by a TLR3 antagonist.

One aspect of the invention is an antagonist of Toll Like Receptor 3 (TLR3) that inhibits cellular production of RANTES.

Another aspect of the invention is an isolated antibody reactive with TLR3 having the antigen binding ability of a monoclonal antibody comprising the amino acid sequences of the heavy chain complementarity determining regions (CDRs) as shown in SEQ ID NOs: 9, 11 and 13 and the amino acid sequences of the light chain CDRs as shown in SEQ ID NOs: 19, 21 and 23.

Another aspect of the invention is an isolated antibody reactive with TLR3 comprising the amino acid sequences of the heavy chain complementarity determining regions (CDRs) as shown in SEQ ID NOs: 9, 11 and 13 and the amino acid sequences of the light chain CDRs as shown in SEQ ID NOs: 19, 21 and 23.

Another aspect of the invention is an isolated antibody having a $V_H$ CDR1 amino acid sequence as shown in Formula (I):

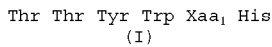
(I)

wherein $Xaa_1$ is Ile or Met (SEQ ID NO: 61);
a $V_H$ CDR2 amino acid sequence as shown in Formula (II):

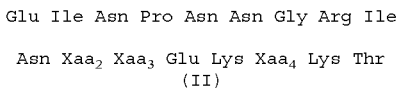
(II)

wherein $Xaa_2$ is Tyr or Gly, $Xaa_3$ is Asn or Ala and $Xaa_4$ is Phe or Gly (SEQ ID NO: 62); and
a $V_H$ CDR3 amino acid sequence as shown in Formula (III):

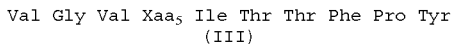
(III)

wherein $Xaa_5$ is Met or Ile (SEQ ID NO: 63);
and $V_L$ CDRs having the amino acid sequences shown in SEQ ID NOs: 19, 21 and 23.

Another aspect of the invention is an isolated polynucleotide encoding an antibody heavy chain comprising the CDR amino acid sequences shown in SEQ ID NOs: 9, 11 and 13.

Another aspect of the invention is an isolated polynucleotide encoding an antibody light chain comprising the CDR amino acid sequences shown in SEQ ID NOs: 19, 21 and 23.

Another aspect of the invention is an isolated polynucleotide encoding an antibody heavy chain comprising the amino acid sequence shown in SEQ ID NO: 6, 25, 27, 29, 31, 45, 47, 49, 51 or 53.

Another aspect of the invention is an isolated polynucleotide encoding an antibody light chain comprising the amino acid sequence shown in SEQ ID NO: 16, 33, 35, 37 or 39.

Another aspect of the invention is a method of treating or preventing an inflammatory condition comprising administering a therapeutically effective amount of a TLR3 antagonist to a patient in need thereof for a time sufficient to treat or prevent the inflammatory condition.

Another aspect of the invention is a method of increasing the proliferation rate of a cell comprising contacting a TLR3 antagonist with a cell that expresses a TLR3 receptor for a time sufficient to increase the proliferation rate of the cell.

DETAILED DESCRIPTION OF THE INVENTION

All publications, including but not limited to patents and patent applications, cited in this specification are herein incorporated by reference as though fully set forth.

The term "antagonist" as used herein means a molecule that partially or completely inhibits, by any mechanism, an effect of another molecule such as a receptor. As used herein, a "TLR3 antagonist" or a compound "reactive with TLR3" describes a molecule that is capable of, directly or indirectly, substantially counteracting, reducing or inhibiting TLR3 biological activity or TLR3 receptor activation. Such antagonists may be, for example, small organic molecules, peptides, polypeptides, fusion proteins, antibodies, antibody fragments, mimetibodies or polynucleotides.

The term "antibodies" as used herein is meant in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragments" means a portion of an intact antibody, generally the antigen binding or variable region of the intact antibody. Examples of antibody fragments include Fab, Fab', F(ab')$_2$ and Fv fragments, diabodies, single chain antibody molecules and multispecific antibodies formed from at least two intact antibodies.

The term "antigen" as used herein means any molecule that has the ability to generate antibodies either directly or indirectly (alternatively called an immunogen). Included within the definition of "antigen" is a protein-encoding nucleic acid.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to an antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The term "epithelial cell" as used herein means a cell that originates from a membranous cellular tissue covering a portion of a free surface (e.g., skin) or lining a tube or cavity (e.g., colon) of an animal. Such cells may be isolated or comprise part a more highly organized group of cells such as those found in tissues, organs or in vitro models of these.

The term "homolog" means protein sequences having between 40% and 100% sequence identity to a reference sequence. Homologs of hTLR3 include polypeptides from other species that have between 40% and 100% sequence identity to a known hTLR3 sequence. Percent identity between two peptide chains can be determined by pair wise alignment using the default settings of the AlignX module of Vector NTI v.9.0.0 (Invitrogen Corp., Carlsbad, Calif.). By "TLR3" is meant hTLR3 and its homologs. A full-length human TLR3 amino acid sequence and encoding polynucleotide sequence is shown in SEQ ID NOs: 1 and 2, respectively.

The term "in combination with" as used herein means that the described agents can be administered to an animal together in a mixture, concurrently as single agents or sequentially as single agents in any order.

The term "inflammatory condition" as used herein means a localized response to cellular injury that is mediated in part by the activity of cytokines, chemokines, or inflammatory cells (e.g., neutrophils, monocytes and lymphocytes) which is characterized in most instances by pain, redness, swelling and loss of tissue function. The term "inflammatory pulmonary condition" as used herein means an inflammatory condition affecting or associated with the lungs.

The term "mimetibody" as used herein means a protein having the generic formula (I):

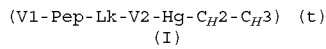

$$(V1\text{-}Pep\text{-}Lk\text{-}V2\text{-}Hg\text{-}C_H2\text{-}C_H3)\ (t) \quad (I)$$

where V1 is a portion of an N-terminus of an immunoglobulin variable region, Pep is a polypeptide that binds to cell surface TLR3, Lk is a polypeptide or chemical linkage, V2 is a portion of a C-terminus of an immunoglobulin variable region, Hg is a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10. A mimetibody can mimic properties and functions of different types of immunoglobulin molecules such as IgG1, IgG2, IgG3, IgG4, IgA, IgM, IgD and IgE dependent on the heavy chain constant domain amino acid sequence present in the construct. In some mimetibody embodiments, V1 may be absent. A mimetibody antagonist of the present invention affects TLR3 biological activity through binding to cell surface TLR3.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., *Nature* 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Human-adapted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Optionally, human-adapted mAbs can be further modified by incorporating altered framework support residues to preserve binding affinity by techniques such as those disclosed in Queen et al., *Proc. Natl. Acad. Sci.* (*USA*), 86:10029-10032 (1989) and Hodgson et al., *Bio/Technology*, 9:421 (1991).

Exemplary human framework sequences useful for human adaptation are disclosed at, e.g., www.ncbi.nlm.nih.gov/entrez/query.fcgi; www.ncbi.nih.gov/igblast; www.atcc.org/phage/hdb.html"; "www.mrc-cpe.cam.ac.uk/ALIGNMENTS.php"; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de; immuno.bme.nwu.edu; www.mrc-cpe.cam.ac.uk; www.ibt.unam.mx/vir/V_mice.html; www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; imgt.cines.fr; and Kabat et al., Sequences of Proteins of Immunological Interest, U.S. Dept. Health (1987), each entirely incorporated herein by reference.

Fully human mAbs lacking any non-human sequences can be prepared from human immunoglobulin transgenic mice by techniques referenced in, e.g., Lonberg et al., *Nature* 368: 856-859 (1994); Fishwild et al., *Nature Biotechnology* 14:845-851 (1996) and Mendez et al., *Nature Genetics* 15:146-156 (1997). Human mAbs can also be prepared and optimized from phage display libraries by techniques referenced in, e.g., Knappik et al., *J. Mol. Biol.* 296:57-86 (2000) and Krebs et al., *J. Immunol. Meth.* 254:67-84 (2001).

The term "proliferation rate" as used herein refers to the change in the number of cells per unit time or the change in the number of cells exhibiting a marker of progression through the cell cycle toward cell division, per unit time. Such markers may be morphological, indicators of DNA replication or expressed gene products.

The term "TLR3 biological activity" or "TLR3 receptor activation" as used herein refers to any activities occurring as a result of ligand binding to cell surface TLR3.

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention relates to antagonists capable of inhibiting TLR3 receptor-mediated signaling and uses of such antagonists. Such TLR3 antagonists may have the properties of binding a TLR3 receptor and inhibiting TLR3 receptor-mediated signaling. Exemplary mechanisms by which TLR3 signaling may be inhibited by such antagonists include inhibition of kinase activity, transcript reduction or receptor antagonism. Other antagonists capable of inhibiting TLR3 receptor-mediated signaling by other mechanisms are also within the scope of the various aspects and embodiments of the invention. These antagonists are useful as research reagents, diagnostic reagents and therapeutic agents.

One aspect of the present invention is an antagonist of Toll Like Receptor 3 (TLR3) that inhibits cellular production of RANTES (Regulated on Activation, Normal T-cell Expressed and Secreted) cytokine. Another aspect of the invention is an antagonist of TLR3 that inhibits cellular production of RANTES and a cytokine selected from the group consisting of interleukin-6 (IL-6), interleukin-8 (IL-8) and macrophage inflammatory protein-1 alpha (MIP1-alpha).

In another aspect, the invention provides an isolated antibody reactive with TLR3 having the antigen binding ability of a monoclonal antibody having the amino acid sequences of the heavy chain complementarity determining regions (CDRs) as shown in SEQ ID NOs: 9 ($V_H$ CDR1), 11 ($V_H$ CDR2) and 13 ($V_H$ CDR3) and the amino acid sequences of the light chain CDRs as shown in SEQ ID NOs: 19 ($V_L$ CDR1), 21 ($V_L$ CDR2) and 23 ($V_L$ CDR3). An exemplary antibody is a monoclonal antibody comprising heavy chain CDR amino acid sequences as shown in SEQ ID NOs: 9, 11 and 13 and light chain CDR amino acid sequences as shown in SEQ ID NOs: 19, 21 and 23.

Another aspect of the invention is an isolated antibody reactive with TLR3 comprising a $V_H$ having the amino acid sequence shown in SEQ ID NO: 6 and a $V_L$ having the amino acid sequence shown in SEQ ID NO: 16.

Another aspect of the invention are isolated polynucleotides encoding any of the antibodies or other protein TLR3 antagonists of the invention or its complement. Certain exemplary polynucleotides are disclosed herein, however, other polynucleotides which, given the degeneracy of the genetic code or codon preferences in a given expression system, encode the antibodies or other protein TLR3 antagonists of the invention are also within the scope of the invention.

Another aspect of the invention is an antibody heavy chain comprising the CDR amino acid sequences shown in SEQ ID NOs: 9, 11 and 13.

Another aspect of the invention is an isolated polynucleotide encoding an antibody light chain comprising the CDR amino acid sequences shown in SEQ ID NOs: 19, 21 and 23.

Another aspect of the invention is an isolated polynucleotide encoding an antibody heavy chain comprising the amino acid sequence shown in SEQ ID NO: 6. An exemplary polynucleotide sequence is shown in SEQ ID NO: 5.

Another aspect of the invention is an isolated polynucleotide encoding an antibody light chain comprising the amino acid sequence shown in SEQ ID NO: 16. An exemplary polynucleotide sequence is shown in SEQ ID NO: 15.

Another aspect of the present invention is a human-adapted mAb comprising a $V_H$ amino acid sequence as shown in SEQ ID NO: 25, 27, 29 or 31 and a $V_L$ amino acid sequence as shown in SEQ ID NO: 33, 35, 37 or 39. Isolated polynucleotides encoding the $V_H$ amino acid sequences shown in SEQ ID NO: 25, 27, 29 and 31 and the $V_L$ amino acid sequences shown in SEQ ID NO: 33, 35, 37 and 39 are also an aspect of the invention. These human-adapted mAbs comprise the $V_H$ CDR amino acid sequences shown in SEQ ID NOs: 9, 11 and 13 and the $V_L$ CDR amino acid sequences shown in SEQ ID NOs: 19, 21 and 23. Exemplary nucleic acid sequences encoding the $V_H$ amino acid sequences of SEQ ID NO: 25, 27, 29 and 31 are shown in SEQ ID NOs: 26, 28, 30 and 32, respectively. Exemplary nucleic acid sequences encoding the $V_L$ amino acid sequences of SEQ ID NO: 33, 35, 37 and 39 are shown in SEQ ID NOs: 34, 36, 38 and 40, respectively. One particular embodiment of a human-adapted monoclonal antibody of the invention comprises a $V_H$ amino acid sequence as shown in SEQ ID NO: 25 and a $V_L$ amino acid sequence as shown in SEQ ID NO: 33.

Another embodiment of the present invention is an isolated antibody having a $V_H$ CDR1 amino acid sequence as shown in Formula (I):

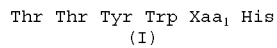
```
Thr Thr Tyr Trp Xaa₁ His
              (I)
``` wherein $Xaa_1$ is Ile or Met (SEQ ID NO: 61);
a $V_H$ CDR2 amino acid sequence as shown in Formula (II):

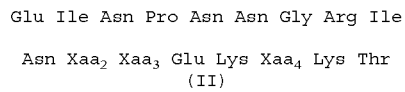
```
Glu Ile Asn Pro Asn Asn Gly Arg Ile
Asn Xaa₂ Xaa₃ Glu Lys Xaa₄ Lys Thr
              (II)
``` wherein $Xaa_2$ is Tyr or Gly, $Xaa_3$ is Asn or Ala and $Xaa_4$ is Phe or Gly (SEQ ID NO: 62); and
a $V_H$ CDR3 amino acid sequence as shown in Formula (III):

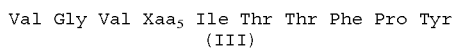
```
Val Gly Val Xaa₅ Ile Thr Thr Phe Pro Tyr
                    (III)
``` wherein $Xaa_5$ is Met or Ile (SEQ ID NO: 63);
and $V_L$ CDRs having the amino acid sequences shown in SEQ ID NOs: 19, 21 and 23.

Exemplary species include an antibody having a $V_L$ amino acid sequence as shown in SEQ ID NO: 33 and a $V_H$ amino acid sequence comprising a $V_L$-CDR1 of Formula (I) where $Xaa_1$ is Met and $V_L$-CDR2 and $V_L$-CDR3 amino acid sequences as shown in SEQ ID NOs: 11 and 13, respectively (SEQ ID NO: 45, exemplary nucleic acid shown in SEQ ID NO: 46). In this species, $Xaa_1$ is Met; $Xaa_2$ is Tyr; $Xaa_3$ is Asn; $Xaa_4$ is Phe; and $Xaa_5$ is Met.

Other exemplary species include antibodies having a $V_L$ amino acid sequence as shown in SEQ ID NO: 33 and a $V_H$ amino acid sequence comprising $V_H$-CDR1 and $V_H$-CDR3 amino acid sequences as shown in SEQ ID NOs: 9 and 13, respectively and a $V_H$-CDR2 of Formula (II) where:
$Xaa_2$ is Gly, $Xaa_3$ is Asn and $Xaa_4$ is Phe (SEQ ID NO: 47, exemplary nucleic acid sequence shown in SED ID NO: 48);
$Xaa_2$ is Tyr, $Xaa_3$ is Ala and $Xaa_4$ is Phe (SEQ ID NO: 49, exemplary nucleic acid sequence shown in SED ID NO: 50); and
$Xaa_2$ is Tyr, $Xaa_3$ is Asn and $Xaa_4$ is Gly (SEQ ID NO: 51, exemplary nucleic acid sequence shown in SED ID NO: 52).

Other exemplary species include an antibody having a $V_L$ amino acid sequence as shown in SEQ ID NO: 33 and a $V_H$ amino acid sequence comprising $V_H$-CDR1 and $V_H$-CDR2 amino acid sequences as shown in SEQ ID NOs: 9 and 11, respectively and a $V_H$-CDR3 of Formula (III) where $Xaa_5$ is Ile (SEQ ID NO: 53, exemplary nucleic acid sequence shown in SED ID NO: 54).

In sum, exemplary species include antibodies having one of the following $V_L$ and $V_H$ amino acid sequence combinations:

| $V_L$ SEQ ID NO: | $V_H$ SEQ ID NO: |
|---|---|
| 33 | 45 |
| 33 | 47 |
| 33 | 49 |
| 33 | 51 |
| 33 | 53 |

The invention further includes isolated antibodies wherein the $V_H$ has the amino acid sequence shown in SEQ ID NO: 45, 47, 49, 51 or 53 and the $V_L$ has the amino acid sequence shown in SEQ ID NO: 33, 35, 37 or 39.

Exemplary antibody antagonists may be antibodies of the IgG, IgD, IgGA or IgM isotypes. Additionally, such antagonist antibodies can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function. See Deckert et al., *Int. J. Cancer* 87: 382-390, 2000; Knight et al., *Platelets* 15: 409-418, 2004; Leong et al., *Cytokine* 16: 106-119, 2001; and Yang et al., *Protein Eng.* 16: 761-770, 2003.

Pharmacokinetic properties of the antibodies of the invention could also be enhanced through Fc modifications by techniques known to those skilled in the art. For example, IgG4 isotype heavy chains contain a Cys-Pro-Ser-Cys (CPSC) motif in their hinge regions capable of forming either inter- or intra-heavy chain disulfide bonds, i.e., the two Cys residues in the CPSC motif may disulfide bond with the corresponding Cys residues in the other heavy chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, *Immunology* 105: 9-19 (2002)). Accordingly, since the heavy:light chain (HL) pairs in those IgG4 molecules with intra-heavy chain bonds in the hinge region are not covalently associated with each other, they may dissociate into HL monomers that then reassociate with HL monomers derived from other IgG4 molecules forming bispecific, heterodimeric IgG4 molecules. In a bispecific IgG antibody the two Fabs of the antibody molecule differ in the epitopes that they bind. Substituting Ser228 in the hinge region of IgG4 with Pro results in "IgG1-like behavior," i.e., the molecules form stable disulfide bonds between heavy chains and therefore, are not susceptible to HL exchange with other IgG4 molecules. In one embodiment, the antibodies of the invention will comprise an IgG4 Fc domain with a S228P mutation.

Further, sites can be removed that affect binding to Fc receptors other than an FcRn salvage receptor in the antibodies of the invention. For example, the Fc receptors involved in ADCC activity can be removed in the antibodies of the invention. For example, mutation of Leu234/Leu235 in the hinge region of IgG1 to L234A/L235A or Phe234/Leu235 in the hinge region of IgG4 to P234A/L235A minimizes FcR binding and reduces the ability of the immunoglobulin to mediate complement dependent cytotoxicity and ADCC. In one embodiment, the antibodies of the invention will comprise an IgG4 Fc domain with P234A/L235A mutations.

In another embodiment of the invention, the antibodies will comprise an IgG4 Fc domain with S108P, P114A and L115A mutations, the Fc domain having the amino acid sequence shown in SEQ ID NO: 41. An exemplary nucleic acid sequence encoding SEQ ID NO: 41 is shown in SEQ ID NO: 42. In a full-length IgG4 heavy chain, the mutation coordinates are S228P, P234A and L235A.

Fully human, human-adapted, humanized and affinity-matured antibody molecules or antibody fragments are within the scope of the invention as are mimetibodies, fusion proteins and chimeric proteins.

The antagonists of the invention may bind TLR3 with a $K_d$ less than or equal to about $10^{-7}$, $10^{-8}$, $10^{-9}10^{-10}$, $10^{-11}$ or $10^{-12}$ M. The affinity of a given molecule for a TLR3 receptor, such as hTLR3 can be determined experimentally using any suitable method. Such methods may utilize Biacore or KinExA instrumentation, ELISA or competitive binding assays known to those skilled in the art.

Antagonist molecules binding a given TLR3 homolog with a desired affinity can be selected from libraries of variants or fragments by techniques including antibody affinity maturation and other art-recognized techniques suitable for non-antibody molecules.

Another embodiment of the invention is a vector comprising at least one polynucleotide of the invention. Such vectors may be plasmid vectors, viral vectors, transposon based vectors or any other vector suitable for introduction of the polynucleotides of the invention into a given organism or genetic background by any means.

Another embodiment of the invention is a host cell comprising any of the polynucleotides of the invention such as a polynucleotide encoding a polypeptide comprising SEQ ID NO: 9, SEQ ID NO: 11 and SEQ ID NO: 13 and a polynucleotide encoding a polypeptide comprising SEQ ID NO: 19, SEQ ID NO: 21 and SEQ ID NO: 23. Other exemplary host cells comprise a polynucleotide encoding a polypeptide comprising one of SEQ ID NOs: 25, 27, 29, 31, 45, 47, 49, 51 or 53 and a polynucleotide encoding a polypeptide comprising SEQ ID NO: 33, 35, 37 or 39. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1 (ATCC CRL-61) or DG44.

Another embodiment of the invention is a method of making an antibody reactive with TLR3 comprising culturing a host cell of the invention and recovering the antibody produced by the host cell. Such an antibody may be the TLR3 antagonist antibody exemplified below as mAb 1068 comprising heavy and light amino acid sequences as shown in SEQ ID NOs: 6 and 16, respectively or a human-adapted or human-adapted CDR variant of mAb 1068 comprising heavy chain amino acid sequences as shown in SEQ ID NOs: 25, 27, 29, 31, 45, 47, 49, 51 or 53 and light chain amino acid sequences as shown in SEQ ID NOs: 33, 35, 37 or 39.

Another embodiment of the invention is a hybridoma cell line that produces an antibody of the invention.

Methods of Treatment

The present invention provides methods of prevention and treatment for conditions where attenuation of TLR3 activity is desirable. Conditions that can be treated or prevented with a TLR3 antagonist include those mediated by cytokines and those that result wholly or partially from activation of TLR3 or signaling through the TLR3 pathway. The invention includes a method of inhibiting cellular production of RANTES or RANTES together with IL-6, IL-8 or MIP1-alpha comprising contacting a TLR3 antagonist such as an isolated antibody disclosed herein with a cell that expresses a TLR3 receptor for a time sufficient to inhibit the production of these cytokines.

The methods of the invention may be used to treat an animal patient belonging to any classification. Examples of such animals include mammals such as humans, rodents, dogs, cats and farm animals and other animal classes such as birds, reptiles and fish. Without wishing to be bound by any particular theory, it is believed that the therapeutic benefit of TLR3 antagonists will be due to the ability of such antagonists to inhibit the secretion of pro-inflammatory chemokines and cytokines involved in some inflammatory conditions. It also is believed that the therapeutic benefit of TLR3 antagonists will be due to the ability of such antagonists to increase cell proliferation and thus promote tissue repair.

For example, the methods of the invention are useful in treating or preventing inflammatory conditions and promoting tissue repair (such as wound or burn healing after traumatic injury) in a patient. Further, the methods of the invention also provide for cell densities in vitro.

Any TLR3 antagonist could be used in the methods of prevention and treatment of the invention. As an example, any of the isolated antibodies disclosed herein are useful as a TLR3 antagonist in the treatment or prevention of inflammatory conditions or promoting tissue repair. In particular, an isolated antibody reactive with TLR3 having the antigen binding ability of a monoclonal antibody comprising $V_H$ CDR amino acid sequences as shown SEQ ID NO: 9, SEQ ID NO: 11 and SEQ ID NO: 13 and $V_L$ CDR amino acid sequences as shown in SEQ ID NO: 19, SEQ ID NO: 21 and SEQ ID NO: 23 is useful. Other useful antibodies comprise a $V_H$ having an amino acid sequence as shown in SEQ ID NOs: 25, 27, 29, 31, 45, 47, 49, 51 or 53 and a $V_L$ having an amino acid sequence as shown in SEQ ID NOs: 33, 35, 37 or 39.

Amounts of a given TLR3 antagonist sufficient to treat or prevent a given inflammatory condition can be readily determined. In the methods of the invention, the TLR3 antagonist may be administered singly or in combination with at least one other molecule. Such additional molecules may be other TLR3 antagonist molecules or molecules with a therapeutic benefit not mediated by TLR3 receptor signaling. Antibiotics, antivirals, palliatives and other compounds that reduce cytokine levels or activity are examples of such additional molecules.

In another embodiment of the methods of treating or preventing inflammatory conditions, TLR3 activity is decreased by inhibiting TLR3 gene expression. TLR3 gene expression can be inhibited by any means that decreases expression of TLR3 biological activity to inhibit TLR3 mediated signaling. Such means include, for example, gene inactivation through recombination to inactivate genomic DNAs (e.g., gene knock-out, promoter hijacking or other gene mutagenesis methods) and gene transcript inactivation (e.g., silencing RNAs or anti-sense RNAs). Those skilled in the art will recognize many other means for decreasing expression of active TLR3.

Thus, an aspect of the invention is a method of treating or preventing an inflammatory condition comprising administering a therapeutically effective amount of a TLR3 antagonist to a patient in need thereof for a time sufficient to treat or prevent the inflammatory condition.

One example of such inflammatory conditions is sepsis-associated conditions. Sepsis is a systemic response to infection, which causes organ failure and death in severe cases. Sepsis is medically defined as systemic inflammatory response syndrome (SIRS) resulting from a viral, bacterial, fungal, or parasitic infection. dsRNA released by viral, bacterial, fungal, or parasitic infection and by necrotic cells can contribute to the onset of sepsis. Sepsis-associated conditions may include SIRS, septic shock or multiple organ dysfunction syndrome (MODS). While not wishing to be bound by an particular theory, it is believed that treatment with TLR3 antagonists can provide a therapeutic benefit by extending survival times in patients suffering from sepsis-associated inflammatory conditions or prevent a local inflammatory event (e.g., in the lung) from spreading to a systemic condition, by potentiating innate antimicrobial activity, by demonstrating synergistic activity when combined with antimicrobial agents, by minimizing the local inflammatory state contributing to the pathology, or any combination of the foregoing. Such intervention may be sufficient to permit additional treatment (e.g., treatment of underlying infection or reduction of cytokine levels) necessary to ensure patient survival.

Another example of such inflammatory conditions is inflammatory bowel diseases. The inflammatory bowel disease may be Crohn's disease or ulcerative colitis. Those skilled in the art will recognize other inflammatory bowel diseases of known or unknown etiology that cause inflammation of the bowel. Further, TLR3 antagonists will be useful for the treatment and prevention of extraintestinal sequelae associated with ulcerative colitis or Crohn's disease such as arthralgias and arthritis that include ankylosing spondylitis, sacroiliitis and psoriatic spondyloarthritis. Other extraintestinal sequelae include mucocutaneous lesions such as oral ulcers, erythema nodosum (the development of painful indurated ovoid nodules) and pyoderma gangrenosum characterized by a deep severe ulceration of the skin; opthlamologic complications such as episcleritis, iritis and uveitis; renal diseases such as nephrolithiasis; hepatobiliary diseases such as primary sclerosing cholangitis, a chronic liver disease characterized by fibrosing inflammation associated with ulcerative colitis Crohn's disease; and bone diseases including osteoporosis and osteopenia which can occur as a complication of prolonged corticosteroid use. Also included are IBD-induced pulmonary dysfunction and respiratory disorders including interstitial pneumonitis, tracheal stenosis, bronchiolitis, bronchiolitis obliterans organizing pneumonia, pulmonary vasculitis, sarcoidosis, chronic bronchitis, and clinical conditions showing pulmonary infiltrates with eosinophilia.

Another example of such inflammatory conditions is infection-associated conditions. Infection-associated conditions may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection.

Another example of such inflammatory conditions is an inflammatory pulmonary condition. Exemplary inflammatory pulmonary conditions include infection induced pulmonary conditions including those associated with viral, bacterial, fungal, parasite or prion infections; allergen induced pulmonary conditions; pollutant induced pulmonary conditions such as asbestosis, silicosis, or berylliosis; gastric aspiration induced pulmonary conditions; immune dysregulation; genetically induced inflammatory pulmonary conditions such as cystic fibrosis; and physical trauma induced pulmonary conditions, such as ventilator injury. These inflammatory conditions also include asthma, emphysema, bronchitis, COPD, sarcoidosis, histiocytosis, lympangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, human metapneumovirus infection, respiratory syncitial virus infection and aspergillus or other fungal infections.

Another example of such inflammatory conditions is Type 2 diabetes, obesity, dislipidemia and metabolic syndrome. TLR3 antagonists are useful for the inhibition of inflammatory processes associated with obesity and insulin resistance. Inhibition of TLR3 signaling would improve a patient's lipid profile, namely a decrease in total cholesterol levels and increase in HDlc/LDLc ratio. Inhibition of TLR3 signaling would also lead to an increase in insulin secretion thus leading to an improvement in insulin resistance. Current treatments for Type 2 diabetes are associated with a variety of deleterious side effects including hypoglycemia and weight gain. Using a TLR3 antagonist for the treatment of Type 2 diabetes is expected to have fewer side effects and sustained pharmacokinetic profile. Further, treatment with a compound that has a long circulating half-life, such as an isolated antibody of the invention, would require infrequent dosing.

Additionally, the improvements in lipid profile are likely to delay or prevent development of cardiovascular diseases associated with obesity and type 2 diabetes, such as atherosclerosis. In addition, inhibition of TLR3 signaling could lead to the increase in circulating levels of insulin either via direct effects on pancreatic islet cells or by affecting the lipid profile and protecting the islets from deterioration induced by high lipid levels. Therefore, TLR3 inhibition alone or in combination with other therapies is likely to postpone the introduction of insulin treatment in type 2 diabetics and avoid unwanted side effects associated with insulin treatment.

Further, patients with Hepatitis C and HIV infections are prone to development of insulin resistance and type 2 diabetes due to the accumulation of lipid in liver or the inability of the liver to respond to insulin stimulation due to cirrhosis or fibrosis resulting from the treatment agents. Inhibition of TLR3 signaling by a TLR3 antagonist could target both the infection and insulin resistance in this highly compromised patient population.

Other inflammatory conditions and neuropathies, which may be prevented or treated by the method of the invention include multiple sclerosis, sclerosis lupus erythematous, and neurodegenerative and central nervous system (CNS) disorders including Alzheimer's disease, Parkinson's disease, Huntington's disease, bipolar disorder and Amyotrophic Lateral Sclerosis (ALS), liver diseases including fibrosis, hepatitis C virus (HCV) and hepatitis B virus (HBV), arthritis, rheumatoid arthritis, psoriatic arthritis and juvenile rheumatoid arthritis (JRA), osteoporosis, osteoarthritis, pancreatitis, fibrosis, encephalitis, psoriasis, Giant cell arteritis, ankylosing spondolytis, autoimmune hepatitis, human immunodeficiency virus (HIV), inflammatory skin conditions, transplant, cancer, allergies, endocrine diseases, other autoimmune disorders and airway hyper-responsiveness.

Another aspect of the present invention is a method of increasing the proliferation rate of a cell comprising decreasing TLR3 activity in the cell by, e.g., contacting the cell with a TLR3 antagonist. In one embodiment of this aspect of the invention, the cell can be from tissue such as epithelium or colonic tissue. Epithelial cells may originate from any epithelial tissue such as, for example, gastrointestinal tract epithelium, skin epithelium, lung epithelium, or bronchopulmonary epithelium. Inflammatory conditions may affect any tissue such as, for example, cardiac tissue and tissues of the gastrointestinal tract resulting in structural and functional deviations from normal tissue. In some instances, such inflammatory conditions may be the result of genetic factors or infection. In other situations, such inflammatory conditions may be the result of traumatic injuries such as, for example, burns. Those skilled in the art will recognize many different inflammatory conditions and the associated pathologies exhibited by the different tissues involved.

Another aspect of the invention is a method of treating a condition resulting from cell death comprising administering a therapeutically effective amount of a TLR3 antagonist to a patient in need thereof for a time sufficient to treat the condition.

Another aspect of the invention is a method of preventing a condition resulting from cell death comprising administering a therapeutically effective amount of a TLR3 antagonist to a patient in need thereof for a time sufficient to prevent the condition.

Administration/Pharmaceutical Compositions

The mode of administration for therapeutic use of the antagonists of the invention may be any suitable route that delivers the agent to the host. The proteins, antibodies, antibody fragments and mimetibodies and pharmaceutical compositions of these agents are particularly useful for parenteral administration, i.e., subcutaneously, intramuscularly, intradermally, intravenously, intranasally or by inhalation.

Antagonists of the invention may be prepared as pharmaceutical compositions containing an effective amount of the antagonist as an active ingredient in a pharmaceutically acceptable carrier. An aqueous suspension or solution containing the antagonist, preferably buffered at physiological pH, in a form ready for injection is preferred. The compositions for parenteral administration will commonly comprise a solution of the antagonist of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions such as pH adjusting and buffering agents, etc. The concentration of the antagonist of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antagonist of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The antagonists of the invention, when in a pharmaceutical preparation, can be present in unit dose forms. The appropriate therapeutically effective dose can be determined readily by those of skill in the art. A determined dose may, if necessary, be repeated at appropriate time intervals selected as appropriate by a physician during the treatment period.

The antagonists of the invention can be lyophilized for storage and reconstituted in a suitable carrier prior to use. This technique has been shown to be effective with conventional immunoglobulins and protein preparations and art-known lyophilization and reconstitution techniques can be employed.

Antagonists may be administered by any technique that provides such molecules to a cell. For a cell, in vitro antagonist administration may be, for example, by supplementing the culture medium with the antagonist. For a cell, in vivo antagonist administration may be, for example, by intravenous injection of the antagonist into an animal or tissue. Those skilled in the art will recognize other means for administering antagonists to a cell in vitro or in vivo. Such means also include those modes for delivery of an agent to a host that are discussed above.

The present invention will now be described with reference to the following specific, non-limiting examples.

Example 1

Identification of Anti-hTLR3 Antagonist mAbs

Anti-hTLR3 antagonist mabs able to block signaling through the hTLR3 receptor were identified by cell-based screening assays. A pool of hybridomas producing anti-hTLR3 mAbs was generated in BALB/C mice using standard techniques (Kohler et al., 1976). Mice were immunized with hTLR3 by intradermal injections of plasmid DNA encoding amino acids 1-703 of hTLR3 (SEQ ID NO: 3). Amino acids 1-703 correspond to the predicted extracellular domain of hTLR3 (SEQ ID NO: 4). Mice were initially injected with 10 ug of plasmid DNA followed by a second 10 μg DNA injection two weeks later. A booster injection of 15 μg of DNA was administered to each mouse two weeks after the second 10 μg plasmid DNA injection. Three days prior to B cell fusion mice were intravenously injected with 15 μg of hTLR3 protein in phosphate buffered saline (PBS; 10 mM phosphate, 150 mM NaCL, pH 7.4). Spleens from immunized mice were then harvested and B cell fusion was performed using standard methods (Kohler et al., 1976). Hybridomas were selected using medium containing hypoxanthine-aminopterin-thymidine and screened initially for anti-TLR3 antibodies by enzyme-linked immunosorbent assay (ELISA). Individual hybridomas producing anti-hTLR3 mabs were cloned by limiting dilution.

Hybridomas producing anti-TLR3 antagonist mAbs were identified by cell based screening assays utilizing a human A549 derived lung epithelial cell line stably over-expressing hTLR3. A549 cells (ATCC CRL: CCL-185) used for the generation of the screening and control cell lines for these assays were obtained from the American Type Culture Collection (Manassas, Va.). The screening cell line was an A549 derived cell line named A549-hTLR3. A549-hTLR3 cells are stably transfected with a mammalian plasmid expression vector encoding hTLR3 and a neomycin resistance gene. The control A549 derived cell line was named A549-neo. A549-neo cells are stably transfected with the mammalian plasmid expression vector encoding the neomycin resistance gene alone. These stably transfected cell lines were generated by Lipofectamine® (Invitrogen, Inc., Carlsbad, Calif.) transfection according to the manufacturer's instructions and standard methods of selection and cloning. A549-hTRL3 and A549-neo cells were cultured under standard conditions in Minimal Essential Media (MEM) containing 10% FBS, 1% MEM non-essential amino acids (Gibco Invitrogen, Inc., Carlsbad, Calif.), 1 mM glutamine, 1 mM sodium pyruvate, 20 mM HEPES and 0.5 mg/ml G418.

Cell based screening assays using A549-hTLR3 cells identified one hTLR3 antagonist mAb designated mAb 1068. The principle underlying these screening assays was that poly(I: C) stimulation of the hTLR3 receptor present in A549-hTLR3 cells results in increased cellular cytokine production. Candidate hTLR3 antagonist mAbs identified via screening assays will inhibit poly(I:C) mediated signaling through the hTLR3 receptor in A549-hTLR3 cells and cause decreased cytokine production relative to control A549-hTLR3 cells not exposed to mAbs.

Screening assays were performed by incubating A549-hTLR3 cells with a test mAb for 30 min. at 37° C. prior to addition of 5 μg/ml poly(I:C) (Amersham Biosciences Corp., Piscataway, N.J.); 24 hrs later cytokine levels in cell culture supernatants were measured. Control A549-hTLR3 cells were treated identically, although these cells were not incubated with a test mAb. Luminex® multichannel analysis (Luminex Corp., Austin, Tex.) and IL-6 (interleukin-6), IL-8 (interleukin-8), and RANTES (Regulated Upon Activation, Normally T-Expressed, and presumably Secreted) specific mAb conjugated beads were used as directed by the manufacturer to measure cellular cytokine production levels in screening assays. The hTLR3 binding, antagonist mAb 1068 was identified by such assays.

Heavy and light chain nucleic acid sequences encoding the heavy and light chains of mAb 1068 were cloned from the hybridoma expressing mAb 1068 using standard methods. The mAb 1068 heavy chain and light chain nucleic acid and amino acid sequences are shown in FIGS. 1 and 2 and SEQ ID NOs: 6 and 16, respectively. A cell line comprising both the heavy chain and light chain nucleic acid sequences encoding recombinant mAb 1068 (r1068) was generated using standard methods.

Figure 4:
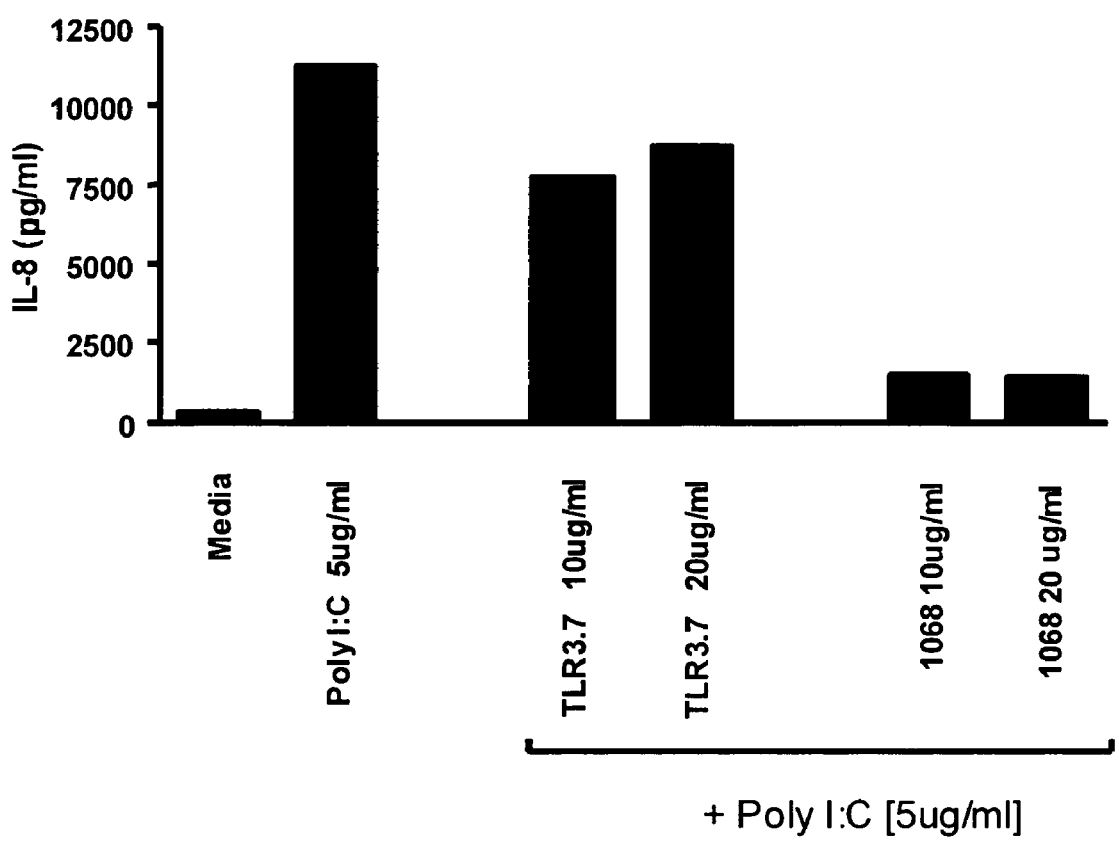
FIG. 4 shows inhibition of poly(I:C) induced IL-8 cytokine production in human lung epithelium derived cells by a TLR3 antagonist.
Figure 5:
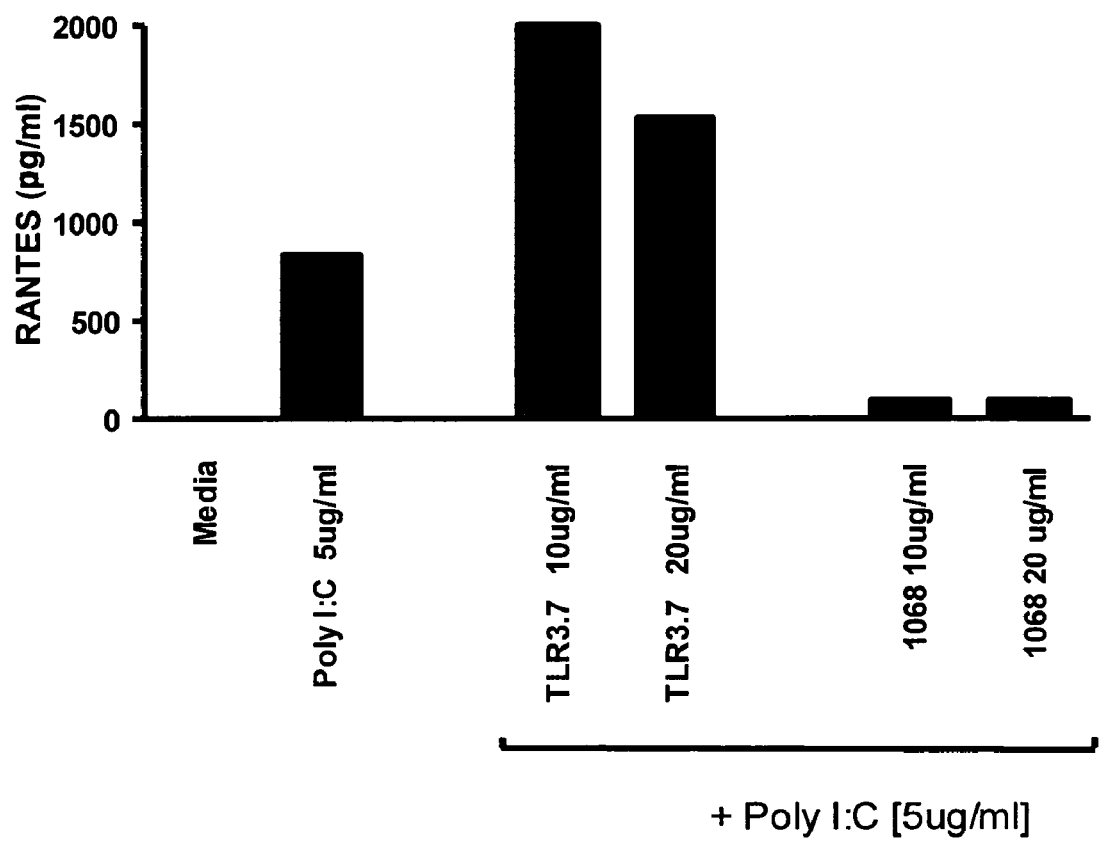
FIG. 5 shows inhibition of poly(I:C) induced RANTES cytokine production in human lung derived cells by a TLR3 antagonist.

Example 2 hTLR3 Antagonist Inhibition of IL-6, IL-8 and RANTES Cytokine Production in Human Lung Derived Cells IL-6, IL-8 and RANTES specific cytokine assays were performed by incubating A549-hTLR3 cells with the 1068 mAb or TLR3.7 mAb for 30 min. at 37° C. prior to addition of 5 µg/ml poly(I:C) (Amersham Biosciences Corp., Piscataway, N.J.) as indicated in FIG. 3, FIG. 4 and FIG. 5. Cytokine levels in cell culture supernatants were measured 24 hrs later using Luminex® instrumentation (Luminex Corp., Austin, Tex.) and IL-6, IL-8 or RANTES specific mAb conjugated beads as appropriate. Luminex® assays for each cytokine were performed as directed by the manufacturer.

The results indicate that the hTLR3 antagonist mAb 1068 inhibits hTLR3-mediated production of IL-6 (FIG. 3), IL-8 (FIG. 4) and RANTES (FIG. 5) cytokines in human lung epithelium derived A549-hTLR3 cells. However, the hTLR3 specific murine mAb TLR3.7 (eBioscience, San Diego, Calif.) did not inhibit hTLR3 mediated, poly(I:C) induced production of IL-6 (FIG. 3) and IL-8 (FIG. 4) to the same extent as mAb 1068. With respect to RANTES production (FIG. 5) in these human lung-derived cells, mAb 1068 inhibited production while mAb TLR3.7 increased production of RANTES. These distinctions between the 1068 and TLR3.7 mabs are important as previous work suggested the TLR3.7 mAb might antagonize the hTLR3 receptor (Matsumoto M. et al., *Biochem. Biophys Res. Commun.* 24:1364-1369 (2002)). This previous work reported that the TLR3.7 mAb appeared to inhibit poly(I:C) induced IFN-beta production in human fibroblast derived MRC-5 cells (Matsumoto M. et al., *Biochem. Biophys Res. Commun.* 24:1364-1369 (2002)). The results here clearly indicate that the 1068 hTLR3 antagonist mAb inhibits production of a much broader spectrum of cytokines than the TLR3.7 mAb and that these two mAbs can be distinguished from each on this basis.

Figure 6:
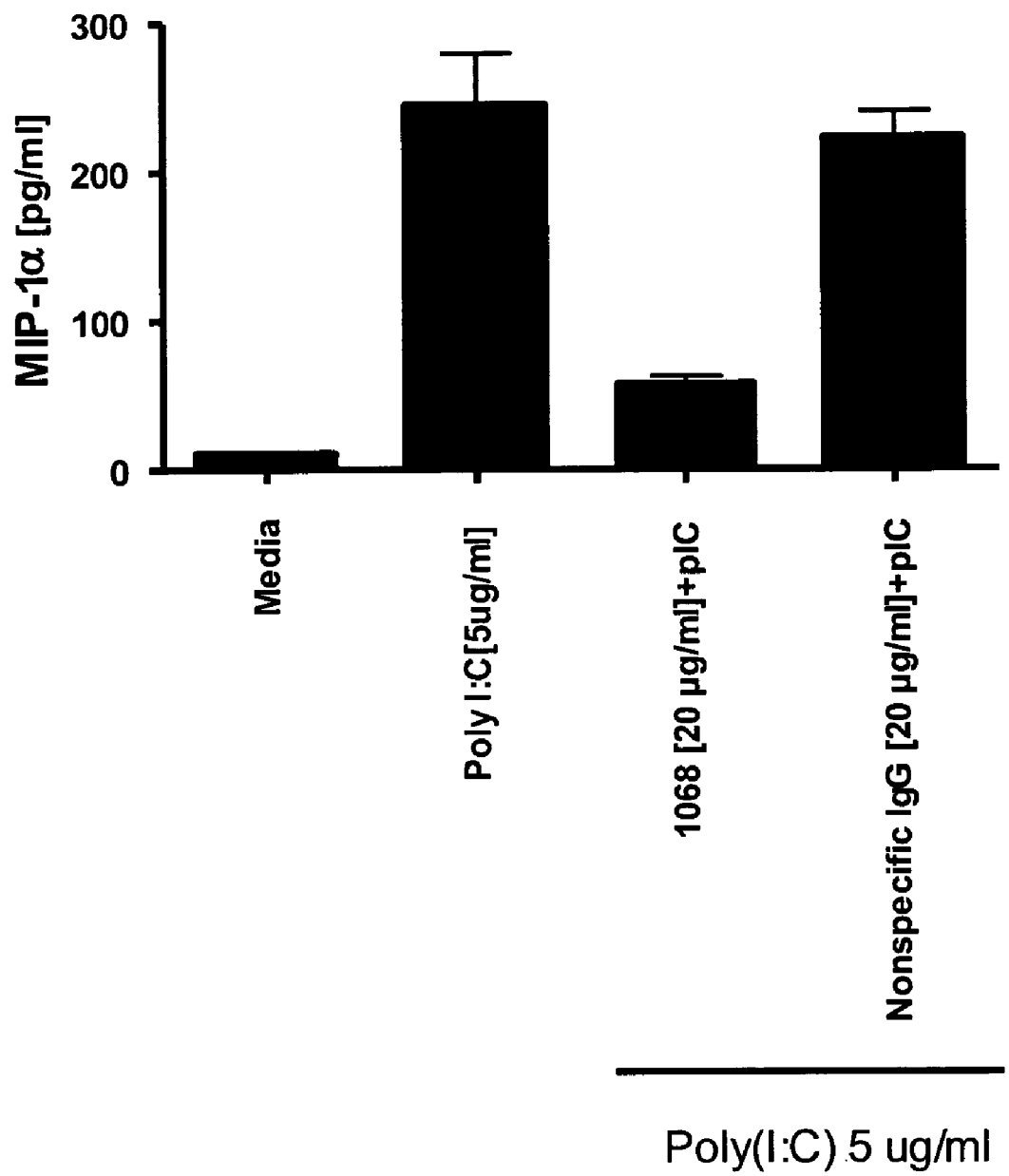
FIG. 6 shows inhibition of poly(I:C) induced MIP1-alpha cytokine production in primary human broncho-epithelial cells by a TLR3 antagonist.
Figure 7:
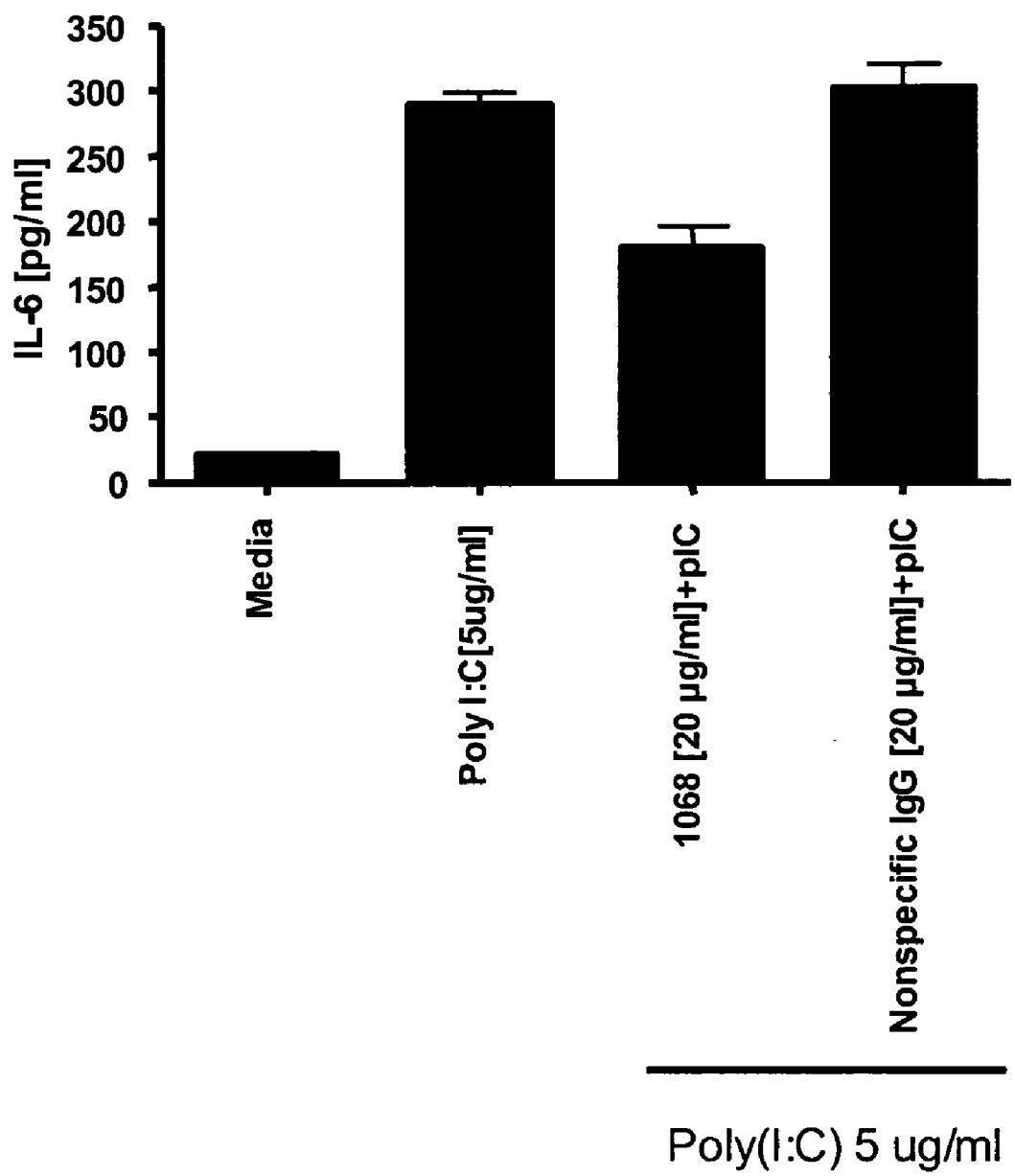
FIG. 7 shows inhibition of poly(I:C) induced IL-6 cytokine production in primary human broncho-epithelial cells by a TLR3 antagonist.

Example 3 hTLR3 Antagonist Inhibition of MIP1-Alpha and IL-6 Cytokine Production in Primary Human Broncho-Epithelial Cells The hTLR3 antagonist mAb 1068 inhibits hTLR3-mediated production of the MIP1-alpha (FIG. 6) and IL-6 (FIG. 7) cytokines in primary human broncho-epithelial cells. MIP1-alpha and IL-6 specific cytokine assays were performed by incubating primary human broncho-epithelial cells with the 1068 mAb or a nonspecific polyclonal mouse IgG preparation for 30 min. at 37° C. prior to addition of 5 µg/ml poly(I:C) (Amersham Biosciences Corp., Piscataway, N.J.) as indicated in FIG. 6 or FIG. 7. Cytokine levels in cell culture supernatants were measured 24 hrs later using Luminex® instrumentation (Luminex Corp., Austin, Tex.) and MIP1-alpha or IL-6 specific mAb conjugated beads as appropriate. Luminex® assays for each cytokine were performed as directed by the manufacturer. Primary human broncho-epithelial cells were isolated from human tissue samples and cultured using standard methods.

Example 4

Figure 8:
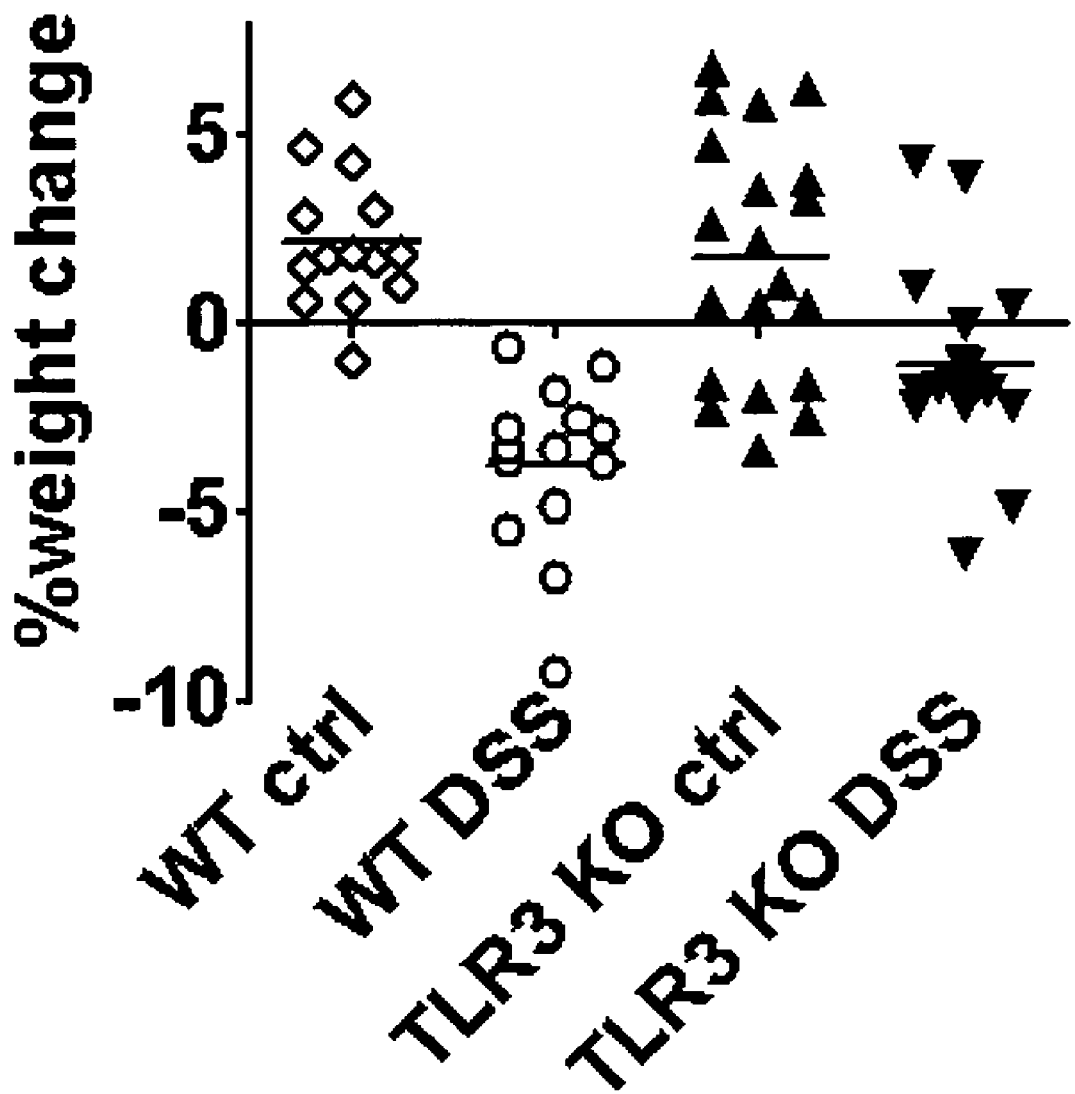
FIG. 8 shows the effect of knocking out TLR3 activity on IBD-associated weight loss.

Knocking Out TLR3 Activity Eases the Severity of Inflammatory Bowel Disease Symptoms The severity of inflammatory bowel disease (IBD) symptoms was decreased in a murine model of IBD by knocking-out TLR3 receptor gene activity (FIG. 8). Crohn's Disease and ulcerative colitis can be modeled in animals that have ingested dextran sulfate sodium (DSS) (Hendrickson B. A. et al., *Clin Microbiol Rev.* 15:79-94, 2002). The symptoms observed in these animal models include substantial weight loss (FIG. 8) and epithelial cell ulceration. These symptoms mimic those symptoms observed in patients with IBD such as ulcerative colitis or Crohn's disease. In this murine model of IBD, DSS treated TLR3 knock-out mice did not lose substantial weight (FIG. 8) and developed milder epithelial cell damage as assessed by histopathological analysis relative to DSS treated wild type mice. These results indicated that TLR3 signaling can play a crucial role in inflammatory processes such as those involved in IBD.

In these experiments, female wild-type C57BL/6 mice or TLR3 knock-out mice (Alexopoulou et al., *Nature*, 413:732-738 (2001)) were each given 5% (w/v) dextran sulfate sodium (DSS) in the drinking water or unsupplemented water ad libitum as indicated in FIG. 8 for 5 days to induce acute ulcerative colitis. All mice were 6-8 weeks old and each treatment group had at least 5 mice. Development of colitis after DSS treatment was assessed by observing changes in body weight (FIG. 8), colon weight, stool consistency, rectal bleeding, and colon histopathology. All such assessments were conducted in accordance with Institutional Animal Care and Use Committee (IACUC) guidelines. Data in FIG. 8 are shown as percent weight change from treatment days 1 to 5. Each symbol represents data from one mouse. WT designates wild-type mice; KO designates TLR3 knockout mice. Horizontal bars indicate means. Data shown is a composite of three independent experiments. Control wild type and TLR3 knockout mice that did not receive DSS (FIG. 8) showed similar changes in weight (P=0.6, t-test). Wild type and TLR3 knockout mice that did receive DSS (FIG. 8) showed significantly different changes in weight (P=0.003, t-test).

Colons for histopathological analyses were harvested from animals at day 5 of the experiment. Colons were embedded in paraffin, sectioned and stained with hematoxylin and eosin using standard methods. Representative colon sections from wild type mice receiving DSS exhibited mucosal ulceration and dense inflammatory infiltrates as well as crypt and goblet cell loss. Representative colon sections from TLR3 knockout mice receiving unsupplemented water had a morphology and histology similar to that observed in colons of wild-type mice receiving unsupplemented water. Representative colons from TLR3 knockout mice receiving DSS included some dense cell infiltrates, but otherwise exhibited intact mucosal epithelium and minimal loss of goblet cells. This histopathological data indicates that TLR3 knockout mice receiving DSS developed less epithelial ulceration than wild-type mice receiving DSS and reveal that TLR3 activity can play a crucial role in inflammatory processes, such as those involved in IBD.

Figure 9:
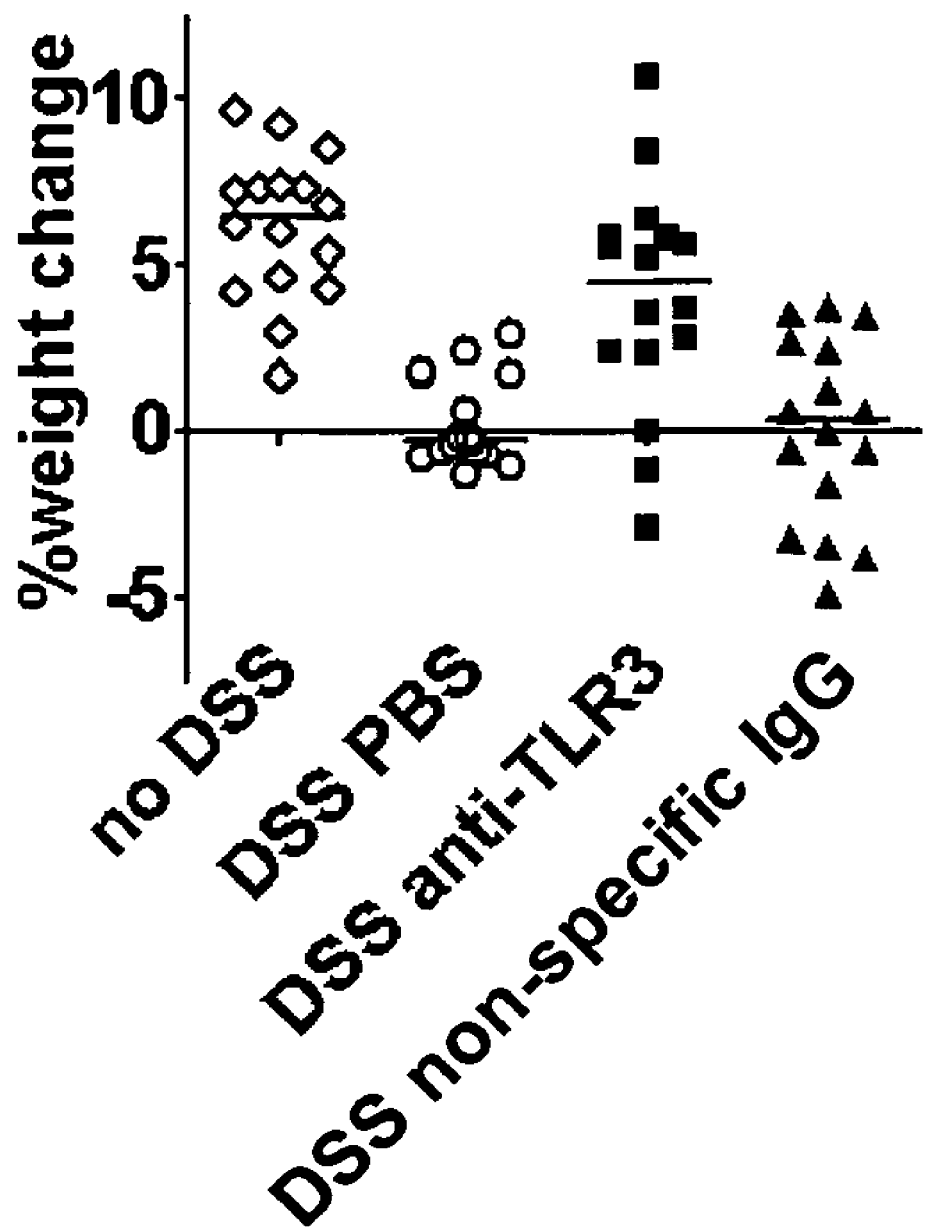
FIG. 9 shows inhibition of IBD-associated weight loss by a TLR3 antagonist.

Example 5 hTLR3 Antagonist Treatment Stops Inflammatory Bowel Disease Associated Weight Loss hTLR3 antagonist treatment decreases the severity of inflammatory bowel disease (IBD) associated weight loss in a murine model of IBD (FIG. 9). The data reveal that treatment with a TLR3 antagonist may attenuate symptoms associated with IBD such as ulcerative colitis and Crohn's disease. Additionally, this result further indicates that TLR3 signaling can play an important role in inflammatory conditions such as IBD.

In these experiments, female wild-type C57BL/6 mice were each given 5% (w/v) dextran sulfate sodium (DSS) in the drinking water or unsupplemented water ad libitum as indicated in FIG. 9 for 5 days to induce acute ulcerative colitis. 0.2 mg of mAb 1068 in PBS carrier, 0.2 mg of a non-specific mouse IgG polyclonal antibody preparation in PBS carrier, or PBS carrier alone were administered by intraperitoneal injection to mice each day for the first 4 days of DSS treatment as indicated in FIG. 9. Each injection comprised 0.9 ml of mAb or non-specific IgG preparation in PBS or 0.9 ml of PBS carrier alone. All mice were 6-8 weeks old and each treatment group contained at least 5 mice. Development of colitis after DSS treatment was assessed by observing changes in body weight (FIG. 9), colon weight, stool consistency, rectal bleeding and colon immunohistopathology. All such assessments were conducted in accordance with established animal care and use guidelines.

Data in FIG. 9 are shown as percent weight change from treatment days 1 to 4. Each symbol represents data from one mouse. Horizontal bars indicate median values. Data shown is a composite of two independent experiments. There was no significant difference in weight change between mice receiving DSS and mAb 1068 and mice that received no DSS (P>0.05, Dunn's test; FIG. 9). Weight change in mice receiving DSS and mAb 1068 was significantly different from the weight change observed in mice receiving DSS and non-specific IgG in PBS or PBS alone (P<0.01 for both; Dunn's test; FIG. 9).

Example 6

Decreased Severity of Chronic Colitis in TLR3 Knockout Mice or hTLR3 Antagonist Treated Mice Six to eight-week old female wild-type C57BL/6 mice and TLR3 knockout (KO) mice on a C57BL/6 background (Alexopoulou et al., *Nature* 413:732-738, (2001)) were used in all studies. Mice were given a total of three cycles of 2% (wt/vol) dextran sulfate sodium (DSS) in the drinking water (Okayasu et al., *Gastroenterology* 98:694-702 (1990)). DSS water was given ad libitum for 5 days to induce ulcerative colitis and then plain drinking water was given for 9 days. A second 5-day cycle of 2% DSS was begun on Day 14, which was followed by a 9-day rest. A third cycle of 2% DSS, this time for 7 days, was begun on Day 28. Mice were sacrificed at two different time points: either after the second rest period on Day 25 of the study, or after the third DSS cycle on Day 37 of the study. Each treatment group consisted of at least 8 mice. Development of colitis was assessed by observing changes in body weight throughout the study, as well as other evaluating other parameters upon sacrifice including colon length, colon weight, stool consistency, rectal bleeding, and colon histopathology after DSS treatment.

Histopathology was assessed by an independent veterinary pathologist blinded to the study design. Longitudinal sections of the colon were scored for a panel of changes including epithelial cell necrosis, epithelial ulceration and sloughing, crypt loss, cryptal cell proliferation, granulation tissue formation in the lamina propria, granulation tissue in the submucosa, submucosal inflammatory cell infiltrate and submucosal edema. Scores were given reflecting the extension of the lesions as follows: 0, non-existent; 1, mild, focal; 2, mild, multifocal; 3, moderate, frequently found but in limited areas; 4, severe, frequently found in many areas of the tissue submitted; 5, very severe, extends to large portions of the tissue submitted. Statistical analyses were performed using Student's t tests (JMP, SAS Institute; GraphPad Prism). The symptoms in patients with ulcerative colitis and Crohn's disease include weight loss, presence of blood in the stool, and ulceration of the epithelial layer in the colon. Thus, the symptoms induced in dextran sulfate sodium-treated mice partially mimic the symptoms seen in patients with ulcerative colitis or Crohn's disease (Hendrickson et al., *Clin. Microbiol. Rev.* 15:79-94 (2002)).

Each cycle of ingestion of DSS induces body weight loss in this model, in both wild type and TLR3 KO mice. However, TLR3 KO mice experienced significantly less weight loss than did wild type mice. TLR3 KO mice also showed decreased disease severity as assessed by gross measures of colonic inflammation and damage: colon shortening in TLR3 KO mice was significantly less than that observed in WT mice and TLR3 KO mice showed a much lower frequency of rectal bleeding. Histopathological assessments of colonic mucosal damage were consistent with these gross measures. Median scores for single cell necrosis, epithelial ulceration, epithelial sloughing, cryptal dropout and crypt abcesses were lower for TLR3 KO mice than WT mice. These data taken together show that absence of TLR3 signaling confers partial protection from disease in a mouse model of chronic colitis, and suggest that TLR3 signaling is likely to exacerbate disease severity in human IBD.

Figure 35:
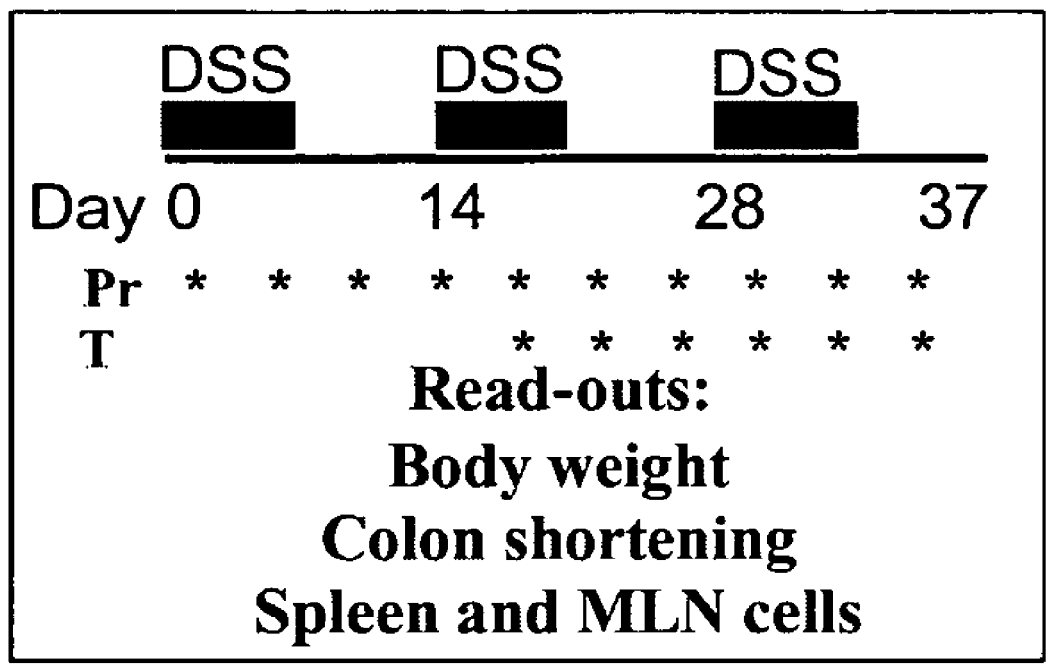
FIG. 35 shows an experimental protocol for prophylactic (Pr) and therapeutic (T) treatment with a TLR3 antagonist during induction of chronic DSS colitis.

To further demonstrate a role for TLR3 in disease modulation, WT C57BL/6 mice were treated with antagonist anti-TLR3 mAb 1068. Groups of DSS-exposed mice received 0.2 mg anti-TLR3 mAb 1068 either prophylactically (starting with the first DSS cycle, "Pr") or "therapeutically" (starting with the second DSS cycle, "Th"; FIG. 35). Control groups of DSS-exposed mice received either PBS (vehicle control) or 0.2 mg of a non-specific negative control mAb. An additional control group was not given DSS. The asterisks in FIG. 35 represent the time points of anti-TLR3 antagonist mAb dosing.

Figure 36:
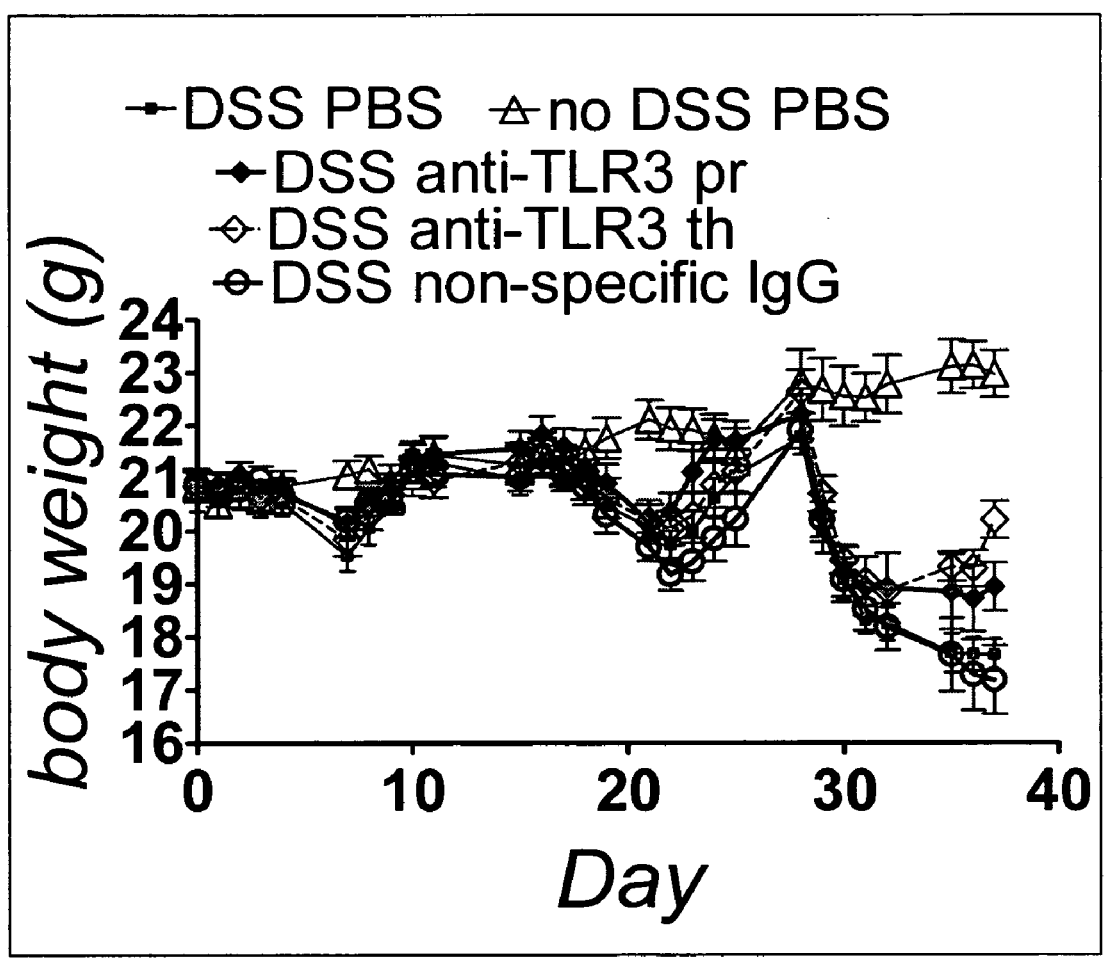
FIG. 36 shows protection by a TLR3 antagonist of weight loss occurring with each cycle of DSS ingestion.
Figure 37:
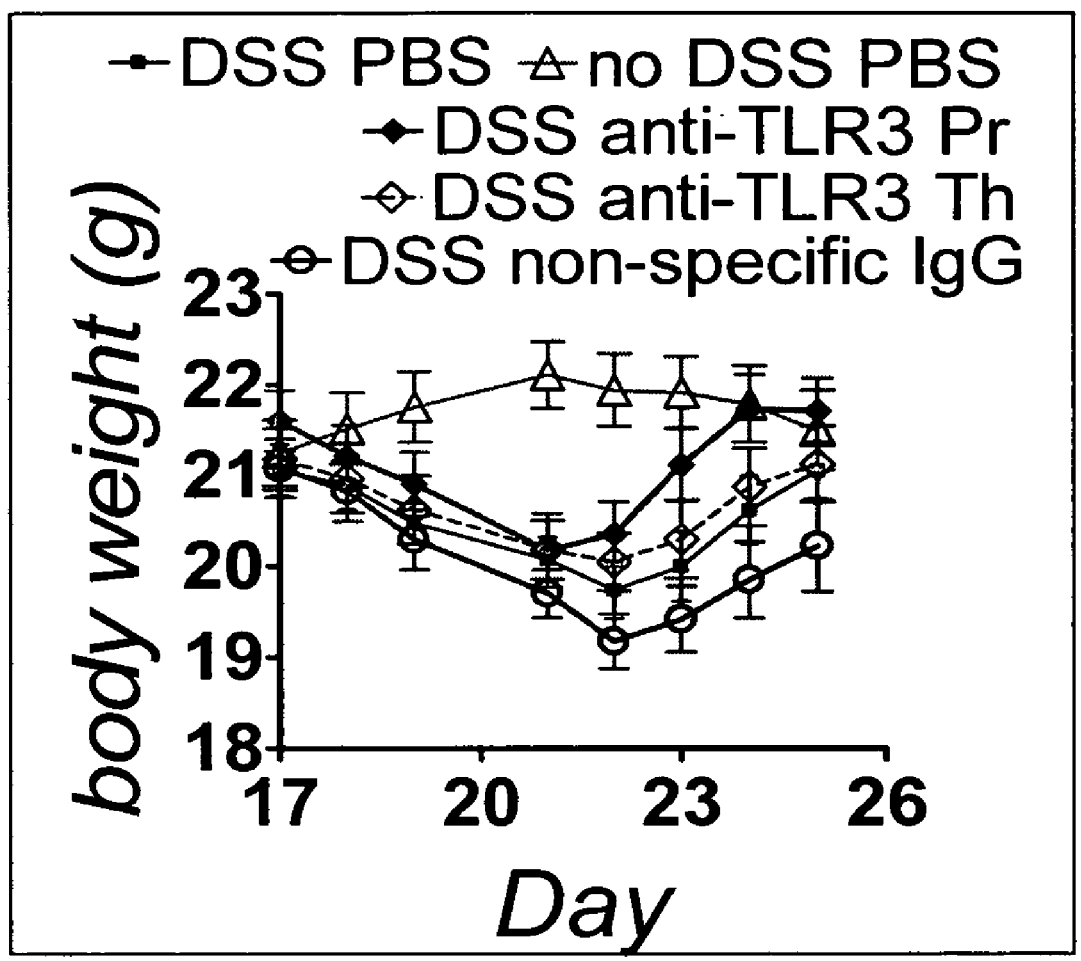
FIG. 37 shows body weight loss and recovery with a TLR3 antagonist after a second DSS cycle.
Figure 38:
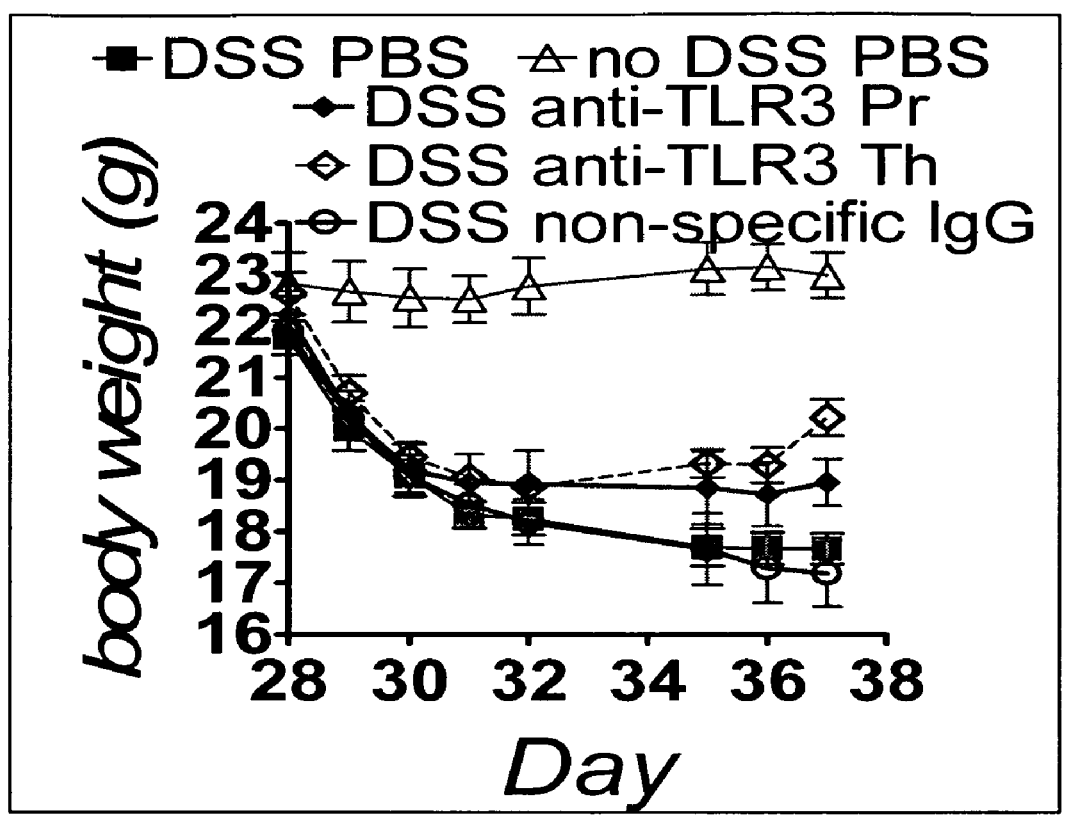
FIG. 38 shows body weight loss and recovery with a TLR3 antagonist after a third DSS cycle.
Figure 39:
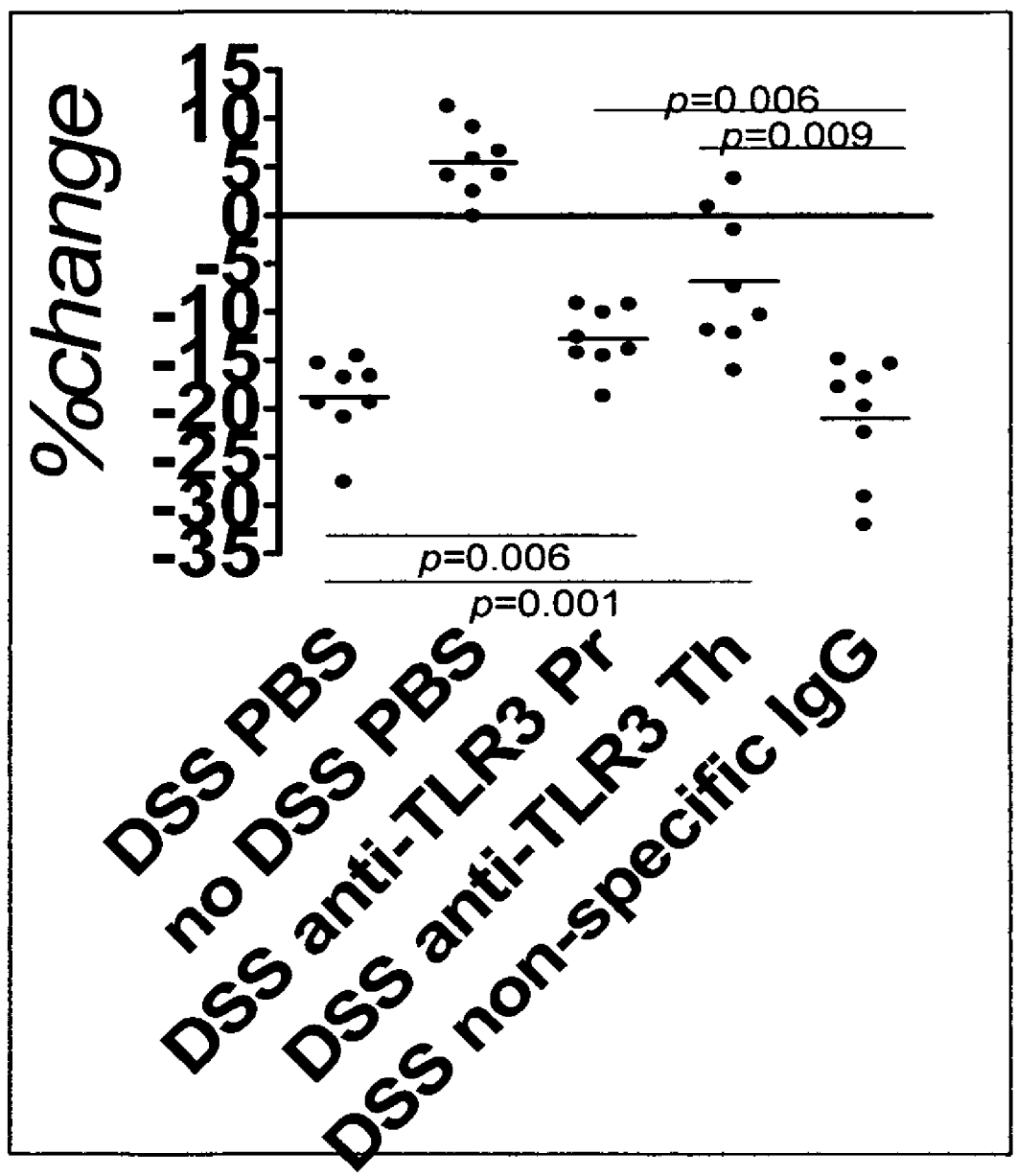
FIG. 39 shows the effect of TLR3 antagonist treatment on net body weight loss associated with chronic DSS colitis.

Each cycle of DSS ingestion was followed by weight loss in all groups of DSS-exposed mice (FIG. 36). Each symbol in FIG. 36 represents the mean of at least eight mice, error bars represent standard deviations. DSS was given from days 0 to 4, 14 to 18 and 28 to 35. However, groups treated with the anti-TLR3 mAb showed reduced weight loss and a faster rate of weight recovery after the $2^{nd}$ DSS cycle compared with groups treated with PBS or the control mAb (FIG. 37). Weight loss after the $3^{rd}$ DSS cycle was also greatly reduced in the anti-TLR3 mAb-treated groups (FIG. 38). Mean net body weight loss from the beginning of the study (Day 0) to the end of the study (Day 37) was roughly 20% in DSS-exposed mice that received either PBS or control mAb. Treatment with anti-TLR3 mAb significantly reduced weight loss to roughly 10% (FIG. 39). In FIG. 39, data is shown as % change in body weight from the start of the study (Day 0) to the end of the study (Day 37) so that positive numbers show net gain and negative numbers show net loss. % Body weight loss in anti-TLR3 mAb treated groups were significantly less than in groups treated with vehicle control (PBS) or non-specific IgG (prophylactic anti-TLR3 treatment (anti-TLR3 P) vs. PBS, P=0.006; anti-TLR3 P vs. non-specific IgG, P=0.006); therapeutic anti-TLR3 (anti-TLR3 Th) vs. PBS, P=0.001; anti-TLR3 Th vs. non-specific IgG, P=0.009). Each symbol represents one mouse; horizontal bars represent means.

Figure 40:
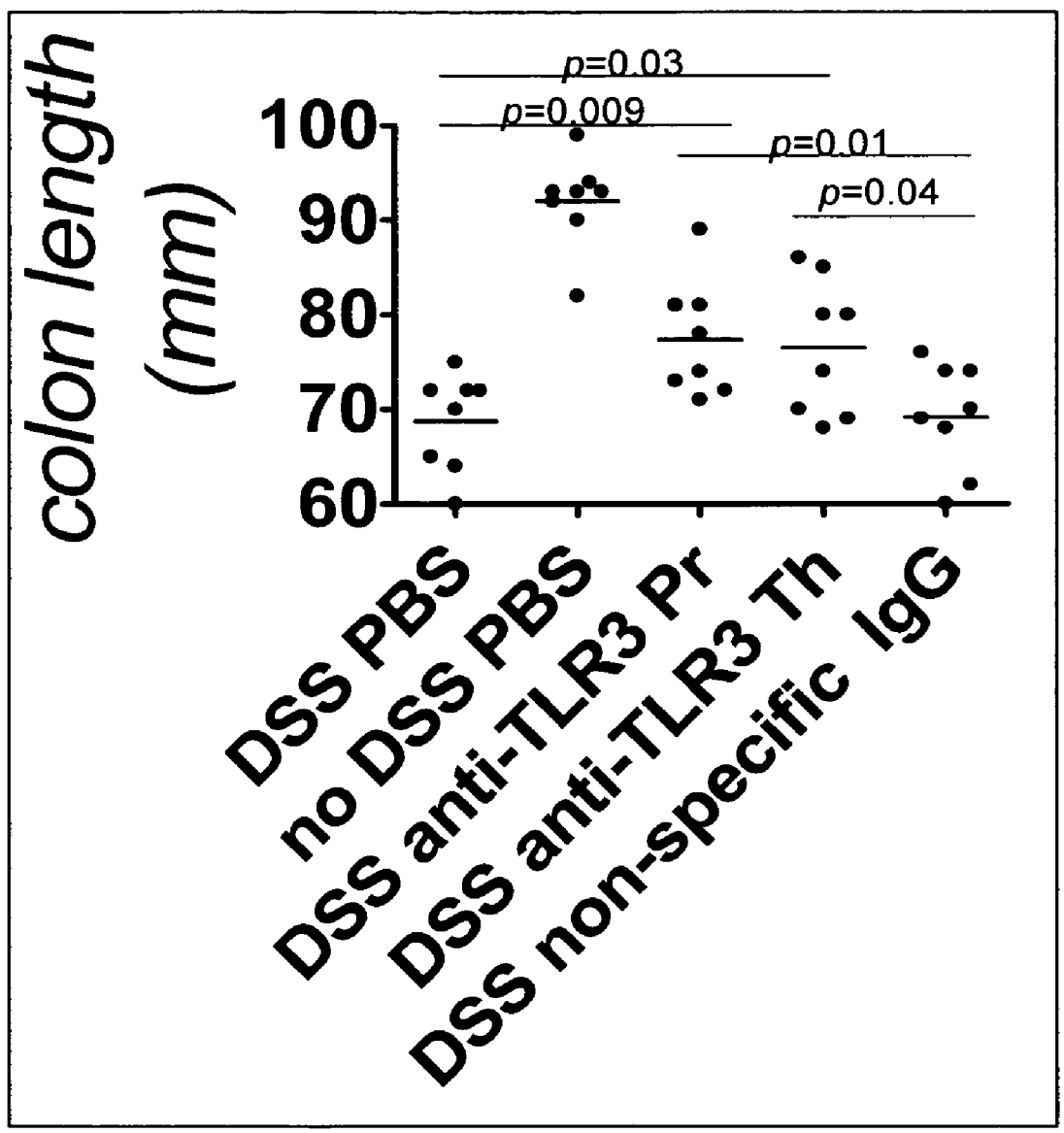
FIG. 40 shows the effect of TLR3 antagonist treatment on colon shortening associated with chronic DSS colitis.
Figure 41A:
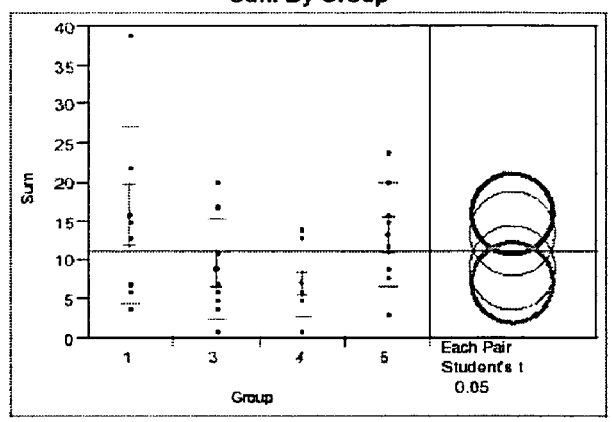
FIGS. 41 A-F show the effect of TLR3 antagonist treatment on the severity of chronic DSS colitis (41A-C) and the histopathological effects of hTLR3 antagonist treatment in chronic DSS colitis (41D-F).
Figure 41B:
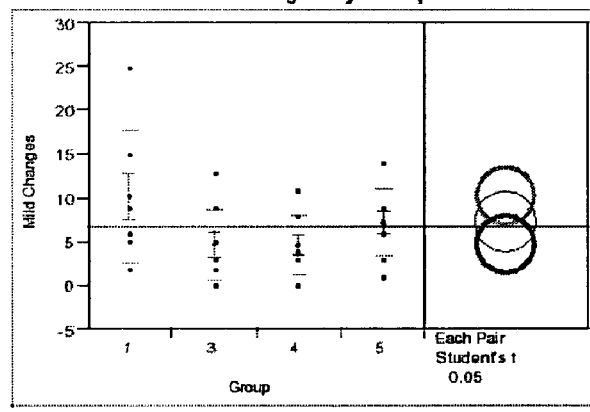
Figure 41C:
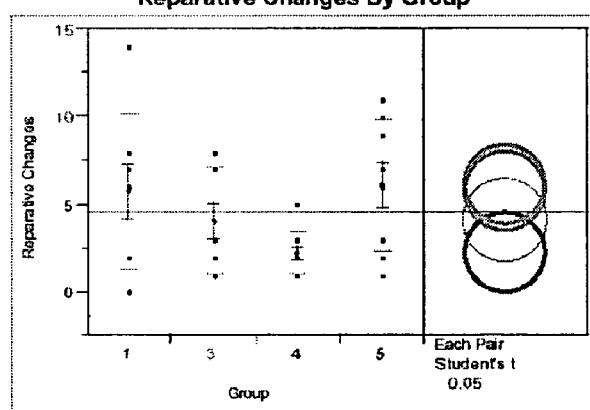
Figure 41D:
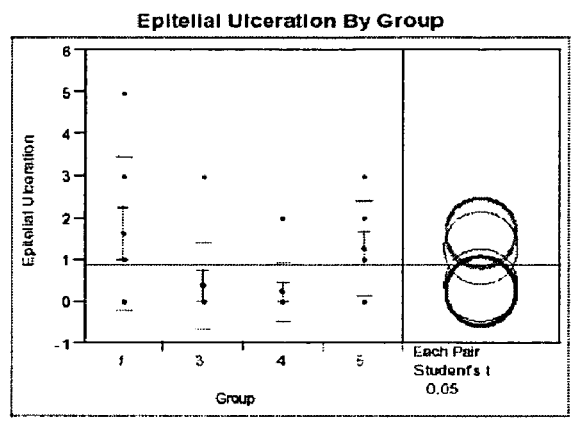
Figure 41E:
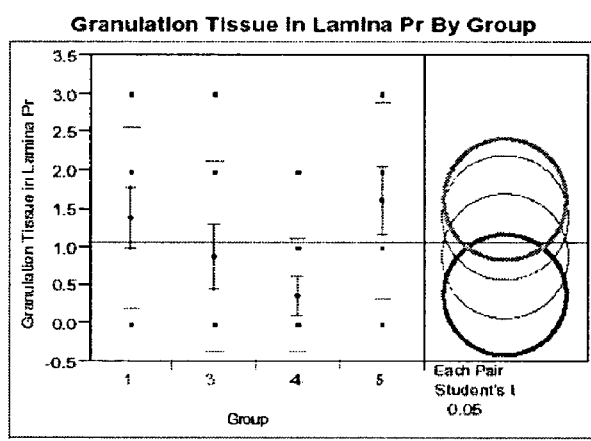
Figure 41F:
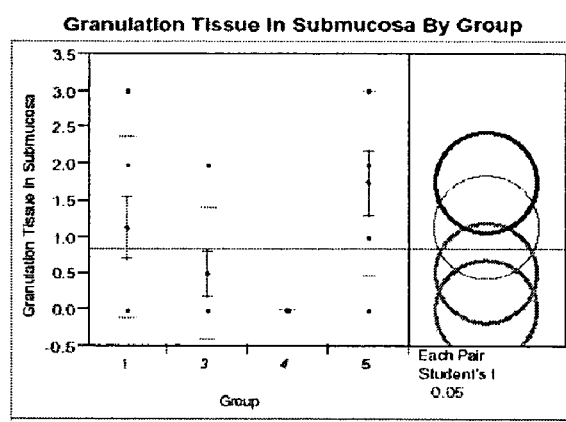

Anti-TLR3 mAb treatment also reduced the extent of colon shortening. Colon lengths in groups of mice treated with anti-TLR3 mAb either prophylactically or therapeutically were significantly greater than those of groups given vehicle or control mAb (FIG. 40). (Anti-TLR3 P vs. PBS, P=0.009; anti-TLR3 P vs. non-specific IgG, P=0.01; anti-TLR3 Th vs. PBS, P=0.03; anti-TLR3 Th vs. non-specific IgG, P=0.04).

Furthermore, colonic mucosal damage was significantly less severe in the group therapeutically treated with anti-TLR3 mAb compared to the control groups given PBS or nonspecific control mAb as assessed by mild histopathological changes (including epithelial cell necrosis, cryptal dropout, epithelial ulceration and sloughing, crypt loss and cryptal cell proliferation) and chronic reparative histopathological changes (including granulation tissue formation in the lamina propria, granulation tissue in the submucosa, submucosal inflammatory cell infiltrate and submucosal edema; FIG. 41$a$). Data shown in graphs represent sums for all histopathological scores, sums for mild changes, or sums for chronic changes for each group of mice that received DSS and different treatments (Groups: 1, PBS vehicle-treated; 3, prophylactic anti-TLR3 mAb; 4, therapeutic anti-TLR3 mAb; 5, non-specific control mAb). The circles on the right panel of each graph enclose the means and standard deviations of scores for each treatment group. Statistically significant differences between groups are represented as circles with minimal overlap.

In particular, anti-TLR3 mAb treatment reduced epithelial ulceration and prevented the formation of granulation tissue in the submusoca and lamina propria compred to PBS or non-specific mAb (FIG. 41$b$). Data shown in graphs represent histopathological scores for each group of mice that received DSS and different treatments (Groups: 1, PBS vehicle-treated; 3, prophylactic anti-TLR3 mAb; 4, therapeutic anti-TLR3 mAb; 5, non-specific control mAb). The circles on the right panel of each graph enclose the means and standard deviations of scores for each treatment group. Statistically significant differences between groups are represented as circles with minimal overlap.

Figure 42:
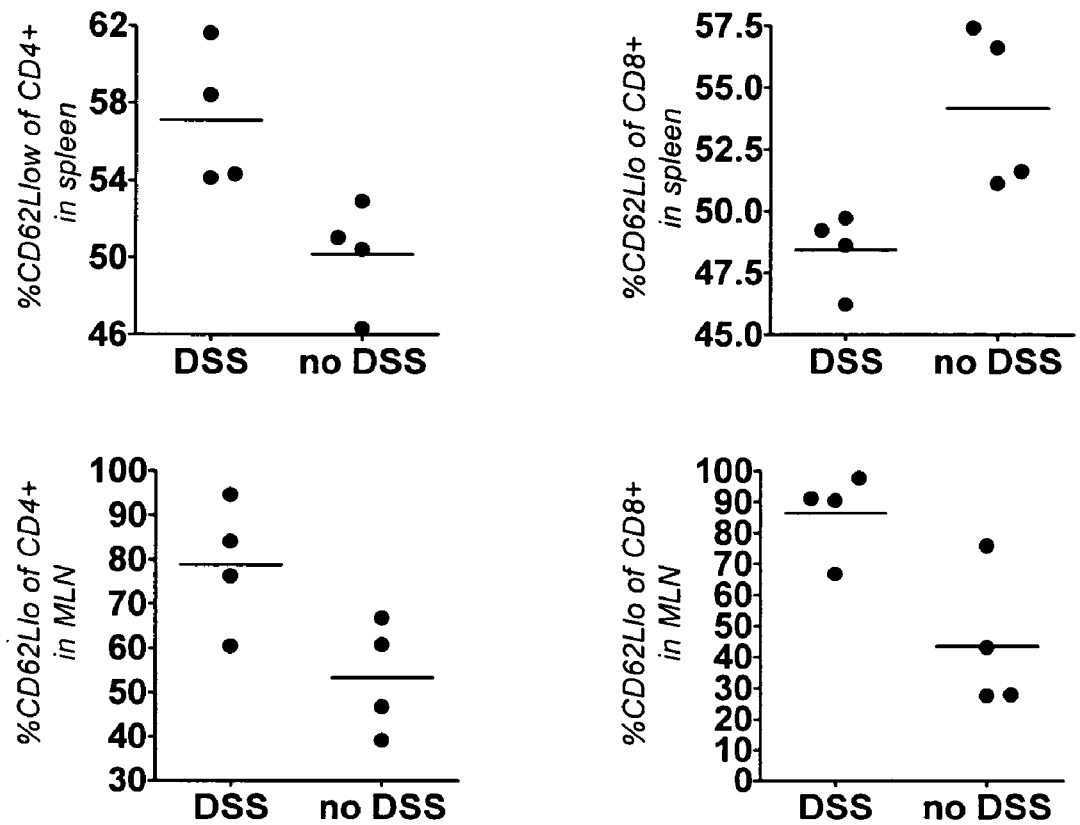
FIG. 42 shows T-cell activation in chronic DSS colitis.

To determine potential immune correlates of anti-TLR3-conferred protection, immune cell populations and systemic cytokine levels were examined. It was observed that DSS exposure was associated with increases in the numbers of activated T cells in the spleen and mesenteric lymph nodes (FIG. 42), consistent with published reports demonstrating T cell involvement in this chronic colitis model. Flow cytometry was used to measure the frequencies of CD62L$^{low}$ T cells in the spleen and mesenteric lymph nodes, representing systemic and regional T cell activation respectively. Chronic colitis was associated with increased frequencies of activated CD4+ (helper) T cells in the spleen and mesenteric lymph nodes, suggesting an overall increase in helper T cell activation. Decreased frequencies of activated CD8+ effector T cells in the spleen were accompanied by increased frequencies of activated CD8+ T cells in the mesenteric lymph nodes, suggesting trafficking of effector T cells to the gut locale. Data are shown from Day 25, following $2^{nd}$ DSS cycle. Each symbol represents data from one mouse; horizontal bars indicate means.

Figure 43:
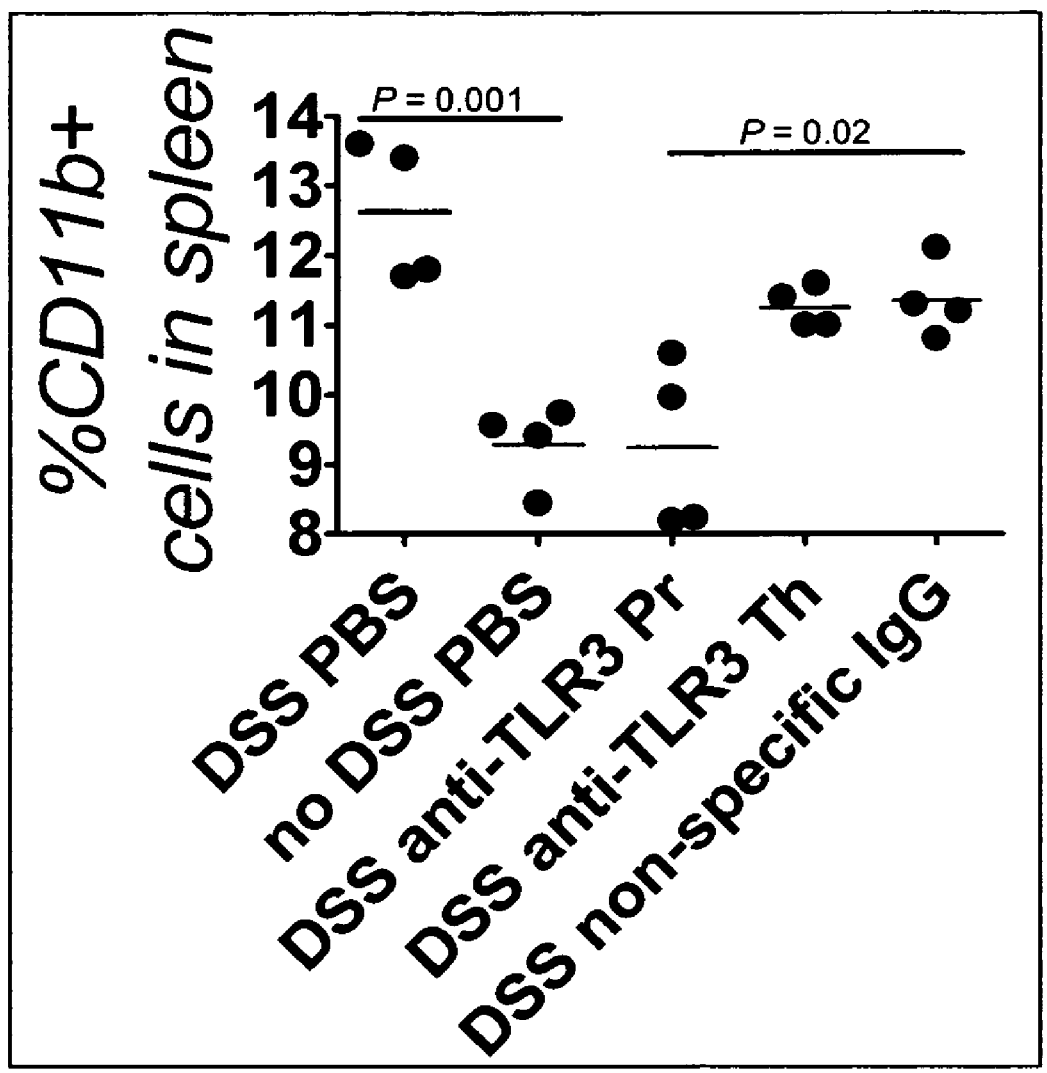
FIG. 43 shows the effect of prophylactic TLR3 antagonist treatment on DSS-associated increase of CD11b+ cells in spleen.

In addition, greater frequencies of CD11b+ cells were found in the spleens of DSS-exposed mice, possibly reflecting a colitis-associated increase in inflammatory macrophages. Strikingly, prophylactic anti-TLR3 mAb treatment was associated with significantly reduced frequencies of splenic CD11b+ cells, down to levels seen in control mice not exposed to DSS (FIG. 43). Percentages of CD11b+ cells in the spleens of DSS-exposed anti-TLR3 mAb-treated mice were similar to mice that did not receive DSS and were significantly lower than those of DSS-exposed mice that received either PBS (P=0.001) or non-specific IgG (P=0.02). Data are shown from Day 25, following $2^{nd}$ DSS cycle. Each symbol represents data from one mouse; horizontal bars indicate means.

Figure 44:
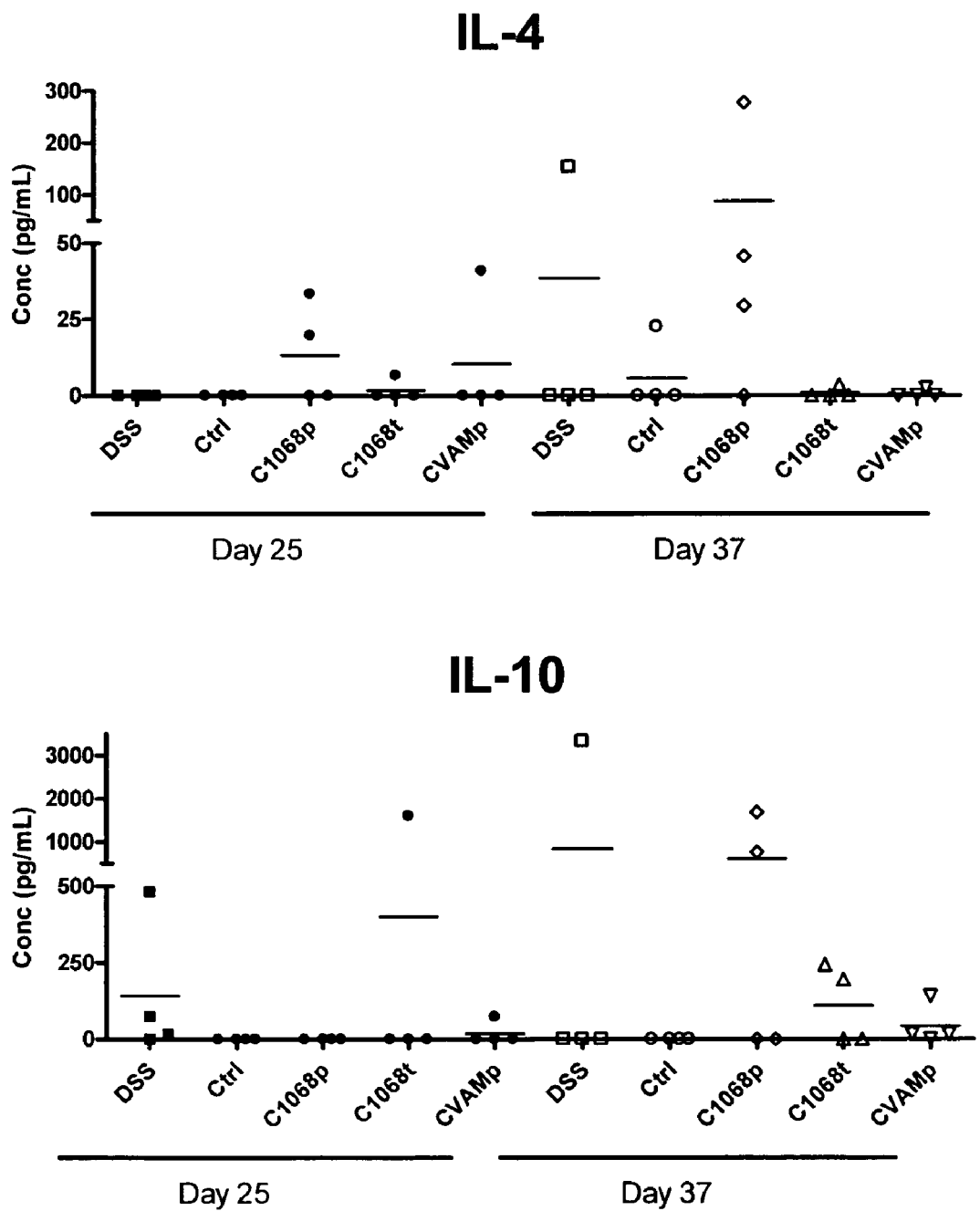
FIG. 44 shows the effect of TLR3 antagonist treatment on systemic levels of IL-4 and IL-10 in chronic DSS colitis.

Serum cytokine profiles of DSS-exposed mice also show alterations associated with anti-TLR3 mAb treatment: increased IL-4 and IL-10 levels were measured in mice that received anti-TLR3 mAb prophylactically (FIG. 44). Anti-TLR3 mAb treatment during induction of chronic DSS colitis enhanced systemic IL-4 and IL-10 levels. Data from Day 25 and 37 are shown representing time points after $2^{nd}$ and $3^{rd}$ DSS cycles respectively. Each symbol represents data from one mouse; horizontal bars indicate means. IL-4 and IL-10 have both been demonstrated to play key roles in the regulation of inflammation. A specific role for IL-10 in controlling immunopathogenesis in IBD is suggested by the observation that IL-10 knock-out mice spontaneously develop colitis. These results suggest that anti-TLR3 mAb treatment alters the inflammatory and T cell responses induced by DSS ingestion.

Taken together, these data demonstrate that blockade of TLR3 signaling with anti-TLR3 mAbs can ameliorate disease severity in a chronic colitis model and provide evidence for the potential efficacy of anti-TLR3 mAbs for the treatment of human IBD.

Example 7 hTLR3 Antagonist Treatment Increases Sepsis Survival

Sepsis can be modeled in animals, such as mice, by the adminstration of D-galactosamine and poly(I:C). In such models, D-galactosamine is a hepatotoxin which functions as a sepsis "sensitizer" and poly(I:C) is a sepsis-inducing molecule that mimics dsRNA and activates TLR3. The results indicated that TLR3 antagonist treatment can nearly double the animal survival rate in a murine model of sepsis.

Figure 10:
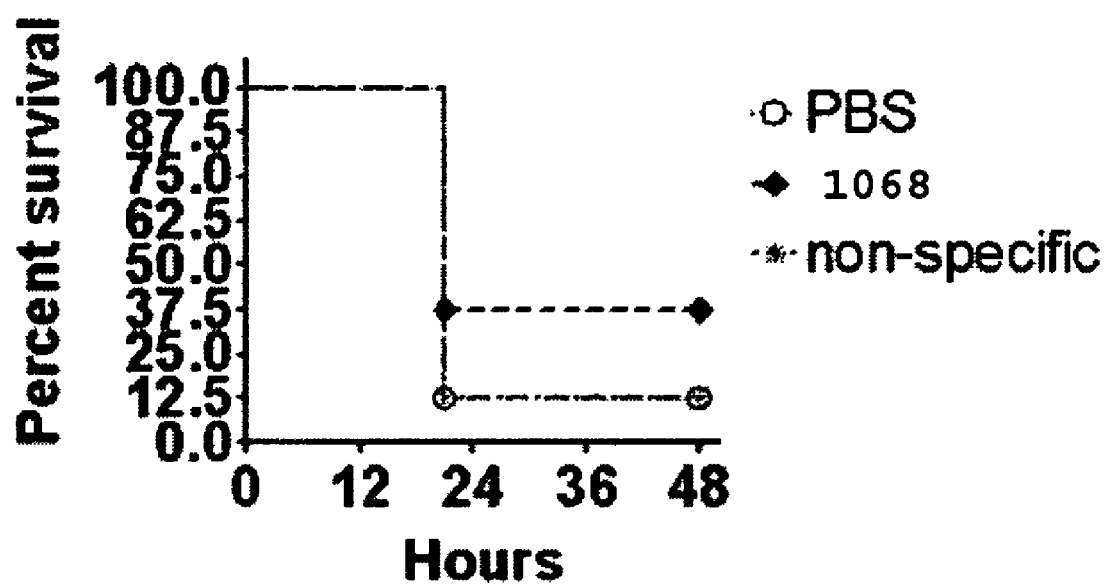
FIG. 10 shows increased survival in a murine sepsis model through treatment with a TLR3 antagonist.

In these experiments, female wild-type C57BL/6 mice were given intraperitoneal injections of either 1 mg of the hTLR3 antagonist 1068 mAb in PBS carrier, 1 mg of a non-specific murine polyclonal IgG preparation in PBS carrier, or PBS carrier alone as indicated in FIG. 10. Each injection comprised 1 ml of mAb or non-specific IgG preparation in PBS or 1 ml of PBS carrier alone. The following day mice received 10 µg poly(I:C) and 20 mg D-galactosamine (Sigma-Aldrich Corp., St. Louis, Mo.) in 100 µl of sterile PBS by intraperitoneal injection as indicated in FIG. 10. Survival of the mice was monitored twice daily for 3 days. All assessments were conducted in accordance with established animal care and use guidelines. The results show that hTLR3 antagonist treatment increases the animal survival rate in a murine model of sepsis (FIG. 10).

Example 8 hTLR3 Antagonist Treatment Decreases IL-6 and TNF-alpha Cytokine Production in a Murine Model of Sepsis hTLR3 antagonist treatment decreases serum levels of the inflammation associated IL-6 (FIG. 11) and TNF-alpha (FIG. 12) cytokines in a murine model of sepsis. This result indicates that inhibiting TLR3 activity can promote survival of sepsis by decreasing TLR3 mediated production of cytokines that contribute to sepsis.

Sera from mice treated as described in Example 6 above were prepared by retro-orbital sinus bleeds of $CO_2/O_2$ anesthetized mice two hr after poly(I:C) administration. Sera were prepared by incubation of blood at room temperature, followed by centrifugation at 2500 rpm for 15 min. Sera were stored at −80° C. prior to cytokine assays. Cytokine levels in serum samples were measured using Luminex® instrumentation (Luminex Corp., Austin, Tex.) and IL-6 (FIG. 11) or TNF-alpha (FIG. 12) specific mAb conjugated beads as appropriate. Luminex® assays for each cytokine were performed as directed by the manufacturer. All assessments were conducted in accordance with established animal care and use guidelines.

Figure 11:
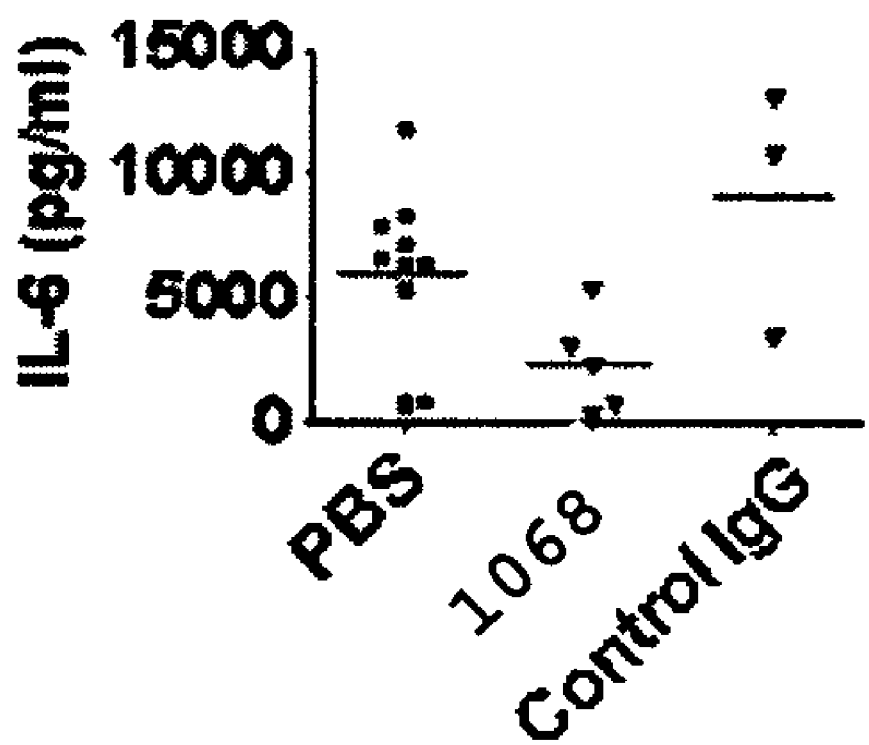
FIG. 11 shows a decrease in IL-6 cytokine production in a murine sepsis model by a TLR3 antagonist.
Figure 12:
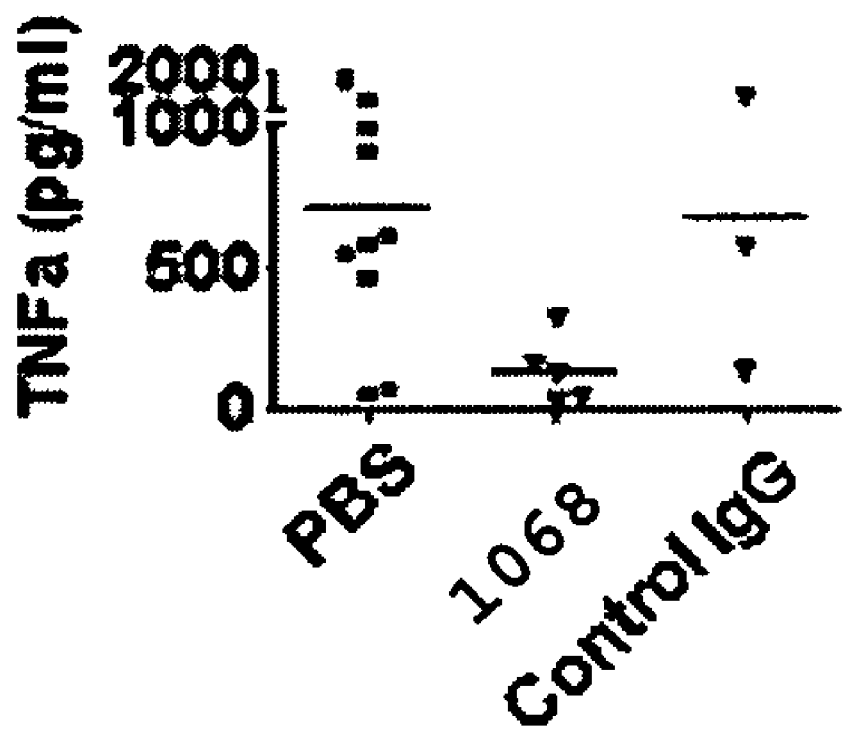
FIG. 12 shows a decrease in TNF-alpha cytokine production in a murine sepsis model by a TLR3 antagonist.

Each symbol in FIG. 11 and FIG. 12 represents data from one mouse. Horizontal bars indicate means. Data shown is a composite of two independent experiments. Treatment with mAb 1068 significantly reduced serum IL-6 levels two hours after poly(I:C) administration (P=0.04, t-test; FIG. 11). Treatment with mAb 1068 significantly reduced serum TNF-alpha levels two hours after poly(I:C) administration (P=0.03, t-test; FIG. 12).

Example 9

Poly I:C Administration Induces Secretion of Pro-Inflammatory Cytokines and Upregulation of TLR Gene Expression in Lungs Isoflurane anesthetized male or female wild-type C57BL/6 mice received three intranasally administered doses of poly (I:C) in PBS or PBS alone every 24 h for three days. All mice were twelve weeks old. Each poly(I:C) dose contained either 50 µg or 100 µg poly(I:C) as indicated in Table 1. The volume of each dose was 50 µL. Each treatment group contained 6-8 mice. Mice were sacrificed by $CO_2$ treatment and the lungs were cannulated 24 h after the last dose. Bronchoalveolar lavages (BAL) were then performed by injecting 1 mL of PBS into the lungs and retrieving the effluent. BAL preparations were then centrifuged to pellet cells and cell-free supernatants were collected and stored at −80° C. until used for multichannel cytokine assays. All assessments were conducted in accordance with established animal care and use guidelines.

Cytokine levels in BAL supernatants were measured using Luminex® multichannel analysis (Luminex Corp., Austin, Tex.) and IFNγ, IL-1α, IL-6, CXCL10, JE, KC, MGCSF, MIP1α, RANTES, TNFα, or GMCSF specific mAb conjugated beads (LINCO Research, St. Charles, Mo.) as appropriate. Luminex® assays for each cytokine were performed as directed by the manufacturer. Data are expressed as mean pg/ml±standard error of the mean (SEM) from 6-8 mice.

The results indicated that multiple administrations of either 50 or 100 µg poly I:C induced elevated protein levels of cytokines, chemokines and growth factors including interferon-γ(IFNγ), interleukin-6 (IL-6), tissue necrosis factor-α (TNFα), chemokine (CXC motif) ligand 10 (CXCL10), chemokine (CC motif) ligand 2 (JE), chemokine KC (KC), Macrophage Inflammatory Protein-1 α(MIP-1α), regulated upon activation, normally T cell expressed and secreted/CCL5 (RANTES), murine Granulocyte Colony Stimulating Factor (mG-CSF) and Granulocyte-macrophage colony-stimulating factor(GM-CSF) (Table 1). This result indicates that TLR3 activation may play an important role in cytokine, chemokine, and growth factor mediated lung pathologies such as COPD.

In addition, Taqman real time PCR analyses of the lung tissues demonstrated that multiple administrations elicited upregulation of cytokine genes as well as the mRNA for multiple TLRs and their associated intracellular signaling molecules (Table 2). These data demonstrate that poly I:C, a synthetic double-stranded RNA analog, administered in vivo elicits a cascade of events resulting in the secretion of multiple proinflammatory cytokines, chemokines and upregulation of TLR gene expression such as TLR2, TLR3, TLR7 and TLR9.

TABLE 1

Multiple administrations of poly(I:C) to the lungs of C57BL/6 mice induces the secretion of cytokines, chemokines, and growth factors into the airways. Data are expressed as mean pg/ml ± standard error of the mean (SEM) from 6-8 mice.

| Secreted Protein | Treatment | | |
|---|---|---|---|
| | PBS | 50 µg poly(I:C) | 100 µg poly(I:C) |
| IFNγ | 10.98 +/− 1.63 | 12.84 +/− 1.72 | 52.23 +/− 11.19 |
| IL-1α | 16.47 +/− 1.24 | 21.99 +/− 1.85 | 21.79 +/− 1.44 |
| IL-6 | 8.80 +/− 1.54 | 237.51 +/− 94.41 | 878.98 +/− 171.17 |
| CXCL10 | 30.27 +/− 5.90 | 309.19 +/− 50.05 | 411.30 +/− 34.88 |
| JE | 11.70 +/− 1.18 | 158.61 +/− 39.40 | 798.69 +/− 182.60 |
| KC | 6.22 +/− 1.28 | 46.55 +/− 11.84 | 55.36 +/− 6.53 |
| mGCSF | 5.23 +/− 0.65 | 34.34 +/− 6.43 | 60.64 +/− 6.78 |
| MIP1α | 37.72 +/− 6.33 | 150.41 +/− 37.45 | 441.14 +/− 61.56 |
| RANTES | 0.48 +/− 0.04 | 18.90 +/− 7.15 | 155.75 +/− 41.59 |
| TNFα | 2.28 +/− 0.33 | 17.01 +/− 4.51 | 81.16 +/− 13.72 |
| GMCSF | 19.10 +/− 2.10 | 27.69 +/− 1.86 | 33.54 +/− 4.48 |

Example 10

TLR3 Activation Increases Cytokine, Chemokine, Growth Factor and Toll Gene Transcript Levels in Lung Tissue Transcript levels in total RNA extracted from the lungs of male or female C57BL/6 mice treated as described in Example 8 above was measured by real time-PCR (RT-PCR). Total RNA was extracted from mouse lung tissue samples using Trizol™ (Invitrogen Corp., Carlsbad, Calif.) and isolated using the RNEasy Mini Kit (Qiagen Inc., Valencia, Calif.). RNA from 6-8 identically treated mice was then pooled.

cDNAs were prepared from each RNA pool using the Omniscript™ kit (Qiagen Inc., Valencia, Calif.) according to the manufacturer's instructions. 100 ng of cDNA was amplified using TaqMan™ Low Density Immune Profiling Array Cards (Applied Biosystems, Foster City, Calif.) or custom Low Density Array (LDA) cards as directed by the manufacturer. Primer Express™ software (Applied Biosystems) was used to design the probe and primer combinations. TaqMan™ RT-PCR (Applied Biosystems) was then performed in a 384 well format using ABI PRISM™ 7000HT instrumentation (Applied Biosystems) as directed by the manufacturer.

Data collection and transcript quanitation in the early exponential phase of PCR was performed with the ABI PRISM™ 7000HT instrumentation and associated software. Individual transcript levels were normalized against transcript levels for 18S ribosomal RNA. Data in Table 2 are expressed as mean fold increase in mRNA transcript levels in mice receiving multiple administrations of poly(I:C) relative to mice treated with PBS vehicle. Data represent pooled RNA from 6-8 mice.

The data indicate that TLR3 activation increases cytokine, chemokine, growth factor and Toll gene transcription (e.g. TLR3 and other Toll-Like Receptors) in murine lung tissues (Table 2). This result further indicates that TLR3 activation and activation of other Toll Like Receptors (TLRs) may play an important role in cytokine, chemokine, and growth factor mediated lung pathologies.

TABLE 2

TLR3 activation by multiple administrations of poly(I:C) to the lungs of C57BL/6 mice increases cytokine, chemokine, growth factor and Toll gene transcript levels. Data are expressed as mean fold increase in mRNA transcript levels in mice receiving multiple administrations of poly(I:C) relative to mice treated with PBS vehicle. Data represent pooled RNA from 6-8 mice.

| Protein Encoded | Treatment | |
|---|---|---|
| by Gene Transcript | 50 μg poly(I:C) | 100 μg poly(I:C) |
| CCL2 | 46.81 | 76.62 |
| CCL3 | 18.04 | 30.49 |
| CCL7 | 22.58 | 48.38 |
| IL-15 | 9.91 | 10.83 |
| IL-16 | 4.74 | 2.31 |
| IL-18 | 3.30 | 3.40 |
| IL-1α | 3.37 | 3.52 |
| IL-1β | 11.96 | 10.86 |
| IL-2rα | 12.17 | 3.97 |
| IL-7 | 4.47 | 1.43 |
| MUC1 | 3.05 | 1.47 |
| PDGFβ | 2.96 | 2.20 |
| SFTPa | 2.32 | 1.19 |
| SFTPb | 2.50 | — |
| SFTPc | 1.89 | — |
| SFTPd | 3.12 | 1.93 |
| TGFβ | 3.05 | 2.40 |
| TNFα | 105.91 | 78.45 |
| Vamp8 | 2.59 | 1.78 |
| CXCL10 | 90.03 | 357.38 |
| IFNαR1 | 2.50 | 2.32 |
| IFNαR2 | 3.64 | 3.01 |
| IFNγR | 2.20 | 1.54 |
| IRAK1 | 2.57 | 1.73 |
| IRAK2 | 2.56 | 2.26 |
| IRAK4 | 2.35 | 1.72 |
| IRF3 | 1.97 | 1.62 |
| IRF7 | 17.03 | 22.92 |
| ISGF3G | 5.63 | 4.45 |
| OAS2 | 5.29 | 10.76 |
| PRKR | 5.49 | 9.32 |
| RNASE 1 | 2.25 | 1.91 |
| SOCS3 | 3.93 | 4.63 |
| TLR2 | 3.72 | 6.96 |
| TLR3 | 3.77 | 5.41 |
| TLR4 | 2.43 | 1.89 |
| TLR7 | 6.26 | 10.86 |
| TLR9 | 21.21 | 55.78 |
| TOLLIP | 2.48 | 1.72 |

Example 11

TLR3 Activation Increases Inflammatory Cell Levels in Lung Tissue

Figure 13:
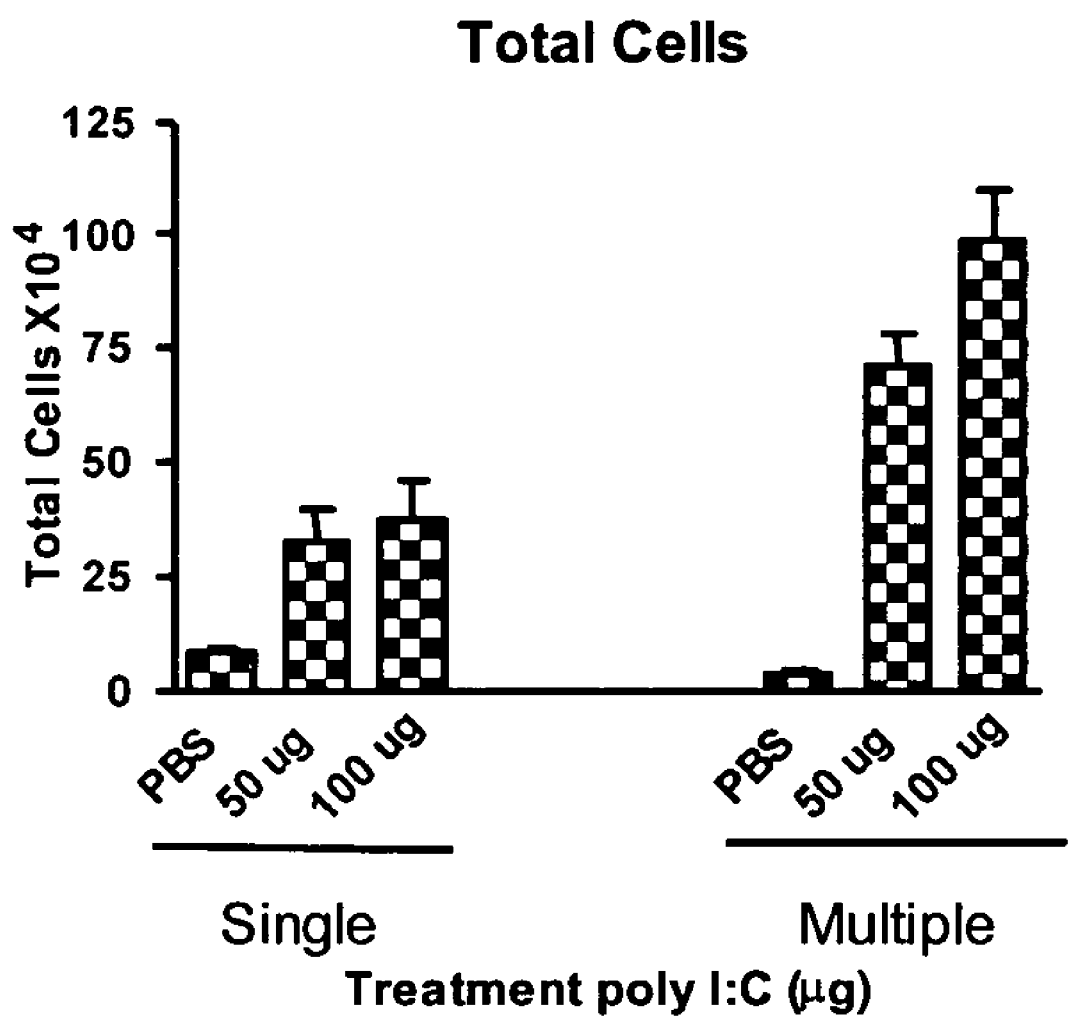
FIG. 13 shows poly(I:C) induced increases in total numbers of inflammatory cells in murine lung tissue.
Figure 14:
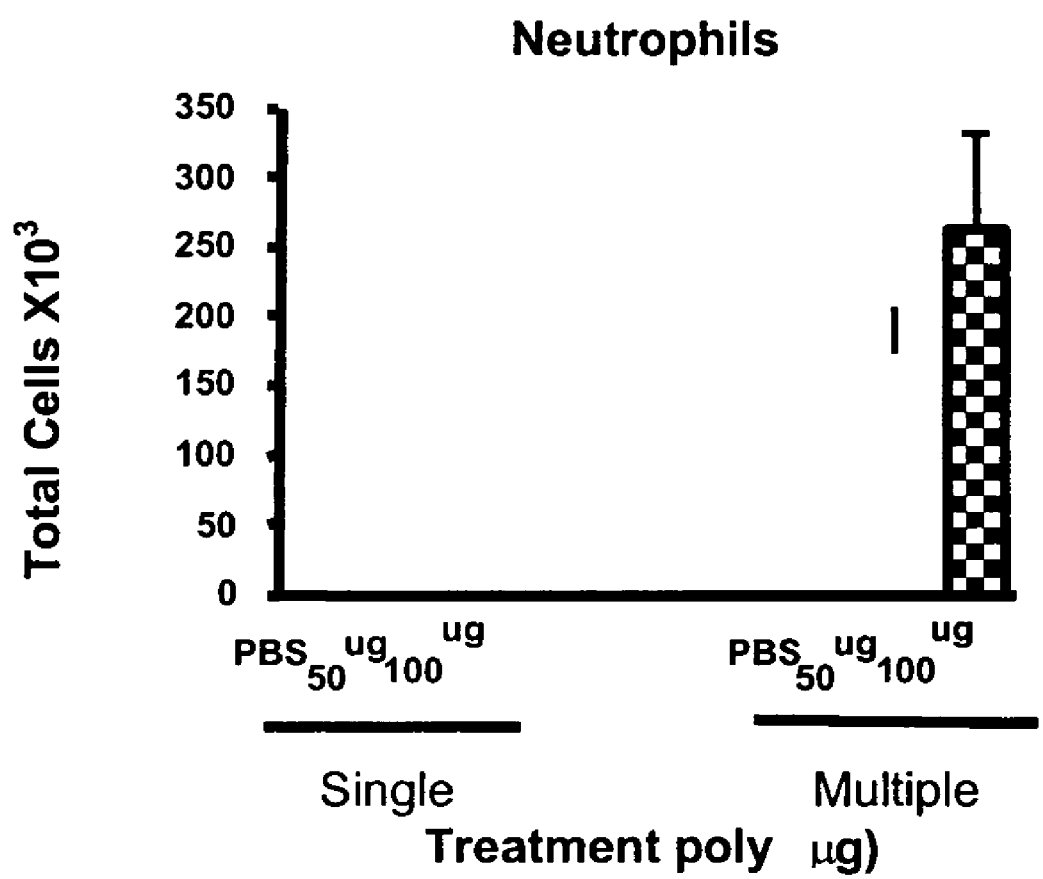
FIG. 14 shows poly(I:C) induced increases in neutrophils in murine lung tissue.
Figure 15:
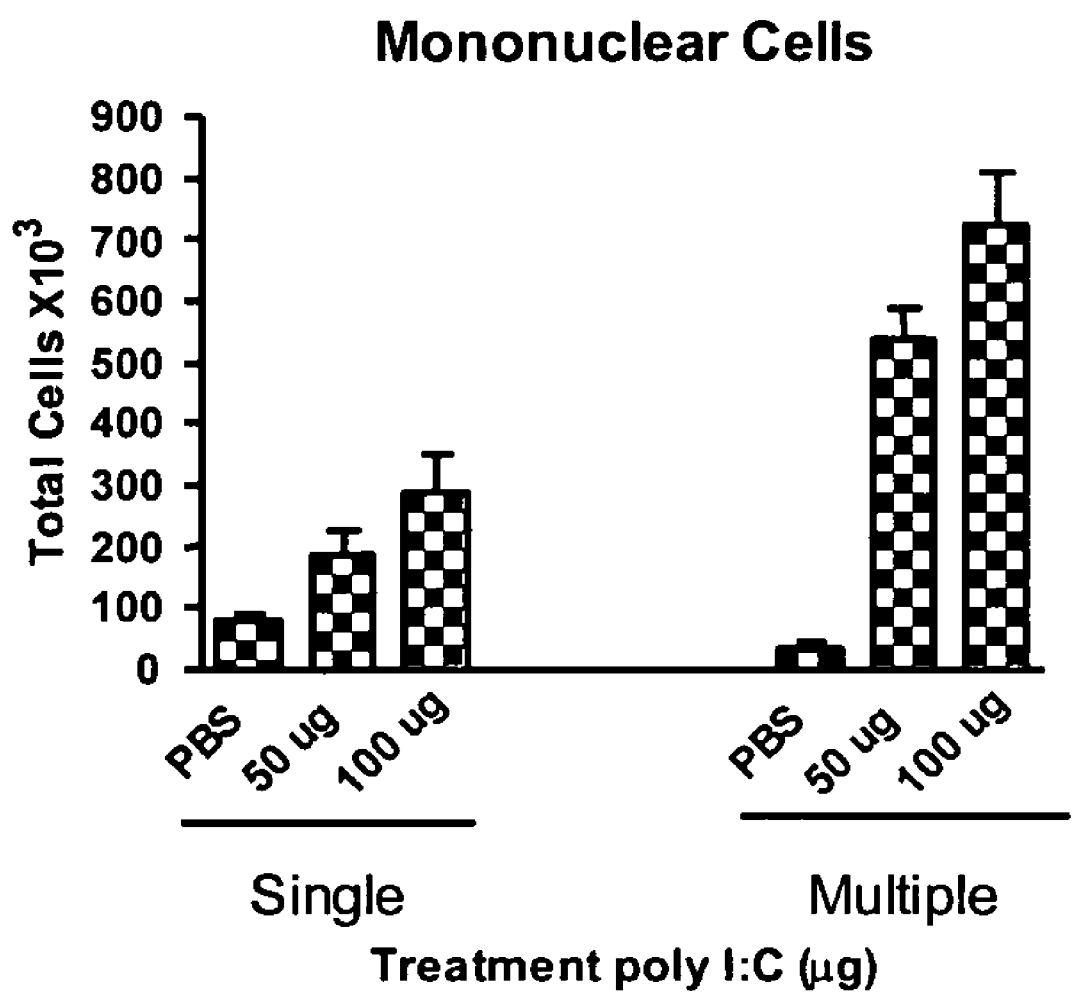
FIG. 15 shows poly(I:C) induced increases in mononuclear inflammatory cells in murine lung tissue.

TLR3 activation increases inflammatory cell levels in murine lung tissues (FIGS. 13, 14, and 15). This result indicates that TLR3 activation may play an important role in lung pathologies associated with increased lung infiltration by inflammatory cells (FIG. 13) such as neutrophils (FIG. 14) and mononuclear cells (FIG. 15) (e.g. monocytes or lymphocytes).

Inflammatory cell infiltration into the lungs of C57BL/6 mice receiving poly(I:C) was assessed by either hemocytometer enumeration (FIG. 13) or differential staining (FIG. 14 and FIG. 15). Mice received multiple poly(I:C) doses as described in Example 9 above or a single poly(I:C) dose. Single poly(I:C) doses were intranasally administered to isoflurane anesthetized male or female C57BL/6 mice. All mice were between eight and twelve weeks old. Single doses comprised 50 μg or 100 μg of poly(I:C) in 50 μL of PBS. BAL to recover lung infiltrating cells were performed 24 h after poly (I:C) administration for animals receiving a single poly(I:C) dose or 24 h after the final poly(I:C) administration for animals receiving multiple doses. BAL was performed as described in Example 8 above.

Cell pellets recovered after BAL on treated mouse lungs were resuspended in 200 μL of Dulbecco's Phosphate Buffered Saline (DPBS) containing 0.1% BSA. A 50 μL aliquot of the suspended cells was then added to 50 μL Turk's Blood diluting fluid (Red Bird Service, Osgood, Ind.), mixed thoroughly, and the total cell number was enumerated by hemocytometer counting (FIG. 13). A 100 μL aliquot of a suspension containing less than $1 \times 10^5$ cells/μL was then loaded onto a Cytospin™ slide assembly, and spun for 4 minutes at 400 rpm. Slides were removed from Cytospin™ assemblies and allowed to dry for at least one hour. Slides were then submersed in Wright-Giemsa stain for 90 seconds and destained in ddH$_2$O for 5 minutes. Slides were allowed to dry overnight. Under oil immersion using a 100× objective, slides were differentially counted and the total number of neutrophils (FIG. 14) and mononuclear cells (FIG. 15) were counted. The mean and SEM for lung infiltrating cell data collected from 6-8 mice from each treatment group were then plotted (FIGS. 13, 14, and 15).

Example 12

TLR3 Knockout Animals Are Protected from Poly(I:C) Induced Inflammatory Cell Level Increases in the Lung Tissues Inflammatory cell infiltration into the lungs of C57BL/6 or TLR3 knockout mice or receiving single or multiple poly(I:C) administrations was assessed by hemocytometer enumeration and differential staining to identify neutrophils and mononuclear cells. Mice received multiple poly(I:C) doses as described in Example 8 or a single poly(I:C) dose as described in Example 10. BAL to recover lung infiltrating cells was performed 24 h after poly(I:C) administration for animals receiving a single poly(I:C) dose or 24 h after the final poly(I:C) administration for animals receiving multiple doses. BAL was performed as described in Example 8 above. Assessment of inflammatory cell infiltration into the lungs of wild-type C57BL/6 or TLR3 knockout mice was by either hemocytometer enumeration or differential staining as described in Example 10. Data were expressed as fold increase in the mean lung infiltrating cell count in poly(I:C) treated animals relative to the mean lung infiltrating cell count in animals receiving PBS alone. Data represent values obtained from 6 mice.

The results shown in Table 3 indicate that TLR3 knockout mice are protected from poly(I:C) induced inflammatory cell level increases in the lung tissues relative to wild-type mice and that the effects of poly(I:C) administration are largely due to TLR3 activation. Further, the results indicate that TLR3 activation may play an important role in lung pathologies associated with increased lung infiltration by inflammatory cells such as neutrophils and mononuclear cells (e.g., monocytes or lymphocytes).

TABLE 3

TLR3 knockout (KO) mice are protected from poly(I:C) induced inflammatory cell level increases in the lung tissues relative to wild-type (WT) mice. Data were expressed as fold increase in the mean lung infiltrating cell count in poly(I:C) treated animals relative to the mean lung infiltrating cell count in animals receiving PBS alone. Data represent values obtained from 6 mice.

| Dose | Total Cells | | Neutrophils | | Mononuclear Cells | |
|---|---|---|---|---|---|---|
| | WT | KO | WT | KO | WT | KO |
| Single Administration 50 µg poly(I:C) | 1.3 | 0.7 | 3 | 1.7 | 1.1 | 0.7 |
| Single Administration 100 µg poly(I:C) | 3.7 | 1.9 | 8.9 | 5.6 | 2.9 | 1.7 |
| Multiple Administration 50 µg poly(I:C) | 15.1 | 3.2 | 58.4 | 5.4 | 13 | 3 |
| Multiple Administration 100 µg poly(I:C) | 17.9 | 2.9 | 69.7 | 6.3 | 15.4 | 2.6 |

Example 13

Figure 16:
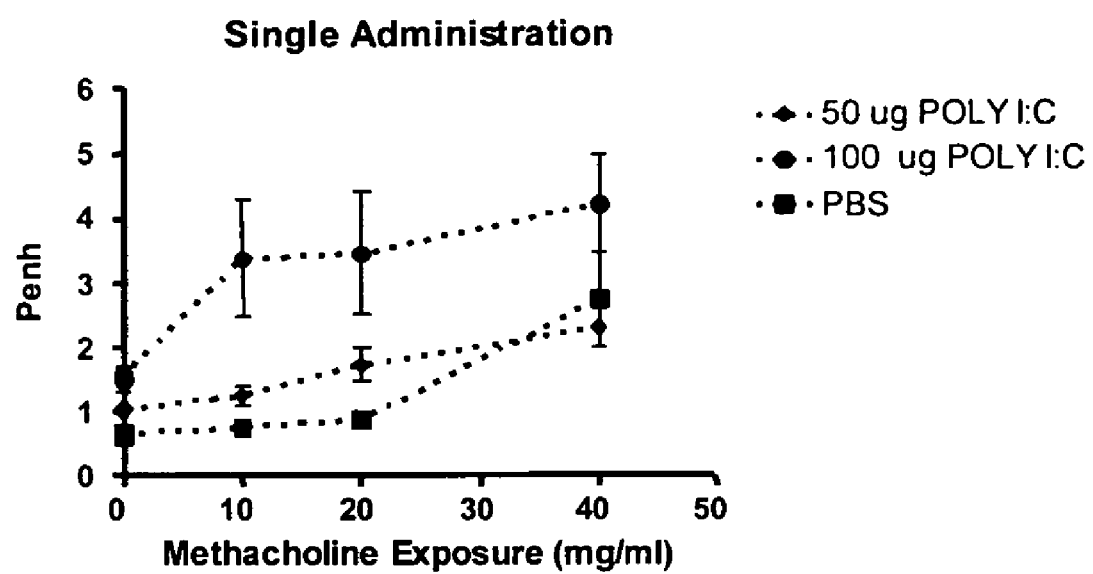
FIG. 16 shows that activation of TLR3 with a single dose of poly(I:C) further impairs lung function in methacholine challenged mice.
Figure 17:
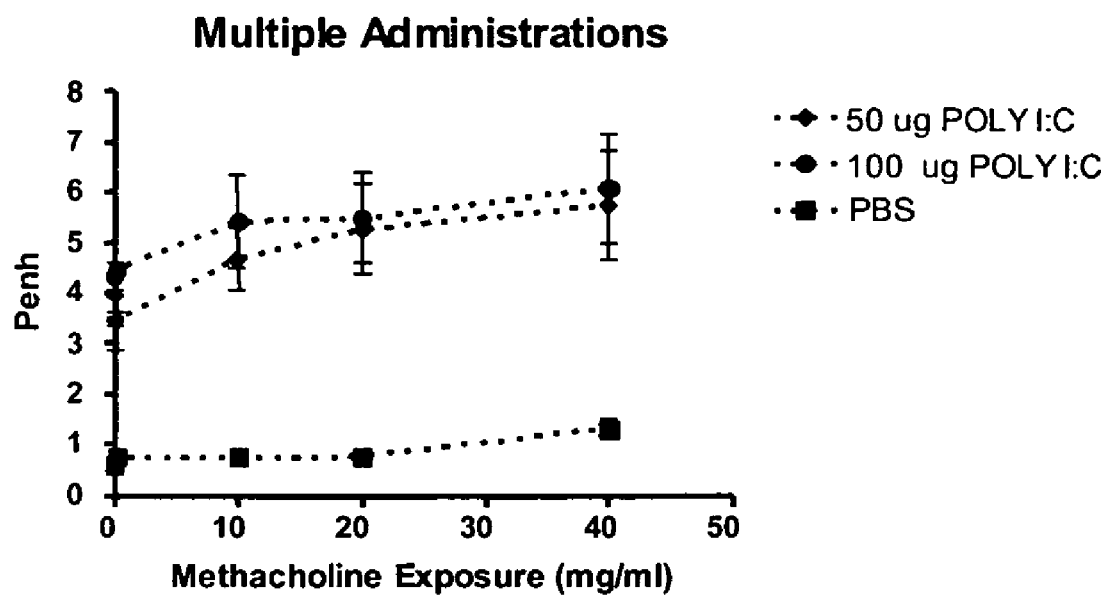
FIG. 17 shows that activation of TLR3 with multiple doses of poly(I:C) further impairs lung function in methacholine challenged mice.

Activation of TLR3 with poly(I:C) Further Impairs Lung Function in Methacholine Challenged Animals Male or female wild-type C57BL/6 mice received a single poly(I:C) dose in PBS or PBS alone (FIG. 16) or three intranasally administered doses of poly(I:C) in PBS or PBS alone every 24 h for three days (FIG. 17). Poly(I:C) activates TLR3. All mice were twelve weeks old. Each poly(I:C) dose contained either 50 µg or 100 µg poly(I:C) and comprised a volume of 50 µL. Each treatment group contained 6-8 mice.

Lung function was assessed using PenH values as a marker of airway obstruction and breathing effort 24 h after the last poly(I:C) dose. PenH values were collected by whole body plethysmograph (WBP) from mice challenged with increasing exposures of methacholine as indicated in FIG. 16 or FIG. 17. Methacholine increases breathing effort and impairs lung function. Methacholine was dissolved in PBS and administered as a nebulized aerosol. All assessments were conducted in accordance with established animal care and use guidelines. Data in FIGS. 16 and 17 represent the mean values from each treatment group of 6-8 mice and the SEM.

The results indicate that activation of TLR3 further impairs lung function in methacholine challenged wild-type mice (FIG. 16 and FIG. 17). This result suggests that TLR3 activation may further impair lung function in individuals already suffering from lung impairment due to infection, chronic obstructive pulmonary disease (COPD), or other disorders. Consequently, therapeutic interventions antagonizing TLR3 activity may prevent additional lung function impairment in individuals already suffering from impaired lung function.

Example 14

TLR3 Knockout Animals are Protected from Poly(I:C) Induced Impairment of Lung Function During Methacholine Challenge Single (FIG. 18) and multiple dose (FIG. 19) poly(I:C) administration were performed on male or female wild-type C57BL/6 mice or TLR3 knockout mice as described in Example 12. Lung function was assessed using PenH values collected by WBP as described in Example 12. Methacholine administration was also as described in Example 12. All assessments were conducted in accordance with established animal care and use guidelines. Data in FIGS. 18 and 19 represent the mean values from each treatment group of 6-8 mice and the SEM.

Figure 18:
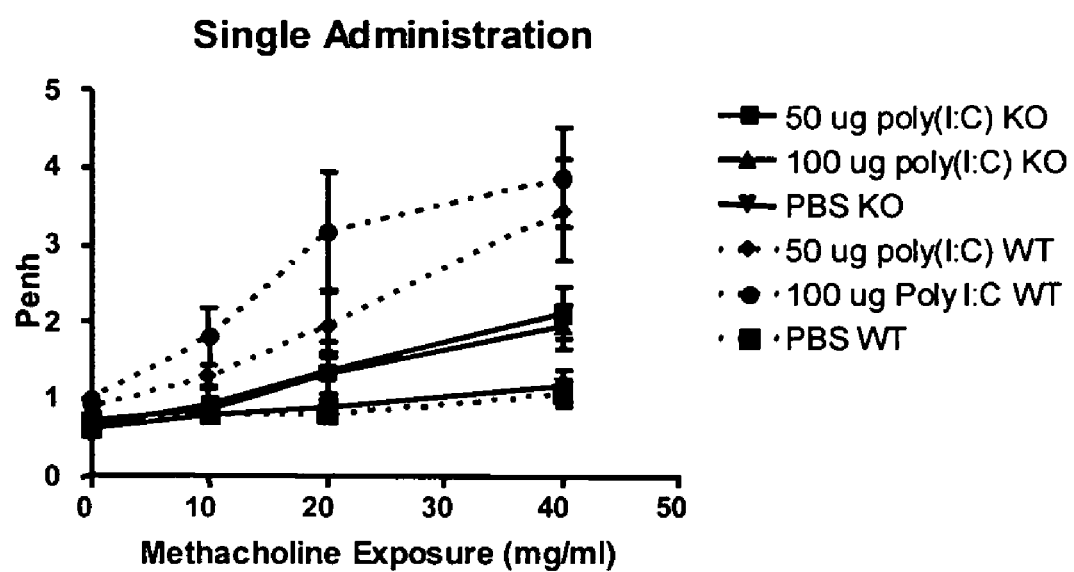
FIG. 18 shows that TLR3 knockout mice are protected from single poly(I:C) dose induced impairment of lung function during methacholine challenge.
Figure 19:
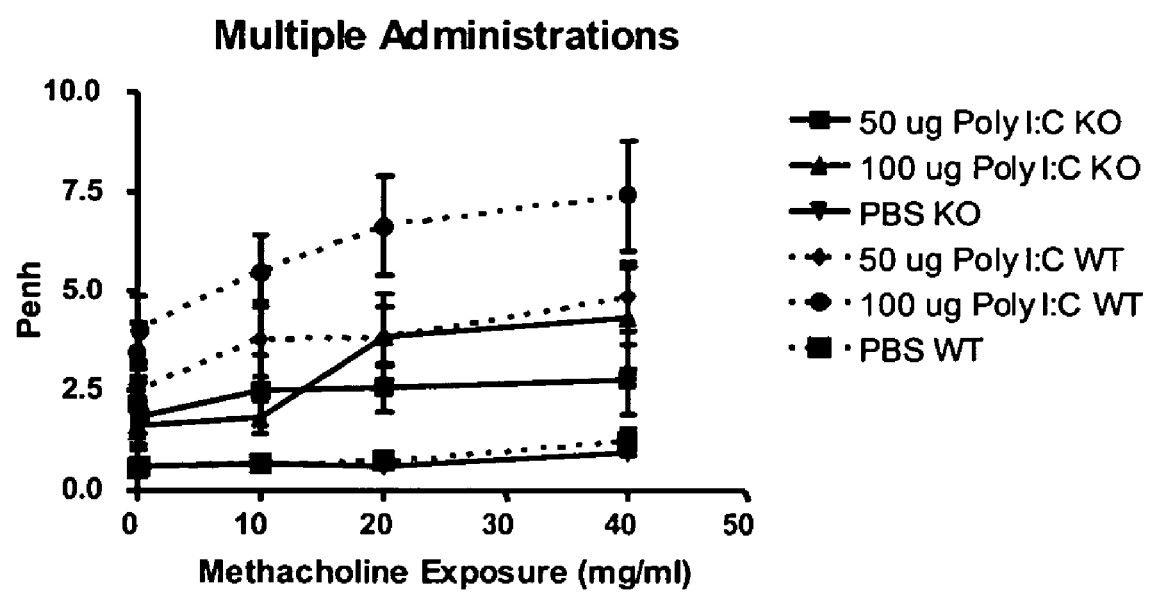
FIG. 19 shows that TLR3 knockout mice are protected from multiple poly(I:C) dose induced impairment of lung function during methacholine challenge.

TLR3 knockout mice are protected from poly(I:C) induced impairment of lung function during methacholine challenge (FIG. 18 and FIG. 19). This result indicates that therapeutic interventions antagonizing TLR3 activity may prevent additional lung function impairment in individuals already suffering from impaired lung function due to infection, chronic obstructive pulmonary disease (COPD), or other disorders such as asthma. Additionally, this result further indicates that the effects of poly(I:C) administration are largely due to TLR3 activation.

Example 15 hTLR3 Antagonist Effect on Cytokine and Chemokine Production in Human Lung Bronchial Epithelial Cells The human lung bronchial epithelial cell line BEAS-2B was obtained from the American Type Culture Collection (CRL-9609). BEAS-2B were grown in collagen I coated flasks (BD Biosciences) in LHC-9 serum free media and harvested after a brief wash in 0.25% trypsin/EDTA. Cells were then washed in LHC-9 serum free media (Biosource) and resuspended in LHC-9 media at $1\times10^6$/ml. Cells were plated onto collagen I coated 96-well flat bottom plate at 200 µl/well; triplicate culture wells were run for each condition.

After a 6 h incubation to allow cell attachment, media was removed and replaced with 200 µl of fresh media. Ten-fold serial dilutions of mAb 1068 starting at 100 µg/ml were incubated for 40 min at 37° C. prior to addition of 125 ng/well of the TLR3 agonist poly(I:C). Culture supernatants were collected 24 h post poly(I:C) stimulation and Luminex® multichannel analysis (Luminex Corp., Austin, Tex.) was performed on samples to assay IL-6, IL-8, RANTES, MCP-1, IP-10, IFN-α, IFN-γ, IL-1β, IL-12, TNF-α, MCP-1, and IL-10 expression levels.

Figure 20:
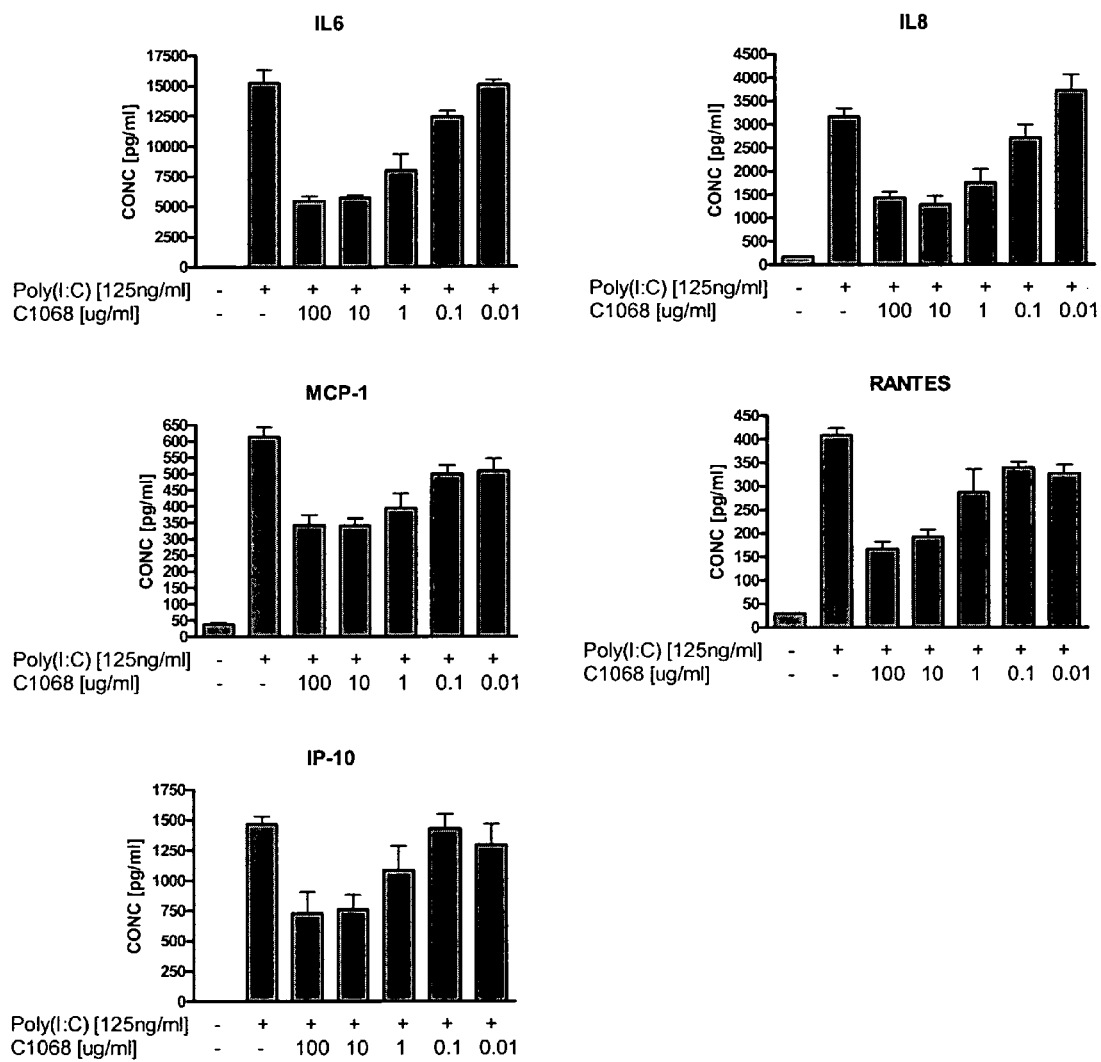
FIG. 20 shows the effect of an TLR3 antagonist on cytokine and chemokines production in human lung bronchial epithelial cells.

The results indicated that anti-TLR3 antagonist mAb 1068 (identified in FIG. 20 as mAb CNTO260) decreases IL-6, IL-8, RANTES, MCP-1 and IP-10 production in poly(I:C) stimulated BEAS-2B cells. Expression of IL-6, IL-8, RANTES, MCP-1 and IP-10 was decreased in a mAb 1068 dose dependent manner as shown in FIG. 20. IFN-α, IFN-γ, IL-1β, IL-12, TNF-α, MCP-1, and IL-10 expression was not detected in the samples.

Example 16 hTLR3 Antagonist Treatment Increases Survival of Lethal Pneumonia

Figure 22:
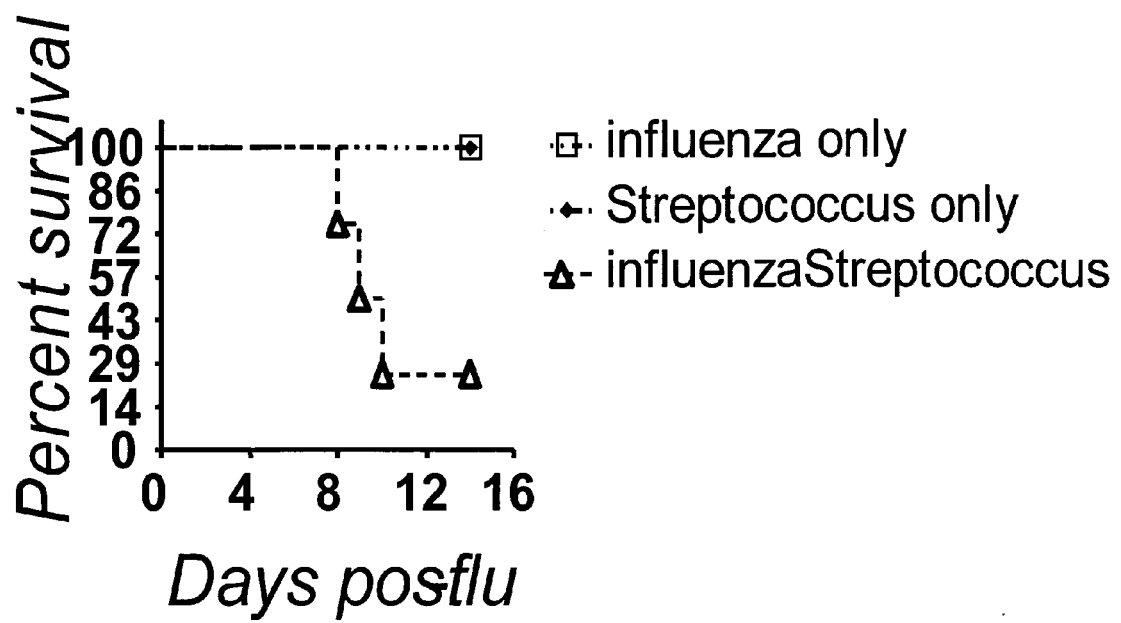
FIG. 22 shows development of lethal pneumonia in a murine model after infection with sublethal doses of influenza virus A/PR/8 and *Streptococcus pneumoniae*.

In these experiments, 8 to 10 week old female wild-type C57BL/6 mice were infected intranasally with 5 plaque-forming units (PFU) of influenza virus A/PR/8 in 50 µL of PBS and then infected intranasally seven days later with 50 colony forming units (CFU) of the *S. pneumoniae* bacterium in 50 µL of PBS. Alone the viral and bacterial doses administered were sublethal, but together these doses were lethal to the majority of mice (FIG. 22). Control groups of mock-infected mice received PBS instead of influenza virus A/PR/8 or *S. pneumoniae*. hTLR3 antagonist treated mice received either 0.6 mg or 0.06 mg in 0.2 ml of PBS administered by intraperitoneal injection 2 h prior to *S. pneumoniae* inoculation on day 7 (prophylactic administration) and were dosed identically again on day 8 (therapeutic administration). Control groups of mock treated mice received 0.6 mg or 0.06 mg in PBS of an intraperitoneally administered, nonspecific IgG. Each treatment or control group contained 7 mice. All assessments described here were conducted in accordance with IACUC guidelines.

Influenza A/PR/8 virus was cultured in chicken eggs, PFU titer was determined using standard assays with MDCK cells, and maintained as frozen viral stock for inoculations. *Streptococcus pneumoniae* (ATCC® Number: 6301™) inocula were grown overnight on trypticase soy agar plates containing 5% sheep's blood (TSA/blood), bacteria where then removed from the plates and suspended in phosphate-buffered saline (PBS). Bacterial CFU titer in the PBS suspension was calculated using the optical density at 600 nm and standard methods. Bacterial inocula were then prepared in PBS. CFU in bacterial inocula were confirmed by standard colony forming assays to determine the number of bacteria actually present in the inoculum administered to mice.

After preparation of inoculums, mice were infected intranasally with influenza A/PR/8 virus or *S. pneumoniae* as described above. Mock-infected control mice received intranasally administered PBS as described above. hTLR3 antagonist treated mice received intraperitoneally administered mAb 1068, both prophylactically and therapeutically, as described above. Mock treated control mice received intraperitoenally administered non-specific IgG in PBS as described above. The influenza A/PR/8 virus and *S. pneumoniae* doses alone were sublethal as 100% of mice infected with virus or bacteria alone survived (FIG. 22). However, viral or bacterial infection together at these otherwise sublethal doses generated lethal pneumonia in the majority of mice (FIG. 22).

Figure 23:
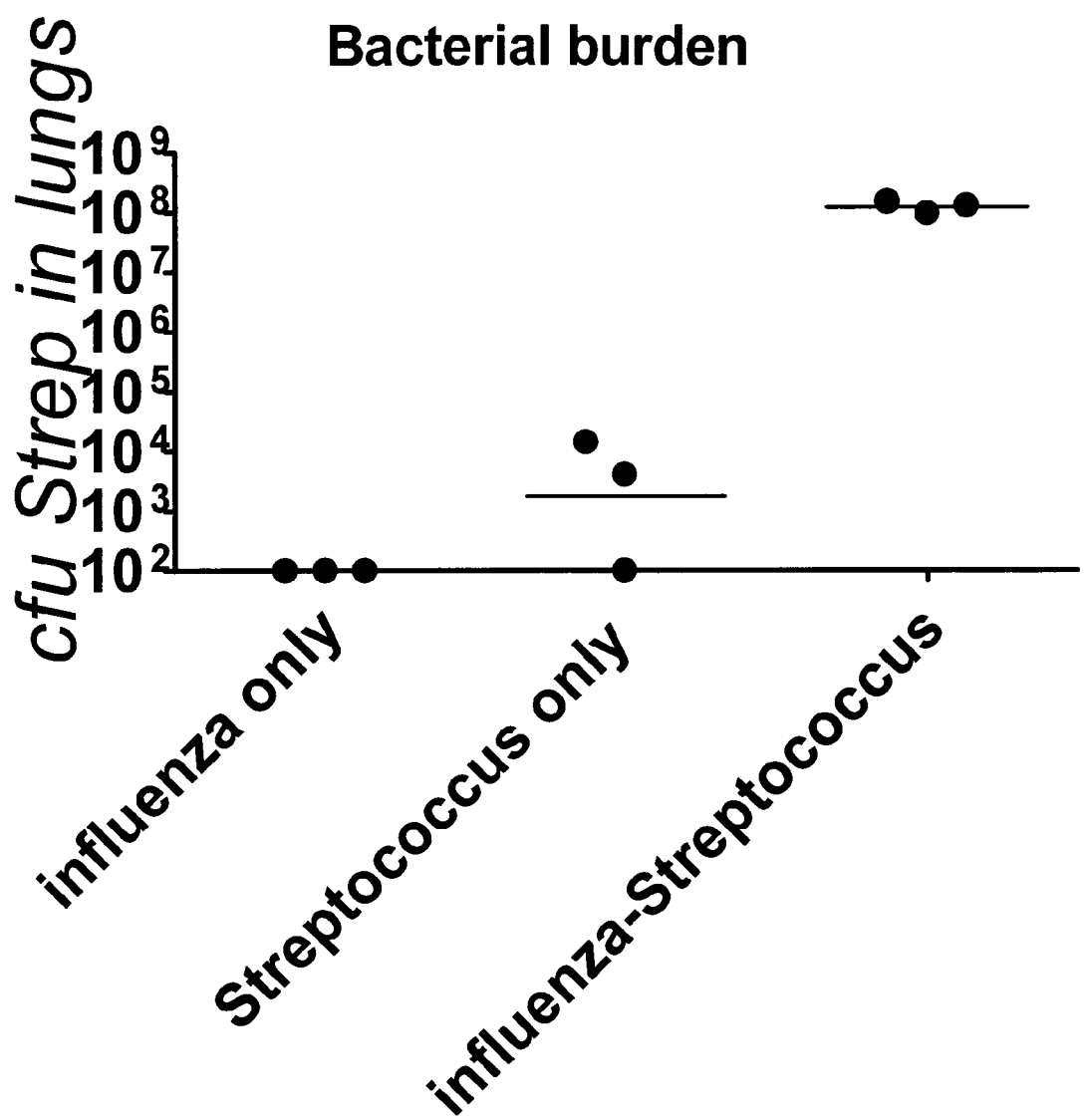
FIG. 23 shows bacterial burden in the lungs of influenza virus A/PR/8 and *S. pneumoniae* infected mice.
Figure 24A:
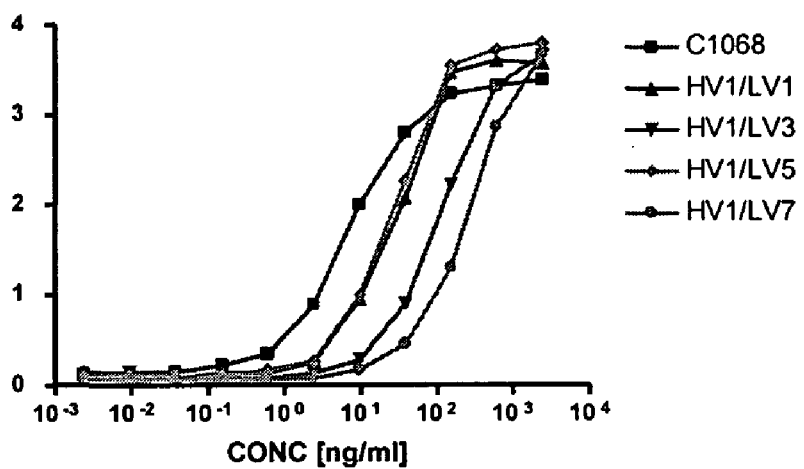
FIGS. 24A, B, C and D shows binding of human-adapted anti-TLR3 mAbs to hTLR3 in ELISA assays.
Figure 24B:
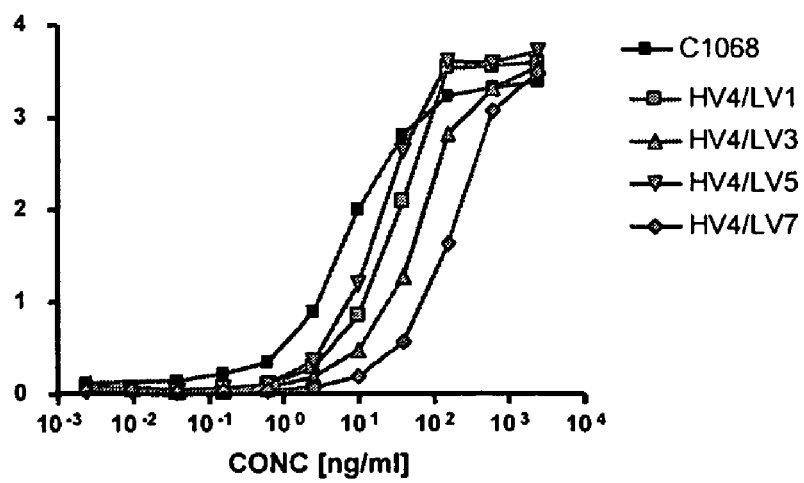
Figure 24C:
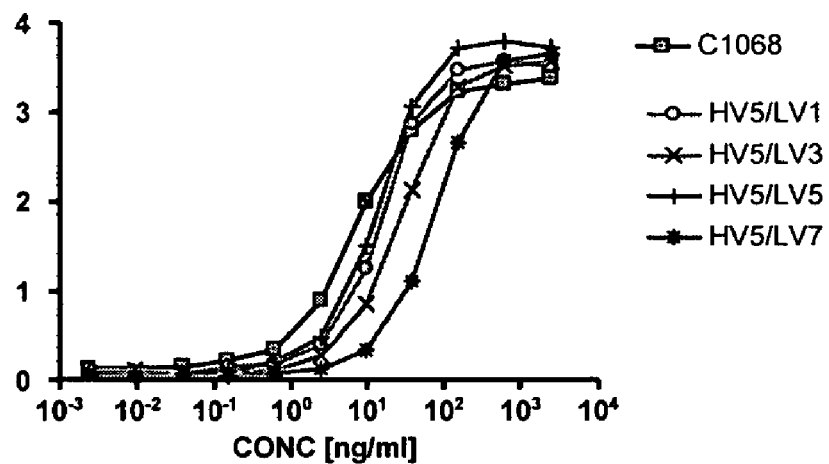
Figure 24D:
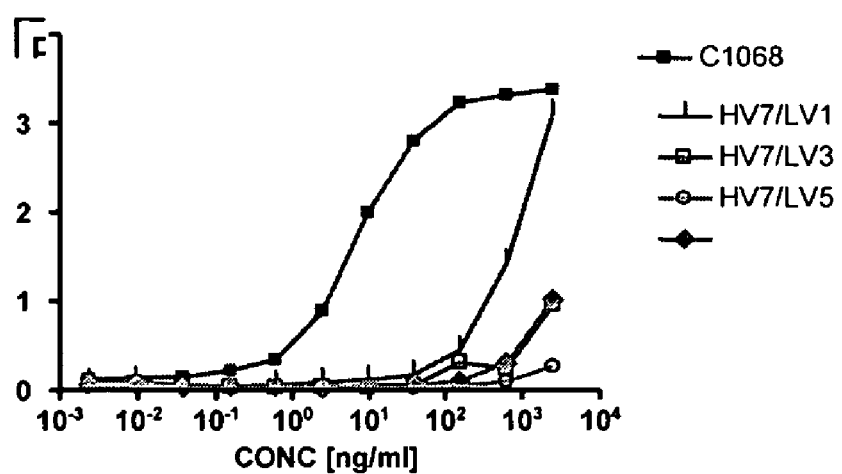
Figure 25:
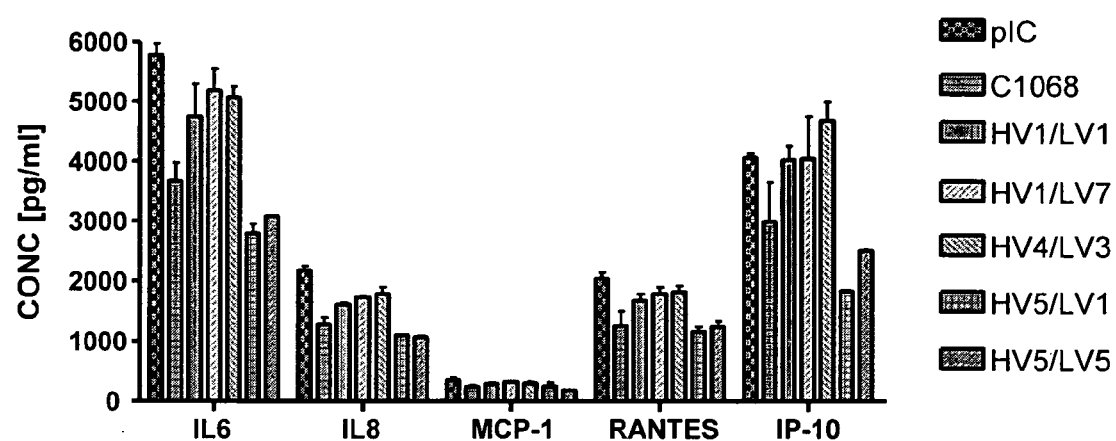
FIG. 25 shows assessment of human-adapted anti-TLR3 mAbs in a cell-based cytokine release assay.
Figure 26:
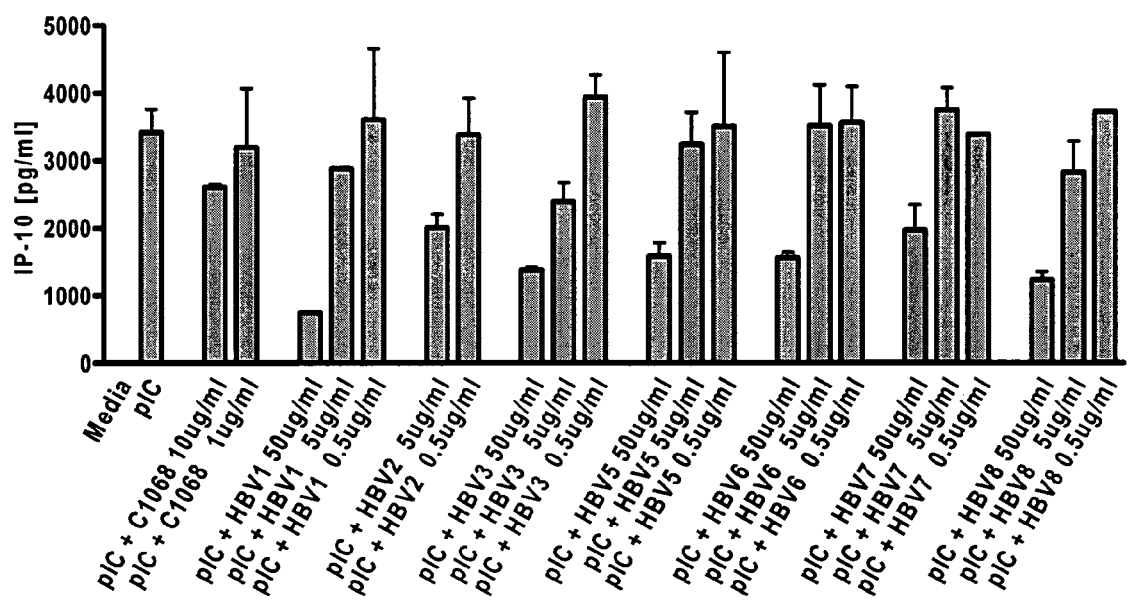
FIG. 26 shows the evaluation of variant mabs HBV1 through HBV8 (excluding HBV4) in a cell based bioactivity assay with an IP-10 readout.
Figure 27:
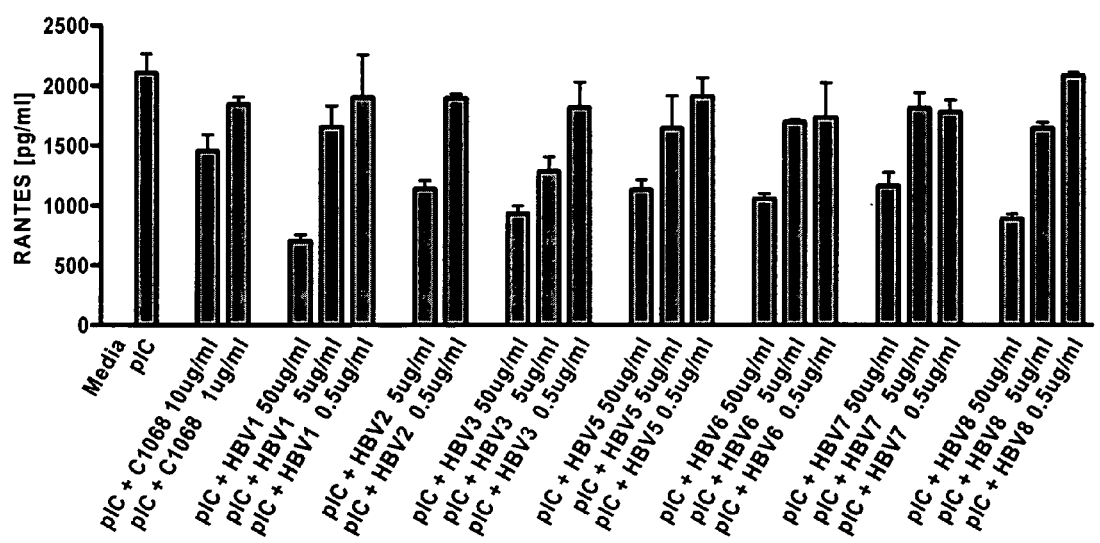
FIG. 27 shows the evaluation of variant mAbs HBV1 through HBV8 (excluding HBV4) in a cell based bioactivity assay with a RANTES readout.
Figure 28:
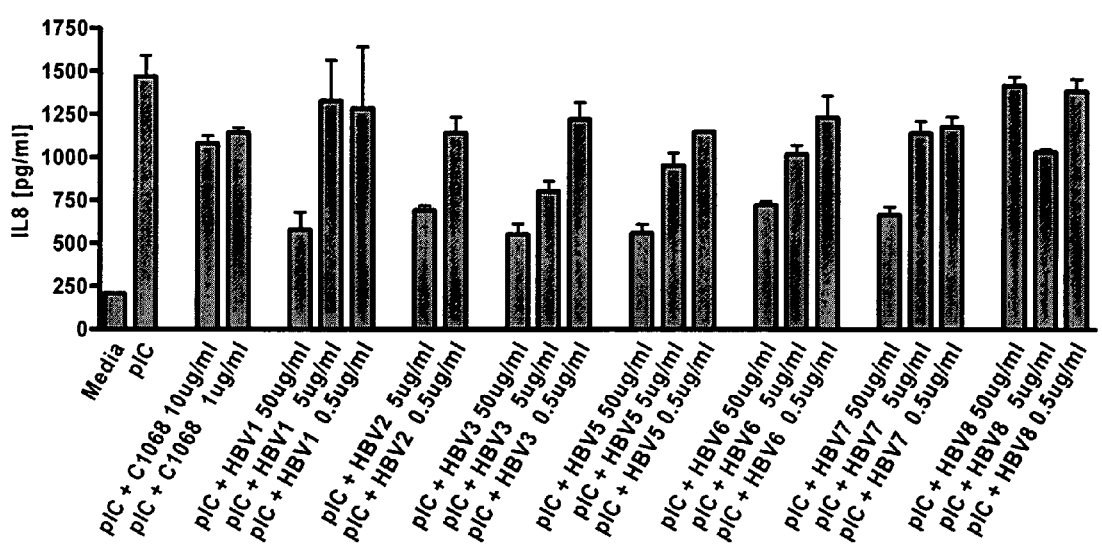
FIG. 28 shows the evaluation of variant mAbs HBV1 through HBV8 (excluding HBV4) in a cell based bioactivity assay with an IL-8 readout.
Figure 29:
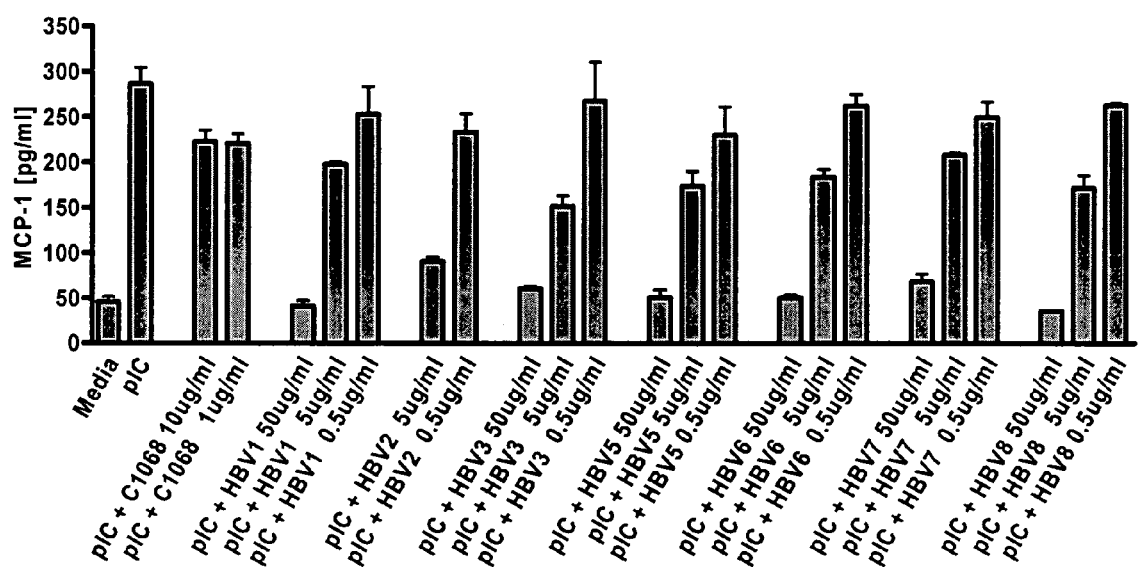
FIG. 29 shows the evaluation of variant mAbs HBV1 through HBVB (excluding HBV4) in a cell based bioactivity assay with an MCP-1 readout.
Figure 30:
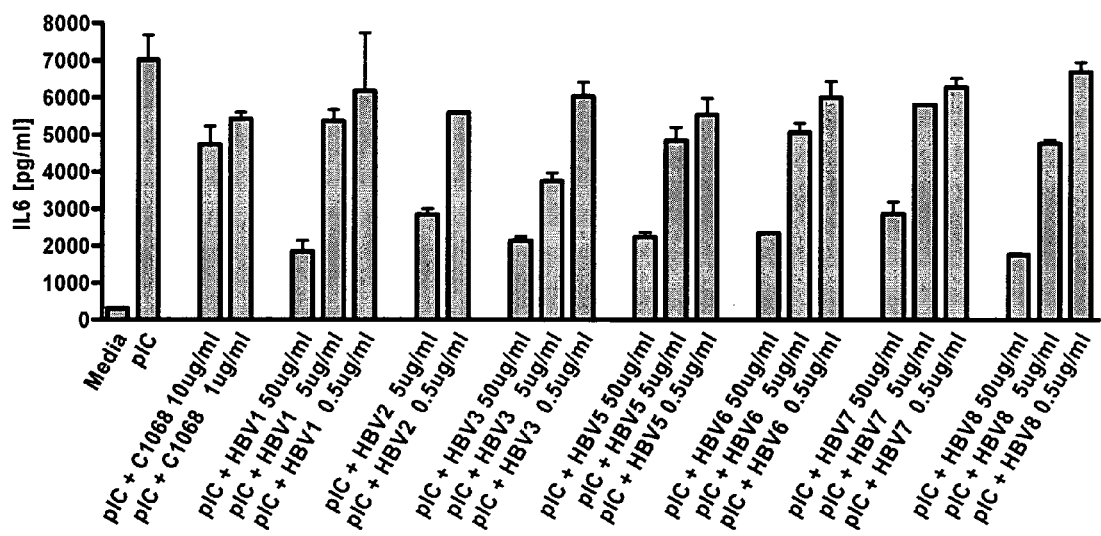
FIG. 30 shows the evaluation of variant mAbs HBV1 through HBV8 (excluding HBV4) in a cell based bioactivity assay with an IL-6 readout.

Mice were euthanized 48 hours post-bacterial infection, lungs were harvested aseptically, homogenized in sterile PBS, homogenate dilutions in PBS prepared, and dilutions were placed on TSA/blood plates to determine bacterial burden in the lungs. Plates were then incubated until colonies were visible and CFUs counted. As shown in FIG. 23, prior infection with a sublethal dose of influenza virus increased bacterial burdens in the lungs of mice 2 days after *S. pneumoniae* infection.

Figure 21:
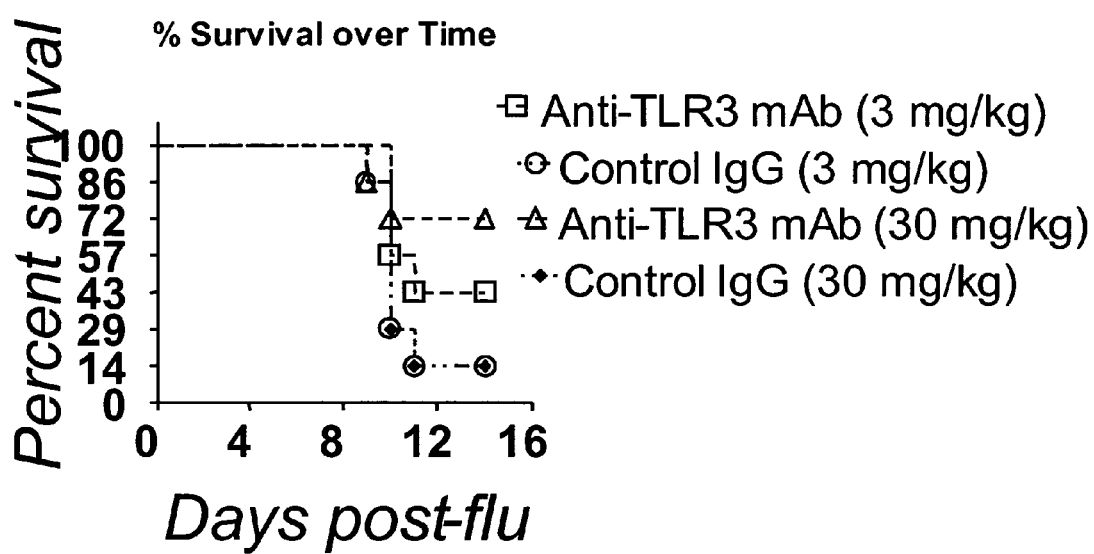
FIG. 21 shows increased survival in a murine model of lethal pneumonia through prophylaxis and treatment with a TLR3 antagonist.

Administration of 0.6 mg or 0.06 mg of anti-TLR3 mAb 1068 per mouse on days 8 and 9 increased the mouse survival rate in mice infected with influenza virus A/PR/8 and *S. pneumoniae* relative to control mice receiving a 0.6 mg or 0.06 mg of a non-specific IgG control mAb (FIG. 21).

Importantly, the body weight of the average female C57BL/6 mouse is between 18 g and 20 g; consequently the dose range of the TLR3 antagonist administered was between approximately 3.0 mg/kg and 3.3 mg/kg body weight for mice receiving 0.6 mg of mAb 1068 or between approximately 30 mg/kg and 33 mg/kg body weight for mice receiving 0.06 mg of mAb 1068. FIG. 21 is labeled to indicate the lower end of this range.

Example 17

Effect of TLR3 Activity on Colonic Epithelial Cell Proliferation Rate

The proliferation rate of colonic epithelial cells in a murine model was increased by knocking-out TLR3 receptor gene activity (data shown in Table 4). In these experiments, female wild-type C57BL/6 mice or the TLR3 knock-out mice described above were each given 1 mg of bromodeoxyuridine (BrdU) in 1 ml of PBS intraperitoneally and sacrificed 2 h later. All mice were 6-8 weeks old and each treatment group had at least 3 mice.

Colons for histopathological analyses were then harvested. Colons tissue was fixed, cut into segments, embedded in paraffin, and 5 µm sections were prepared. Sections were incubated sequentially with a mouse anti-BrdU IgG mAb (Becton-Dickinson Biosciences, Inc., San Jose, Calif.) a goat anti-mouse IgG mAb horse radish peroxidase (HRP) conjugate (Becton-Dickinson Biosciences, Inc., San Jose, Calif.), and diaminobenzidine (DAB) substrate (Becton-Dickinson Biosciences, Inc., San Jose, Calif.) per the manufacturer's instructions. Incubated sections were counterstained with hematoxylin by standard methods.

Incubated sections were then visually inspected and the number of cells in the colon crypts staining positive for BrdU incorporation into the DNA were counted. Cells were counted in 24 consecutive well-oriented crypts in a section from the same segment of the colon. BrdU incorporation was used as a surrogate marker to identify cells progressing through the cell cycle; i.e. proliferating cells. In Table 4, proliferation rate data are expressed as the mean number of BrdU stained cells per colon crypt per animal per 2 hours. These data are presented as the mean proliferation rate±standard deviation ($P<0.0001$, T-test). The data indicate that inactivation of TLR3 increases colonic epithelial cell proliferation.

TABLE 4

Increased colonic epithelial cell proliferation rates in TLR3 knockout (KO) mice.

| | Wild-Type Mice | TLR3 Gene Knockout Mice |
|---|---|---|
| Colonic Epithelial Cell Proliferation Rate | 2.4 ± 0.6 | 5.6 ± 1.6 |

Example 18

Effect of TLR3 Activity on Colonic Epithelial Cell Proliferation Rate During Recovery from Inflammatory Bowel Disease The proliferation rate of colonic epithelial cells during recovery in a murine model of inflammatory bowel disease (IBD) was increased by knocking-out TLR3 receptor gene activity (Table 5). In these experiments, female wild-type C57BL/6 mice or the TLR3 KO mice described above were each given 5% (w/v) dextran sulfate sodium (DSS) in the drinking water for 3 days to induce acute ulcerative colitis. Mice were then supplied with plain water until the end of the experiment 30 h later. Mice were injected with BrdU, as described above, 6 h after they began receiving plain water. Mice were then allowed to recover from DSS induced ulcerative colitis for 24 hrs and were sacrificed. All mice were 6-8 weeks old and each treatment group had at least 3 mice.

Colon samples for histopathological analyses of colonic crypt cell proliferation were prepared and analyzed as described in Example 15 above. Proliferation rate data are expressed as the mean number of BrdU stained cells per colon crypt per animal per 24 hours. These data are presented as the mean proliferation rate±standard deviation (P<0.004, T-test). The data in Table 5 indicate that inactivation of TLR3 increases the proliferation rate of colonic epithelial cells during recovery from inflammatory bowel disease.

TABLE 5

Increased colonic epithelial cell proliferation rates during recovery in a TLR3 KO mouse DSS induced model of inflammatory bowel disease.

|  | Wild-Type DSS Treated Mice | TLR3 Gene Knockout DSS Treated Mice |
| --- | --- | --- |
| Colonic Epithelial Cell Proliferation Rate | 0.4 ± 0.2 | 2.8 ± 0.6 |

Example 19

Insulin Sensitivity in TLR3 Knockout Mice

TLR3 Knockout (KO) (on a C57BL/6 background) and wild-type (WT) control mice (C57 Bl/6) were fed a high fat diet (Purina TestDiet #58126) consisting of 60.9% kcal fat and 20.8% kcal carbohydrates. Control TLR3 KO and WT mice were fed with normal chow. Animals were fasted overnight and a glucose tolerance test (GTT) was performed by injecting 1.0 mg/g glucose intraperitoneally and blood glucose readings were obtained at 0, 15, 30, 60, 90, and 120 minutes.

Figure 31A:
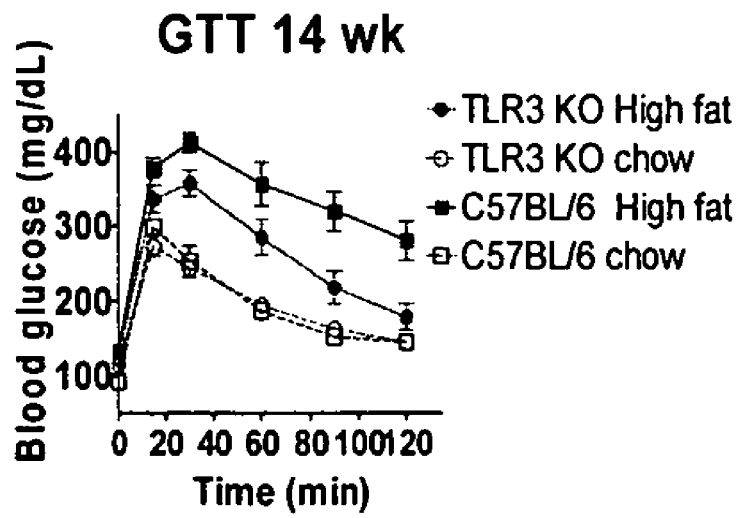
FIGS. 31A and B shows that TLR3 knockout mice on a high-fat diet are protected from development of impaired glucose tolerance associated with high-fat feeding.
Figure 31B:
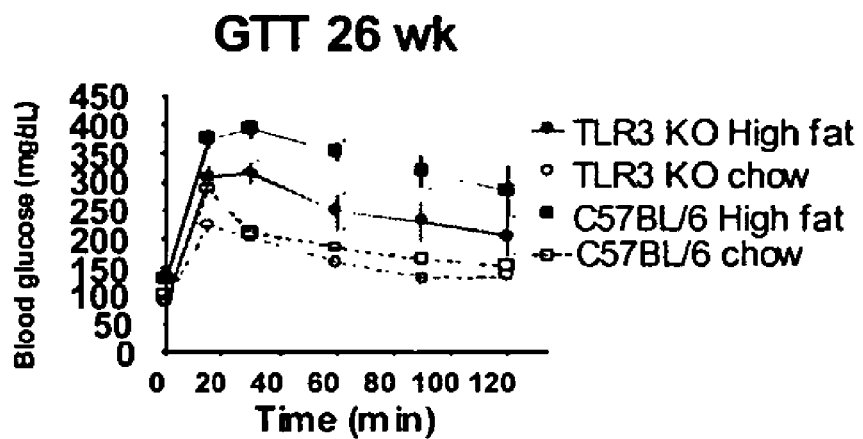

FIG. 31 shows that TLR3 KO mice on a high fat diet for 14 and 26 weeks showed improvements in a glucose tolerance test when compared to wild type mice on a high fat diet. Mice fed with normal chow did not display any changes as expected. These results showed that TLR3 signaling might impact insulin sensitivity and provide a basis for the utility of TLR3 antagonists for the treatment of Type 2 diabetes.

Figure 32:
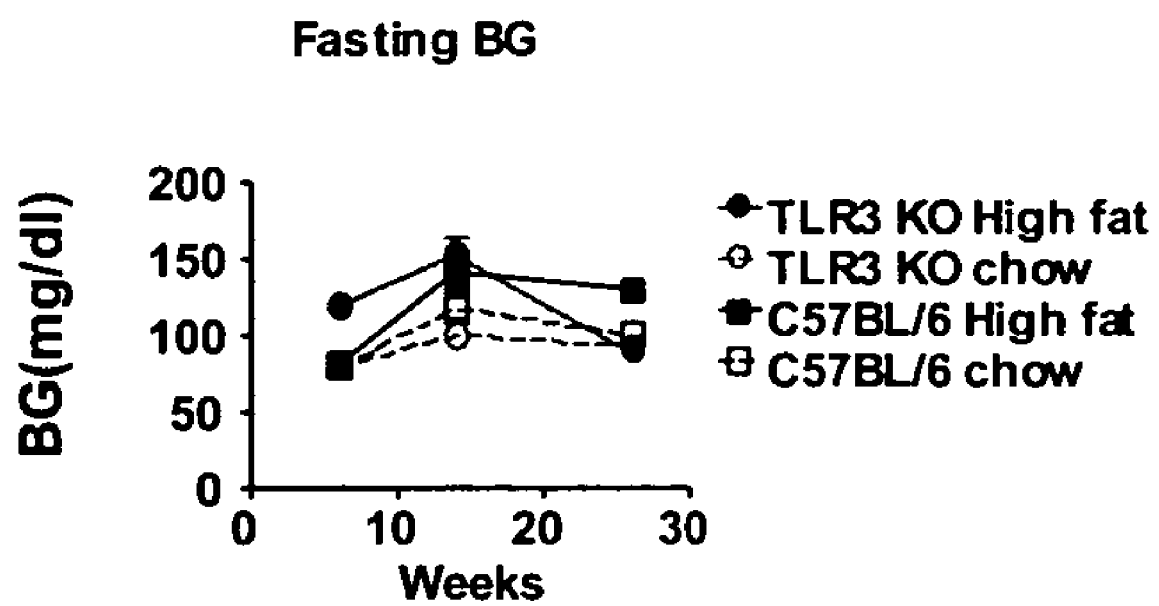
FIG. 32 shows that TLR3 knockout mice have normal fasting blood glucose levels after 26 weeks on a high-fat diet.

FIG. 32 shows the fasting blood glucose levels in mice on a high fat and regular chow diet. TLR3 KO animals normalize their fasting blood glucose levels when compared to wild type mice on a high fat diet. These data suggest that TLR3 signaling may interfere with liver glucose metabolism that contributes to an impairment in glucose tolerance and development of insulin resistance.

Figure 33A:
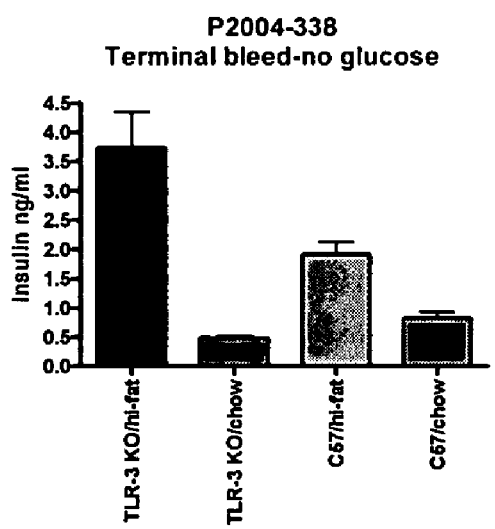
FIGS. 33A, B and C shows an increase in fasting insulin levels before and after a glucose challenge in TLR3 knockout mice after 26 weeks on a high-fat diet.
Figure 33B:
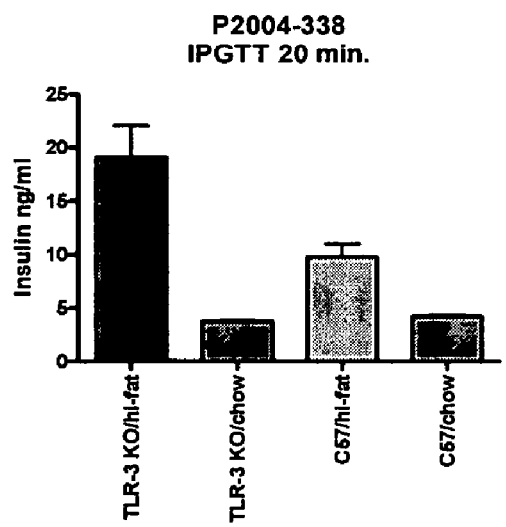
Figure 33C:
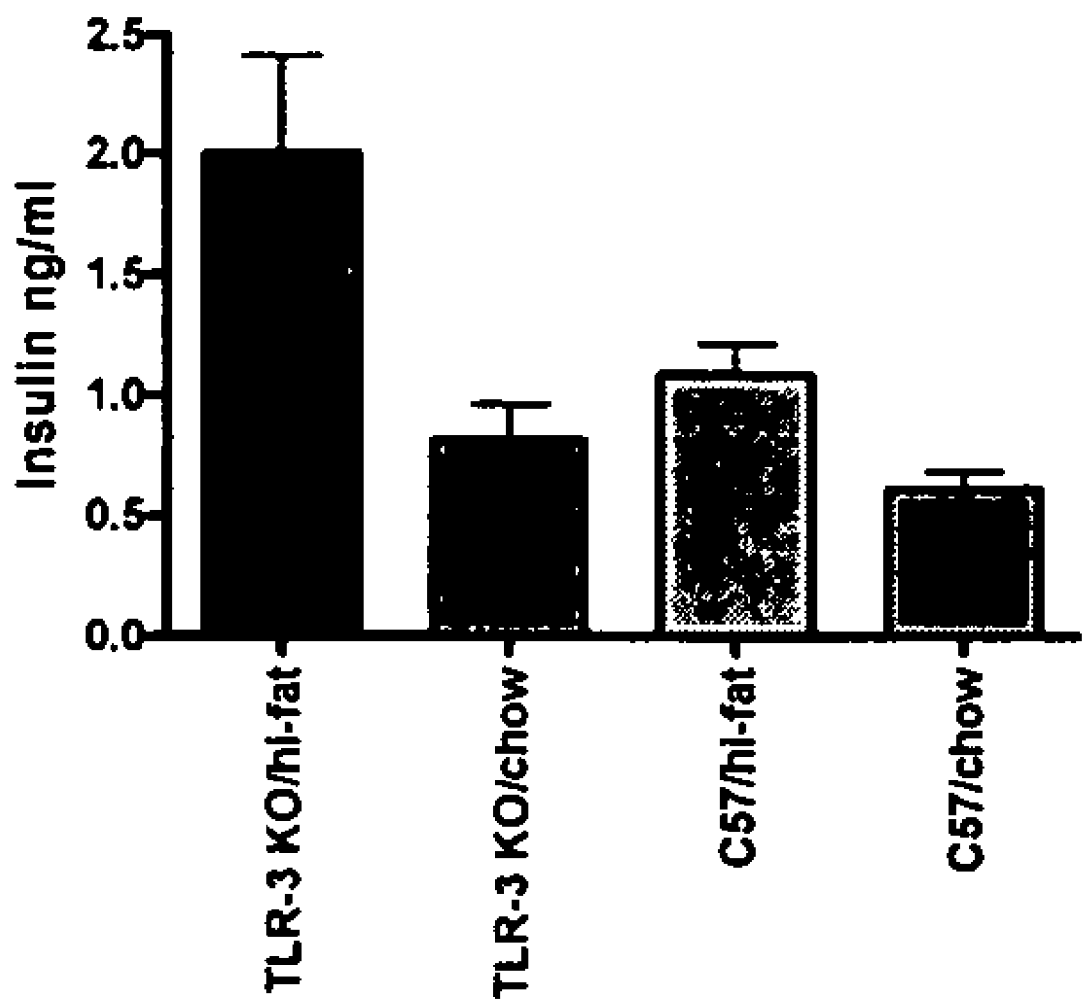
Figure 34A:
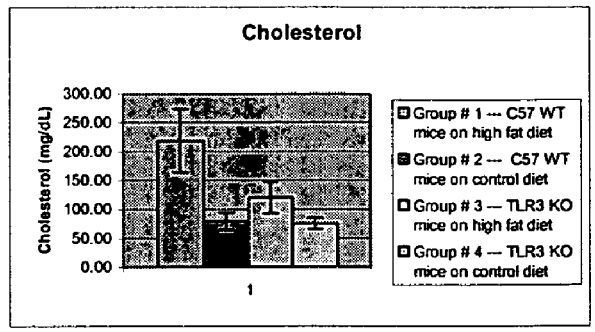
FIGS. 34A, B, C, D and E shows improved lipid profiles of TLR3 knockout mice fed a high-fat diet for 30 weeks compared to wild-type mice on a high-fat diet.
Figure 34B:
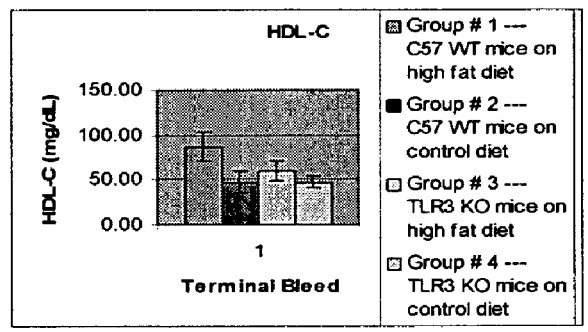
Figure 34C:
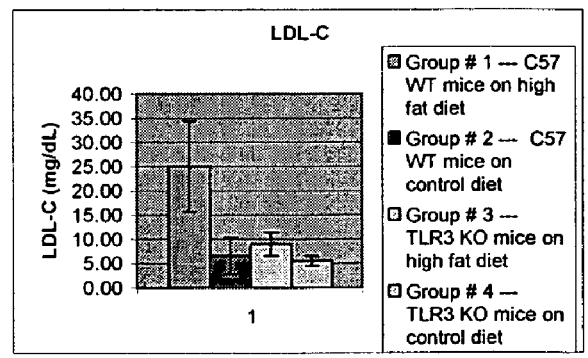
Figure 34D:
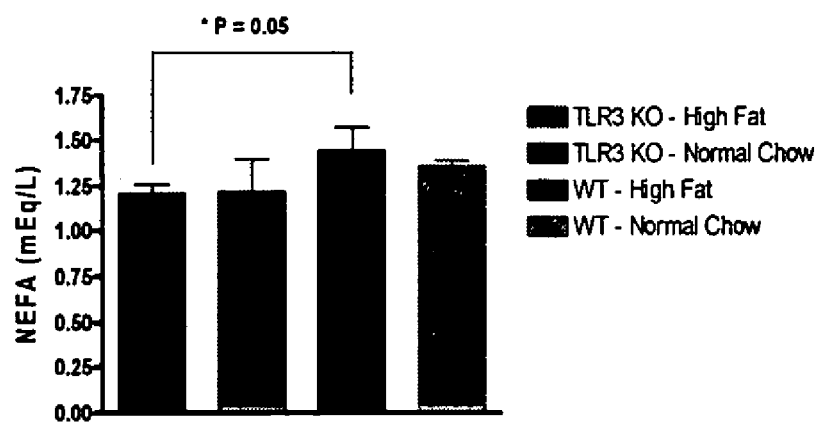
Figure 34E:
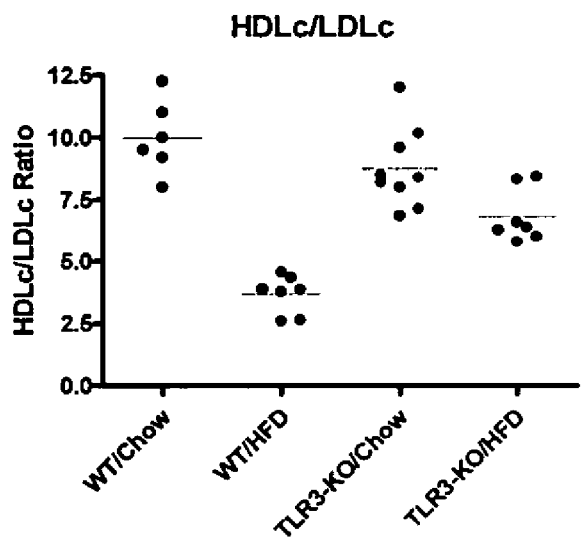

Next, insulin levels were assessed in TLR3 KO and wild-type mice fed with a normal chow or high fat diet. Blood insulin levels were measured in mice fasted overnight before and after glucose challenge. Insulin was quantitated using the Crystal Chem (Downers Grove, Ill.) Ultra-Sensitive ELISA Assay kit (cat # 90060). TLR3 KO mice fed a high fat diet showed increased insulin levels at baseline (without glucose challenge) and 20 and 60 minutes post glucose challenge (FIG. 33). Overall, the data obtained in the glucose tolerance test suggest that the absence of TLR3 signaling impacts insulin levels and insulin sensitivity.

At 30 weeks on a high fat diet TLR3 KO mice were sacrificed and their lipid profiles were determined in serum samples. The levels of total cholesterol, HDl, LDL, triglicerides and FFA were determined. Briefly, all lipid tests were calibrated by referencing the change in absorbance of the unknown samples to the change in absorbance of the standards using GEMCAL Reference Serum (Alfa Wassermann Diagnostic Technologies, LCC, West Caldwell, N.J.). Two levels of controls were run each day prior to reporting results. Samples were loaded and lipid data was acquired and expressed in conventional units mg/dL. The FFA levels were determined using NEFA kit (Wako). The TLR3 KO animals showed lower levels in circulating cholesterol, LDL and HDL as well as FFA compared to wild-type mice on the same diet. These results show that the absence of TLR3 signaling has a beneficial role in lowering cholesterol levels, showing a utility for TLR3 antagonist MAbs for the treatment of cardiovascular diseases and preventing development of cardiovascular complications associated with Type 2 diabetes.

In sum, the results presented show that TLR3 KO mice fed a high fat diet were protected from developing impaired glucose tolerance as a feature of insulin resistance compared to wild-type mice, demonstrating that the absence of TLR3 signaling protects mice against Type 2 diabetes. Furthermore, the data show that TLR3 KO mice on a high fat diet had lower levels of total cholesterol, LDH and HDL cholesterol as well as HDLc/LDLc ratio compared to wild type mice on a high fat diet, thus indicating a beneficial role of TLR3 antagonist in down-modulating risk factors associated with cardiovascular diseases. These finding suggest the use of TLR3 inhibitor as a method to treat Type 2 diabetes, dislipidemia and metabolic syndrome.

Example 20

Generation and Characterization of Human-Adapted Anti-TLR3 mAbs

The amino acid sequence of the murine anti-TLR3 mAb C1068 was used to query a human antibody database compiled from public antibody sequence databases. The variable region of the heavy chain of C1068 (SEQ ID NO: 6) showed high homology to four heavy chain germline sequences, namely VB_1-03/JH1 72,VB_1-02/JH1 71, VB_1-08/JH1 71 and VB_1-69/JH2 70 of the human VH1 heavy chain family. Four nucleic constructs in which the CDR regions of C1068 heavy chain were then transferred into the selected human germline heavy chain sequences were synthesized to generate four human-adapted anti-TLR3 mAb heavy chains designated as HV1, HV4, HV5 and HV7 having the variable region amino acid sequences shown in SEQ ID NOs: 25, 27, 29 and 31, respectively.

The variable region of the light chain of C1068 (SEQ ID NO: 16) showed high homology to four light chain germline sequences, namely VB_O12/JK2 78, VB_A30/JK2 77, VB_A20/JK4 76 and VB_L1/JK2 76 of the human VK I family. Four nucleic constructs in which the CDR regions of C1068 light chain were then transferred into the selected human germline light chain sequences were synthesized to generate four human-adapted anti-TLR3 mAb light chains designated as LV1, LV3, LV5 and LV7 having the variable region amino acid sequences shown in SEQ ID NOs: 33, 35, 37 and 39, respectively.

Sixteen mAbs representing all possible combinations of the four heavy and four light chain variable region constructs were expressed. All heavy chain variable region frameworks were expressed with a human IgG4 heavy chain constant region having a Ser to Pro substitution at residue 108 and Phe114 and Leu115 to Ala substitutions (SEQ ID NO: 41); S228P, F234A and L235A in the full-length heavy chain. All light chain variable region frameworks were expressed using a human K constant region (SEQ ID NO: 4).

Antibodies were expressed transiently in mammalian cells by co-transfection of appropriate heavy and light chain containing plasmids. Antibodies were purified using standard protein A purification and dialyzed into PBS for characterization.

All 16 mAbs were assessed for binding to the extracellular domain of human TLR3 (SEQ ID NO: 4) using an ELISA format as compared to the parental murine mAb C1068. Briefly, soluble human TLR3 extracellular domain was coated into the wells of a 96 well plate and candidate mAbs were incubated at various concentrations ($10^{-3}$ to $10^3$ ng/ml) and bound antibody was detected with rabbit anti-mouse IgG-HRP for murine IgG1 isotypes (Zymed, South San Francisco, Calif.) or HRP-labeled anti-human IgG (Jackson 109-036-088) for human IgG4 isotypes. $EC_{50}$ values were determined and the results are shown in FIG. 24 and Table 7 below.

TABLE 7

Calculated $EC_{50}$ values for combinatorial mAbs

| $EC_{50}$ ng/ml | HV1 | HV4 | HV5 | HV7 |
|---|---|---|---|---|
| LV1 | 29.2 | 29.1 | 15.5 | 1474.0 |
| LV3 | 117.7 | 60.2 | 28.9 | >5000 |
| LV5 | 27.7 | 18.7 | 13.7 | 1820.0 |
| LV7 | 288.8 | 182.9 | 78.6 | 4258.0 |

The calculated $EC_{50}$ for C1068 was 8 ng/ml; the results indicated that 12 of the human-adapted mAbs had less than a 40-fold reduction in calculated $EC_{50}$ relative to the murine parent mAb 1068. The mabs having the $EC_{50}$ values in bold text were further characterized by determining binding affinity by Biacore and binding activity in a cell-based cytokine release assay.

Measurement of binding affinity by Biacore was performed by mAb capture and TLR3 capture techniques. MAb capture analysis was performed at 25° C. using a Biacore 2000 biosensor equipped with a CM5 chip with surfaces modified with protein A (6,000 RU) at 25° C. by standard amine coupling. Antibody was diluted to 30 nM and captured for one minute on different protein A surfaces. TLR3 was injected at 0, 0.1, 0.3, 1.0, 3.0, and 9.0 nM and associations and dissociations were monitored for 5 minutes. The protein A modified surfaces were regenerated using two 6-second pulses 100 mM phosphoric acid. Available binding data sets were fit to a 1:1 interaction model (CLAMP™). The rate constants and their ratio ($K_D=k_d/k_a$) and the error of fit carried over the estimate of the apparent equilibrium constants were calculated.

TLR3 capture analysis was performed at 25° C. using a Biacore 3000 biosensor equipped with a CM5 chip with surfaces modified with anti-His antibody (R&D Systems) (10,000 RU) at 30° C. by standard amine coupling. Human hexahistidine-TLR3 at 80, 120, and 300 RU density was captured on three surfaces while a fourth surface was used as reference. Antibody was injected in duplicate at 0, 0.4 1.1, 3.3, 10, and 30 nM. Association phases were monitored for three minutes and the dissociations were monitored for seven minutes. The anti-His antibody surfaces were regenerated using two 3-second pulses 50 mM phosphoric acid. Available binding data sets were fit to a 1:1 interaction model (BIAeval™) corrected for different drifts of each mAb-concentration profile. The rate constants and their ratio ($K_D=k_d/k_a$) and the error of fit carried over the estimate of the apparent equilibrium constants were calculated.

The calculated $K_D$ results are shown in Table 8 below. The two measurements represent 1) the binding affinity with anti-TLR3 mAb captured on the chip surface with human TLR3 applied in solution and 2) TLR3 captured on the chip surface and anti-TLR3 mAb applied in solution phase. The results indicate that that all of the candidates retain nM affinity when solution based TLR3 is captured by immobilized mAb confirming that the combinatorial mAbs have retained the binding characteristics of 1068. When TLR3 is immobilized on the chip most of the candidates retain the tight binding characteristics, a result that is consistent with the ELISA binding curves.

TABLE 8

Calculated $K_D$ values for combinatorial mAbs.

| mAb | $K_D$ with mAb capture | $K_D$ with TLR3 capture |
|---|---|---|
| 1068 (mIgG1) | 1.2 ± 0.7 nM | 0.316 ± 0.06 nM |
| HV5/LV5 | 1.1 nM | 0.7 ± 0.001 nM |
| HV5/LV1 | 2.0 nM | 0.65 ± 0.07 nM |
| HV1/LV1 | 3.9 nM | 1.7 ± 1.2 nM |
| HV4/LV3 | 0.5 nM | 3.4 ± 2.8 nM |
| HV1/LV7 | 7.2 nM | 90 ± 18 nM |

Binding activity of the human-adapted anti-TLR3 mAbs assayed by Biacore was also determined in a cell-based cytokine release assay. The human lung epithelial cell line BEAS-2B was plated in a 96-well plate and either poly(I:C) or poly(I:C) pre-incubated with an antibody candidate in a serum-free matrix was added to the cells. After 4 days, conditioned medium was removed and soluble cytokine levels were measured by Luminex® technology. The results are shown in FIG. 25 and demonstrate that biological activity of the parental mAb C1068, i.e., neutralization of TLR3 activity as measured by a decrease in pro-inflammatory cytokine generation by cells challenged with the TLR3 ligand poly(I:C), is retained in the human-adapted mAbs.

Example 21

Generation and Characterization of Human-Adapted C1068 Heavy and Light Chain Variants In silico immunogenicity analysis of the murine anti-TLR3 mAb 1068 CDRs revealed a series of aggretopes within the CDR boundaries that could be manipulated to reduce the immunogenicity score of the sequence. Once regions that could be manipulated were identified, both sequence and structural criteria were applied to decide what amino acid substitutions should be used. Using these criteria, four single point-amino acid substitutions were identified in the heavy chain variable region ($V_H$) and three mutations (a single, a double and a triple) were identified in the light chain variable region (Vκ). All eight mutations were made independently in the HV1/LV1 background and are listed in Table 9. One other type of substitution was also applied to determine the effect of changing the M102 residue to an isoleucine, this was completed to reduce the overall number of methionines in the CDRs as these residues can be post-translationally oxidized a modification potentially detrimental to the solubility of proteins. These antibodies were generated and assessed for TLR3 binding (see Tables 10 and 11) and bioactivity (see FIGS. 26-30) as described above.

TABLE 9

Location and identity of CDR point mutations

| Location | Variant Number | SEQ ID NO: |
|---|---|---|
| Vh CDR1 134M | HBV1 | 45 |
| Vh CDR2 Y60G | HBV2 | 47 |
| Vh CDR2 N61A | HBV3 | 49 |

TABLE 9-continued

Location and identity of CDR point mutations

| Location | Variant Number | SEQ ID NO: |
|---|---|---|
| Vh CDR2 F64G | HBV4 | 51 |
| Vh CDR3 M102I | HBV5 | 53 |
| Vκ CDR1 H30S | HBV6 | 55 |
| Vκ H30S/N31S | HBV7 | 57 |
| Vκ CDR1 H30S/N31S/N28G | HBV8 | 59 |

TABLE 10

Calculated $EC_{50}$ for Vh CDR variants in TLR3 binding assay.

| Variant | HBV1 | HBV2 | HBV3 | HBV4 | HBV5 |
|---|---|---|---|---|---|
| $EC_{50}$ (ng/ml) | 17 | 14.6 | 48 | 40.9 | 74.7 |

TABLE 11

Calculated $EC_{50}$ for Vκ CDR variants in TLR3 binding assay.

| | Variant | | |
|---|---|---|---|
| | HBV6 | HBV7 | HBV8 |
| $EC_{50}$ (ng/ml) | 1223 | >5000 | >5000 |

All five single point mutations made in the Vh of the 1068 CDRs grafted into the HV1/LV1 background were well tolerated as indicated by the binding EC50 against human TLR3. The $EC_{50}$ of the HV1/LV1 background was measured at 29.2 ng/ml; the values for both I34M and Y60G were lower than this, 17 and 14.6 ng/ml, respectively. This suggests that these changes not only reduce in silico immunogenecity of HV1/LV1 but also improve the binding to TLR3. The other three mutations bound a little weaker than HV1/LV1.

None of the mutations in the CDR1 of the Vl were tolerated ($EC_{50}$>1000 ng/ml) suggesting that this region is crucial for how 1068 recognizes human TLR3.

The present invention now being fully described, it will be apparent to one of ordinary skill in the art that many changes and modifications can be made thereto without departing from the spirit or scope of the appended claims.

The invention claimed is:

1. A method of treating an inflammatory condition comprising administering a therapeutically effective amount of a Toll Like Receptor 3 (TLR3) antagonist antibody to a patient in need thereof for a time sufficient to treat the inflammatory condition wherein the TLR3 antagonist antibody is an isolated antibody reactive with TLR3 comprising the amino acid sequences of the heavy chain complementarity determining regions (CDRs) of SEQ ID NOs: 9, 11 and 13 and the amino acid sequences of the light chain CDRs of SEQ ID NOs: 19, 21 and 23.

2. The method of claim 1 wherein the inflammatory condition is a sepsis-associated condition.

3. The method of claim 1 wherein the inflammatory condition is an inflammatory bowel disease.

4. The method of claim 1 wherein the inflammatory condition is an infection-associated condition.

5. The method of claim 1 wherein the inflammatory condition is an inflammatory pulmonary condition.

6. The method of claim 1 wherein the inflammatory condition is type 2 diabetes, dislipidemia or metabolic syndrome.

7. The method of claim 1 wherein the inflammatory condition is caused by an autoimmune disease.

8. A method of treating condition resulting from inflammation-induced cell death comprising administering a therapeutically effective amount of a TLR3 antibody antagonist to a patient in need thereof for a time sufficient to treat the condition wherein the TLR3 antagonist antibody is an isolated antibody reactive with TLR3 comprising the amino acid sequences of the heavy chain complementarity determining regions (CDRs) of SEQ ID NOs: 9, 11 and 13 and the amino acid sequences of the light chain CDRs of SEQ ID NOs: 19, 21 and 23.

9. The method of claim 1 or 8 wherein the isolated antibody comprises a variable heavy chain ($V_H$) having the amino acid sequence shown in SEQ ID NO: 6, 25, 27, 29 or 31 and a variable light chain ($V_L$) chain having the amino acid sequence shown in SEQ ID NO: 16, 33, 35, 37 or 39.

* * * * *

UNITED STATES PATENT AND TRADEMARK OFFICE
CERTIFICATE OF CORRECTION

PATENT NO. : 8,153,583 B2
APPLICATION NO. : 11/291140
DATED : April 10, 2012
INVENTOR(S) : Carton et al.

Page 1 of 1

It is certified that error appears in the above-identified patent and that said Letters Patent is hereby corrected as shown below:

On the Title page, item (60), please delete:
"Related U.S. Application Data

(60) Provisional application No. 60/631,815, filed on Nov. 30, 2004, provisional application No. 60/639,399, filed on Dec. 15, 2004, provisional application No. 60/641,877, filed on Jan. 6, 2005, provisional application No. 60/713,195, filed on Aug. 31, 2005, provisional application No. 60/727,610, filed on Oct. 18, 2005."

and substitute therefor:

--Related U.S. Application Data

(60) Provisional application No. 60/631,815, filed on Nov. 30, 2004, provisional application No. 60/636,399, filed on Dec. 15, 2004, provisional application No. 60/641,877, filed on Jan. 6, 2005, provisional application No. 60/713,195, filed on Aug. 31, 2005, provisional application No. 60/727,610, filed on Oct. 18, 2005.--

Signed and Sealed this
Sixth Day of November, 2012

David J. Kappos
*Director of the United States Patent and Trademark Office*

SEQUENCE LISTING

<160> NUMBER OF SEQ ID NOS: 63

<210> SEQ ID NO 1
<211> LENGTH: 2712
<212> TYPE: DNA
<213> ORGANISM: Homo sapiens

<400> SEQUENCE: 1

```
atgagacaga ctttgccttg tatctacttt tggggggggcc ttttgccctt tgggatgctg      60
tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
gatgtaggat ttaacaccat ctcaaaactg gagccagaat tgtgccagaa acttcccatg     300
ttaaaagttt tgaacctcca gcacaatgag ctatctcaac tttctgataa aacctttgcc     360
ttctgcacga atttgactga actccatctc atgtccaact caatccagaa aattaaaaat     420 aatcccttttg tcaagcagaa gaatttaatc acattagatc tgtctcataa tggcttgtca     480
tctacaaaat taggaactca ggttcagctg gaaaatctcc aagagcttct attatcaaac     540
aataaaattc aagcgctaaa aagtgaagaa ctggatatct ttgccaattc atcctttaaaa    600 aaattagagt tgtcatcgaa tcaaattaaa gagttttctc cagggtgttt tcacgcaatt     660
ggaagattat ttggcctctt tctgaacaat gtccagctgg gtcccagcct tacagagaag     720
ctatgtttgg aattagcaaa cacaagcatt cggaatctgt ctctgagtaa cagccagctg     780
tccaccacca gcaatacaac tttcttggga ctaaagtgga caaatctcac tatgctcgat     840 cttttcctaca acaacttaaa tgtggttggt aacgattcct tgcttggct tccacaacta    900 gaatatttct tcctagagta taataatata cagcatttgt ttttctcactc tttgcacggg    960 cttttcaatg tgaggtacct gaatttgaaa cggtctttta ctaaacaaag tatttccctt   1020
gcctcactcc ccaagattga tgatttttct tttcagtggc taaatgttt ggagcacctt    1080 aacatggaag ataatgatat tccaggcata aaaagcaata tgttcacagg attgataaac   1140
```

-continued

```
ctgaaatact taagtctatc caactccttt acaagtttgc gaactttgac aaatgaaaca 1200
tttgtatcac ttgctcattc tcccttacac atactcaacc taaccaagaa taaaatctca 1260
aaaatagaga gtgatgcttt ctcttggttg ggccacctag aagtacttga cctgggcctt 1320
aatgaaattg ggcaagaact cacaggccag gaatggagag gtctagaaaa tattttcgaa 1380
atctatcttt cctacaacaa gtacctgcag ctgactagga actcctttgc cttggtccca 1440
agccttcaac gactgatgct ccgaagggtg gcccttaaaa atgtggatag ctctccttca 1500
ccattccagc ctcttcgtaa cttgaccatt ctggatctaa gcaacaacaa catagccaac 1560
ataaatgatg acatgttgga gggtcttgag aaactagaaa ttctcgattt gcagcataac 1620
aacttagcac ggctctggaa acacgcaaac cctggtggtc ccatttattt cctaaagggt 1680
ctgtctcacc tccacatcct taacttggag tccaacggct ttgacgagat cccagttgag 1740
```

```

gtcttcaagg atttatttga actaaagatc atcgatttag gattgaataa tttaaacaca 1800
cttccagcat ctgtctttaa taatcaggtg tctctaaagt cattgaacct tcagaagaat 1860
ctcataacat ccgttgagaa gaaggttttc gggccagctt tcaggaacct gactgagtta 1920
gatatgcgct ttaatccctt tgattgcacg tgtgaaagta ttgcctggtt tgttaattgg 1980
attaacgaga cccataccaa catccctgag ctgtcaagcc actacctttg caacactcca 2040
cctcactatc atgggttccc agtgagactt tttgatacat catcttgcaa agacagtgcc 2100
ccctttgaac tctttttcat gatcaatacc agtatcctgt tgatttttat ctttattgta 2160
cttctcatcc actttgaggg ctggaggata tctttttatt ggaatgtttc agtacatcga 2220
gttcttggtt tcaaagaaat agacagacag acagaacagt ttgaatatgc agcatatata 2280
attcatgcct ataaagataa ggattgggtc tgggaacatt tctcttcaat ggaaaaggaa 2340
gaccaatctc tcaaattttg tctggaagaa agggactttg aggcgggtgt ttttgaacta 2400
gaagcaattg ttaacagcat caaaagaagc agaaaaatta tttttgttat aacacaccat 2460
ctattaaaag acccattatg caaaagattc aaggtacatc atgcagttca acaagctatt 2520
gaacaaaatc tggattccat tatattggtt ttccttgagg agattccaga ttataaactg 2580
aaccatgcac tctgtttgcg aagaggaatg tttaaatctc actgcatctt gaactggcca 2640
gttcagaaag aacggatagg tgcctttcgt cataaattgc aagtagcact tggatccaaa 2700
aactctgtac at 2712
```

<210> SEQ ID NO 2
<211> LENGTH: 904
<212> TYPE: PRT
<213> ORGANISM: Homo sapiens

<400> SEQUENCE: 2

```
Met Arg Gln Thr Leu Pro Cys Ile Tyr Phe Trp Gly Gly Leu Leu Pro
1 5 10 15

Phe Gly Met Leu Cys Ala Ser Ser Thr Thr Lys Cys Thr Val Ser His
20 25 30

Glu Val Ala Asp Cys Ser His Leu Lys Leu Thr Gln Val Pro Asp Asp
35 40 45

Leu Pro Thr Asn Ile Thr Val Leu Asn Leu Thr His Asn Gln Leu Arg
50 55 60

Arg Leu Pro Ala Ala Asn Phe Thr Arg Tyr Ser Gln Leu Thr Ser Leu
65 70 75 80

Asp Val Gly Phe Asn Thr Ile Ser Lys Leu Glu Pro Glu Leu Cys Gln
85 90 95
```

```
Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
            130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
            195                 200                 205

Ile Lys Glu Phe Ser Pro Gly Cys Phe His Ala Ile Gly Arg Leu Phe
            210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Gln Leu Glu Tyr Phe Phe
            290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
            370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
            450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
```

```
                515                 520                 525
Leu Glu Lys Leu Glu Ile Leu Asp Leu Gln His Asn Asn Leu Ala Arg
            530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
                580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
            690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
            850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 3
<211> LENGTH: 2109
<212> TYPE: DNA
<213> ORGANISM: Homo sapiens
```

```
<400> SEQUENCE: 3
atgagacaga ctttgccttg tatctacttt tggggggggcc ttttgcccttt tgggatgctg      60 tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
gatgtaggat ttaacaccat ctcaaaactg gagccagaat tgtgcagaa acttcccatg      300 ttaaaagttt tgaacctcca gcacaatgag ctatctcaac tttctgataa aacctttgcc     360
ttctgcacga atttgactga actccatctc atgtccaact caatccagaa aattaaaaat     420
aatccctttg tcaagcagaa gaatttaatc acattagatc tgtctcataa tggcttgtca     480
tctacaaaat taggaactca ggttcagctg gaaaatctcc aagagcttct attatcaaac     540
aataaaattc aagcgctaaa aagtgaagaa ctggatatct ttgccaattc atctttaaaa     600
aaattagagt tgtcatcgaa tcaaattaaa gagttttctc cagggtgttt tcacgcaatt     660
ggaagattat ttggcctctt tctgaacaat gtccagctgg gtcccagcct tacagagaag     720
ctatgtttgg aattagcaaa cacaagcatt cggaatctgt ctctgagtaa cagccagctg     780
tccaccacca gcaatacaac tttcttggga ctaaagtgga caaatctcac tatgctcgat     840 cttttcctaca caacttaaa tgtggttggt aacgattcct ttgcttggct tccacaacta     900
gaatatttct tcctagagta ataatatata cagcatttgt tttctcactc tttgcacggg     960
cttttcaatg tgaggtacct gaatttgaaa cggtctttta ctaaacaaag tatttccctt    1020
gcctcactcc ccaagattga tgattttct tttcagtggc taaaatgttt ggagcacctt     1080
aacatggaag ataatgatat tccaggcata aaaagcaata tgttcacagg attgataaac    1140
ctgaaatact taagtctatc caactccttt acaagtttgc gaactttgac aaatgaaaca    1200
tttgtatcac ttgctcattc tcccttacac atactcaacc taaccaagaa taaaatctca    1260
aaaatagaga gtgatgcttt ctcttggttg ggccacctag aagtacttga cctgggcctt    1320
aatgaaattg ggcaagaact cacaggccag gaatggagag gtctagaaaa tattttcgaa    1380
atctatcttt cctacaacaa gtacctgcag ctgactagga actcctttgc cttggtccca    1440
agccttcaac gactgatgct ccgaaggggtg gcccttaaaa atgtggatag ctctccttca    1500
ccattccagc ctcttcgtaa cttgaccatt ctggatctaa gcaacaacaa catagccaac    1560
ataaatgatg acatgttgga gggtcttgag aaactagaaa ttctcgattt gcagcataac    1620
aacttagcac ggctctggaa acacgcaaac cctggtggtc ccatttattt cctaaagggt    1680
ctgtctcacc tccacatcct taacttggag tccaacggct ttgacgagat cccagttgag    1740
gtcttcaagg atttatttga actaaagatc atcgatttag gattgaataa tttaaacaca    1800
cttccagcat ctgtctttaa taatcaggtg tctctaaagt cattgaacct tcagaagaat    1860
ctcataacat ccgttgagaa gaaggttttc gggccagctt tcaggaacct gactgagtta    1920
gatatgcgct ttaatccctt tgattgcacg tgtgaaagta ttgcctggtt tgttaattgg    1980
attaacgaga cccataccaa catccctgag ctgtcaagcc actacctttg caacactcca    2040
cctcactatc atgggttccc agtgagactt tttgatacat catcttgcaa agacagtgcc    2100
cccttttgaa                                                            2109

<210> SEQ ID NO 4
<211> LENGTH: 703
<212> TYPE: PRT
<213> ORGANISM: Homo sapiens
```

<400> SEQUENCE: 4

```
Met Arg Gln Thr Leu Pro Cys Ile Tyr Phe Trp Gly Gly Leu Leu Pro
 1               5                  10                  15

Phe Gly Met Leu Cys Ala Ser Ser Thr Thr Lys Cys Thr Val Ser His
             20                  25                  30

Glu Val Ala Asp Cys Ser His Leu Lys Leu Thr Gln Val Pro Asp Asp
         35                  40                  45

Leu Pro Thr Asn Ile Thr Val Leu Asn Leu Thr His Asn Gln Leu Arg
     50                  55                  60

Arg Leu Pro Ala Ala Asn Phe Thr Arg Tyr Ser Gln Leu Thr Ser Leu
 65                  70                  75                  80

Asp Val Gly Phe Asn Thr Ile Ser Lys Leu Glu Pro Glu Leu Cys Gln
                 85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415
```

```
Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu
    690                 695                 700

<210> SEQ ID NO 5
<211> LENGTH: 381
<212> TYPE: DNA
<213> ORGANISM: Mus musculus

<400> SEQUENCE: 5
atgagtgtgc tcactcaggt cctggcgttg ctgctgctgt ggcttacagg tgccagatgt     60
gacatccaga tgactcagtc tccagcctcc ctatctgcat ctgtgggaga aactgtcacc    120
atcacatgtc gagcaagtgg gaatattcac aattatttag catggtatca gcagaaacag    180
ggaaaatctc ctcagctcct ggtctataat gcaaaaacct tagcagatgg tgtgccatca    240
agattcagtg gcagtgaatc aggaacacaa tattctctca gatcaacag cctgcagcct    300 gaagattttg ggagttatta ctgtcaacat ttttggagta ctccatttac gttcggctcg    360
gggacaaagt tggaactaaa a                                              381

<210> SEQ ID NO 6
<211> LENGTH: 138
<212> TYPE: PRT
```

<213> ORGANISM: Mus musculus

<400> SEQUENCE: 6

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Gln
            20                  25                  30

Pro Gly Thr Ser Val Arg Leu Ser Cys Lys Ala Ser Gly Tyr Ile Phe
        35                  40                  45

Thr Thr Tyr Trp Ile His Trp Val Lys Gln Arg Pro Gly Gln Gly Leu
    50                  55                  60

Glu Trp Ile Gly Glu Ile Asn Pro Asn Asn Gly Arg Ile Asn Tyr Asn
65                  70                  75                  80

Glu Lys Phe Lys Thr Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Thr Arg Val Gly Val Met Ile Thr Thr Phe Pro Tyr Trp
        115                 120                 125

Gly Gln Gly Thr Leu Val Thr Val Ser Ala
    130                 135

<210> SEQ ID NO 7
<211> LENGTH: 19
<212> TYPE: PRT
<213> ORGANISM: Mus musculus

<400> SEQUENCE: 7

Met Gly Trp Ser Tyr Ile Ile Leu Phe Leu Val Ala Thr Ala Thr Asp
1               5                   10                  15

Val His Ser

<210> SEQ ID NO 8
<211> LENGTH: 29
<212> TYPE: PRT
<213> ORGANISM: Mus musculus

<400> SEQUENCE: 8

Gln Val Gln Leu Gln Gln Pro Gly Ala Glu Leu Val Gln Pro Gly Thr
1               5                   10                  15

Ser Val Arg Leu Ser Cys Lys Ala Ser Gly Tyr Ile Phe
            20                  25

<210> SEQ ID NO 9
<211> LENGTH: 6
<212> TYPE: PRT
<213> ORGANISM: Mus musculus

<400> SEQUENCE: 9

Thr Thr Tyr Trp Ile His
1               5

<210> SEQ ID NO 10
<211> LENGTH: 14
<212> TYPE: PRT
<213> ORGANISM: Mus musculus

<400> SEQUENCE: 10

Trp Val Lys Gln Arg Pro Gly Gln Gly Leu Glu Trp Ile Gly
1               5                   10

<210> SEQ ID NO 11
<211> LENGTH: 17
<212> TYPE: PRT
<213> ORGANISM: Mus musculus

<400> SEQUENCE: 11

Glu Ile Asn Pro Asn Asn Gly Arg Ile Asn Tyr Asn Glu Lys Phe Lys
1               5                   10                  15

Thr

<210> SEQ ID NO 12
<211> LENGTH: 32
<212> TYPE: PRT
<213> ORGANISM: Mus musculus

<400> SEQUENCE: 12

Lys Ala Thr Leu Thr Val Asp Lys Ser Ser Thr Ala Tyr Met Gln
1               5                   10                  15

Leu Ser Ser Leu Thr Ser Glu Asp Ser Ala Val Tyr Tyr Cys Thr Arg
            20                  25                  30

<210> SEQ ID NO 13
<211> LENGTH: 10
<212> TYPE: PRT
<213> ORGANISM: Mus musculus

<400> SEQUENCE: 13

Val Gly Val Met Ile Thr Thr Phe Pro Tyr
1               5                   10

<210> SEQ ID NO 14
<211> LENGTH: 11
<212> TYPE: PRT
<213> ORGANISM: Mus musculus

<400> SEQUENCE: 14

Trp Gly Gln Gly Thr Leu Val Thr Val Ser Ala
1               5                   10

<210> SEQ ID NO 15
<211> LENGTH: 381
<212> TYPE: DNA
<213> ORGANISM: Mus musculus

<400> SEQUENCE: 15
atgagtgtgc tcactcaggt cctggcgttg ctgctgctgt ggcttacagg tgccagatgt      60
gacatccaga tgactcagtc tccagcctcc ctatctgcat ctgtgggaga aactgtcacc     120
atcacatgtc gagcaagtgg gaatattcac aattatttag catggtatca gcagaaacag     180
ggaaaatctc ctcagctcct ggtctataat gcaaaaacct tagcagatgg tgtgccatca     240
agattcagtg gcagtgaatc aggaacacaa tattctctca gatcaacag cctgcagcct      300 gaagattttg ggagttatta ctgtcaacat ttttggagta ctccatttac gttcggctcg     360
gggacaaagt tggaactaaa a                                               381

<210> SEQ ID NO 16
<211> LENGTH: 127
<212> TYPE: PRT
<213> ORGANISM: Mus musculus

<400> SEQUENCE: 16

Met Ser Val Leu Thr Gln Val Leu Ala Leu Leu Leu Leu Trp Leu Thr

```
                1               5                  10                 15
Gly Ala Arg Cys Asp Ile Gln Met Thr Gln Ser Pro Ala Ser Leu Ser
            20                 25                 30

Ala Ser Val Gly Glu Thr Val Thr Ile Thr Cys Arg Ala Ser Gly Asn
            35                 40                 45

Ile His Asn Tyr Leu Ala Trp Tyr Gln Gln Lys Gln Gly Lys Ser Pro
            50                 55                 60

Gln Leu Leu Val Tyr Asn Ala Lys Thr Leu Ala Asp Gly Val Pro Ser
65                  70                 75                 80

Arg Phe Ser Gly Ser Glu Ser Gly Thr Gln Tyr Ser Leu Lys Ile Asn
                85                 90                 95

Ser Leu Gln Pro Glu Asp Phe Gly Ser Tyr Tyr Cys Gln His Phe Trp
            100                105                110

Ser Thr Pro Phe Thr Phe Gly Ser Gly Thr Lys Leu Glu Leu Lys
            115                120                125
```

<210> SEQ ID NO 17
<211> LENGTH: 20
<212> TYPE: PRT
<213> ORGANISM: Mus musculus

<400> SEQUENCE: 17

```
Met Ser Val Leu Thr Gln Val Leu Ala Leu Leu Leu Leu Trp Leu Thr
1               5                  10                 15

Gly Ala Arg Cys
            20
```

<210> SEQ ID NO 18
<211> LENGTH: 23
<212> TYPE: PRT
<213> ORGANISM: Mus musculus

<400> SEQUENCE: 18

```
Asp Ile Gln Met Thr Gln Ser Pro Ala Ser Leu Ser Ala Ser Val Gly
1               5                  10                 15

Glu Thr Val Thr Ile Thr Cys
            20
```

<210> SEQ ID NO 19
<211> LENGTH: 11
<212> TYPE: PRT
<213> ORGANISM: Mus musculus

<400> SEQUENCE: 19

```
Arg Ala Ser Gly Asn Ile His Asn Tyr Leu Ala
1               5                  10
```

<210> SEQ ID NO 20
<211> LENGTH: 15
<212> TYPE: PRT
<213> ORGANISM: Mus musculus

<400> SEQUENCE: 20

```
Trp Tyr Gln Gln Lys Gln Gly Lys Ser Pro Gln Leu Leu Val Tyr
1               5                  10                 15
```

<210> SEQ ID NO 21
<211> LENGTH: 7
<212> TYPE: PRT
<213> ORGANISM: Mus musculus

<400> SEQUENCE: 21

Asn Ala Lys Thr Leu Ala Asp
1               5

<210> SEQ ID NO 22
<211> LENGTH: 32
<212> TYPE: PRT
<213> ORGANISM: Mus musculus

<400> SEQUENCE: 22

Gly Val Pro Ser Arg Phe Ser Gly Ser Glu Ser Gly Thr Gln Tyr Ser
1               5                   10                  15

Leu Lys Ile Asn Ser Leu Gln Pro Glu Asp Phe Gly Ser Tyr Tyr Cys
            20                  25                  30

<210> SEQ ID NO 23
<211> LENGTH: 7
<212> TYPE: PRT
<213> ORGANISM: Mus musculus

<400> SEQUENCE: 23

Gln His Phe Trp Ser Thr Pro
1               5

<210> SEQ ID NO 24
<211> LENGTH: 12
<212> TYPE: PRT
<213> ORGANISM: Mus musculus

<400> SEQUENCE: 24

Phe Thr Phe Gly Ser Gly Thr Lys Leu Glu Leu Lys
1               5                   10

<210> SEQ ID NO 25
<211> LENGTH: 119
<212> TYPE: PRT
<213> ORGANISM: Artificial Sequence
<220> FEATURE:
<223> OTHER INFORMATION: Human-adapted heavy chain HV1

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile His Trp Val Arg Gln Ala Pro Gly Gln Arg Leu Glu Trp Met
        35                  40                  45

Gly Glu Ile Asn Pro Asn Asn Gly Arg Ile Asn Tyr Asn Glu Lys Phe
    50                  55                  60

Lys Thr Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Val Met Ile Thr Thr Phe Pro Tyr Trp Gly Gln Gly
            100                 105                 110

Thr Leu Val Thr Val Ser Ser
        115

<210> SEQ ID NO 26
<211> LENGTH: 357
<212> TYPE: DNA
<213> ORGANISM: Artificial Sequence
<220> FEATURE:

<223> OTHER INFORMATION: Human-adapted heavy chain HV1

<400> SEQUENCE: 26

```
caggtgcagc tggtgcagag cggcgcggaa gtgaaaaaac cgggcgcgag cgtgaaagtg      60
agctgcaaag cgagcggcta cctttacc acctattgga ttcattgggt gcgccaggcg      120
ccgggccagc gcctggaatg gatgggcgaa attaacccga caacggccg cattaactat      180
aacgaaaaat ttaaaacccg cgtgaccatt acccgcgata ccagcgcgag caccgcgtat      240
atggaactga gcagcctgcg cagcgaagat accgcggtgt attattgcgc gcgcgtgggc      300
gtgatgatta ccacctttcc gtattggggc cagggcaccc tggtgaccgt gagcagc        357
```

<210> SEQ ID NO 27
<211> LENGTH: 119
<212> TYPE: PRT
<213> ORGANISM: Artificial Sequence
<220> FEATURE:
<223> OTHER INFORMATION: Human-adapted heavy chain HV4

<400> SEQUENCE: 27

```
Gln Val Gln Leu Val Gln Ser Gly Ala Glu Val Lys Lys Pro Gly Ala
 1               5                   10                  15
Ser Val Lys Val Ser Cys Lys Ala Ser Gly Tyr Thr Phe Thr Thr Tyr
            20                  25                  30
Trp Ile His Trp Val Arg Gln Ala Pro Gly Gln Gly Leu Glu Trp Met
        35                  40                  45
Gly Glu Ile Asn Pro Asn Asn Gly Arg Ile Asn Tyr Asn Glu Lys Phe
    50                  55                  60
Lys Thr Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Val Gly Val Met Ile Thr Thr Phe Pro Tyr Trp Gly Gln Gly
            100                 105                 110
Thr Leu Val Thr Val Ser Ser
        115
```

<210> SEQ ID NO 28
<211> LENGTH: 357
<212> TYPE: DNA
<213> ORGANISM: Artificial Sequence
<220> FEATURE:
<223> OTHER INFORMATION: Human-adapted heavy chain HV4

<400> SEQUENCE: 28

```
caggtgcagc tggtgcagag cggcgcggaa gtgaaaaaac cgggcgcgag cgtgaaagtg      60
agctgcaaag cgagcggcta cctttacc acctattgga ttcattgggt gcgccaggcg      120
ccgggccagg gcctggaatg gatgggcgaa attaacccga caacggccg cattaactat      180
aacgaaaaat ttaaaacccg cgtgaccatg acccgcgata ccagcattag caccgcgtat      240
atggaactga gcgcctgcg cagcgatgat accgcggtgt attattgcgc gcgcgtgggc      300
gtgatgatta ccacctttcc gtattggggc cagggcaccc tggtgaccgt gagcagc        357
```

<210> SEQ ID NO 29
<211> LENGTH: 119
<212> TYPE: PRT
<213> ORGANISM: Artificial Sequence
<220> FEATURE:
<223> OTHER INFORMATION: Human-adapted heavy chain HV5

<400> SEQUENCE: 29

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
             20                  25                  30

Trp Ile His Trp Val Arg Gln Ala Thr Gly Gln Gly Leu Glu Trp Met
         35                  40                  45

Gly Glu Ile Asn Pro Asn Asn Gly Arg Ile Asn Tyr Asn Glu Lys Phe
     50                  55                  60

Lys Thr Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Gly Val Met Ile Thr Thr Phe Pro Tyr Trp Gly Gln Gly
            100                 105                 110

Thr Leu Val Thr Val Ser Ser
        115

<210> SEQ ID NO 30
<211> LENGTH: 357
<212> TYPE: DNA
<213> ORGANISM: Artificial Sequence
<220> FEATURE:
<223> OTHER INFORMATION: Human-adapted heavy chain HV5

<400> SEQUENCE: 30
caggtgcagc tggtgcagag cggcgcggaa gtgaaaaaac cgggcgcgag cgtgaaagtg     60
agctgcaaag cgagcggcta cctttacc acctattgga ttcattgggt gcgccaggcg    120
accggccagg gcctggaatg gatgggcgaa attaacccga caacggccg cattaactat    180 aacgaaaaat ttaaaacccg cgtgaccatg acccgcaaca ccagcattag caccgcgtat    240
atggaactga gcagcctgcg cagcgaagat accgcggtgt attattgcgc gcgcgtgggc    300
gtgatgatta ccacctttcc gtattggggc cagggcaccc tggtgaccgt gagcagc       357

<210> SEQ ID NO 31
<211> LENGTH: 119
<212> TYPE: PRT
<213> ORGANISM: Artificial Sequence
<220> FEATURE:
<223> OTHER INFORMATION: Human-adapted heavy chain HV7

<400> SEQUENCE: 31

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Thr Tyr
             20                  25                  30

Trp Ile His Trp Val Arg Gln Ala Pro Gly Gln Gly Leu Glu Trp Met
         35                  40                  45

Gly Glu Ile Asn Pro Asn Asn Gly Arg Ile Asn Tyr Asn Glu Lys Phe
     50                  55                  60

Lys Thr Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Gly Val Met Ile Thr Thr Phe Pro Tyr Trp Gly Arg Gly
            100                 105                 110

Thr Leu Val Thr Val Ser Ser

<210> SEQ ID NO 32
<211> LENGTH: 357
<212> TYPE: DNA
<213> ORGANISM: Artificial Sequence
<220> FEATURE:
<223> OTHER INFORMATION: Human-adapted heavy chain HV7

<400> SEQUENCE: 32

```
caggtgcagc tggtgcagag cggcgcggaa gtgaaaaaac cgggcagcag cgtgaaagtg      60
agctgcaaag cgagcggcgg cacctttagc acctattgga ttcattgggt cgccaggcg     120
ccgggccagg gcctggaatg gatgggcgaa attaaccega caacggccg cattaactat     180
aacgaaaaat ttaaaacccg cgtgaccatt accgcggatg aaagcaccag caccgcgtat     240
atggaactga gcagcctgcg cagcgaagat accgcggtgt attattgcgc gcgcgtgggc     300
gtgatgatta ccacctttcc gtattggggc cgcggcaccc tggtgaccgt gagcagc        357
```

<210> SEQ ID NO 33
<211> LENGTH: 107
<212> TYPE: PRT
<213> ORGANISM: Artificial Sequence
<220> FEATURE:
<223> OTHER INFORMATION: Human-adapted light chain LV1

<400> SEQUENCE: 33

Asp Ile Gln Met Thr Gln Ser Pro Ser Ser Leu Ser Ala Ser Val Gly
1               5                   10                  15
Asp Arg Val Thr Ile Thr Cys Arg Ala Ser Gly Asn Ile His Asn Tyr
            20                  25                  30
Leu Ala Trp Tyr Gln Gln Lys Pro Gly Lys Ala Pro Lys Leu Leu Ile
        35                  40                  45
Tyr Asn Ala Lys Thr Leu Ala Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln His Phe Trp Ser Thr Pro Phe
                85                  90                  95
Thr Phe Gly Gln Gly Thr Lys Leu Glu Ile Lys
            100                 105

<210> SEQ ID NO 34
<211> LENGTH: 321
<212> TYPE: DNA
<213> ORGANISM: Artificial Sequence
<220> FEATURE:
<223> OTHER INFORMATION: Human-adapted light chain LV1

<400> SEQUENCE: 34

```
gatattcaga tgacccagag cccgagcagc ctgagcgcga gcgtgggcga tcgcgtgacc      60
attacctgcc gcgcgagcgg caacattcat aactatctgg cgtggtatca gcagaaaccg     120
ggcaaagcgc cgaaactgct gatttataac gcgaaaaccc tggcggatgg cgtgccgagc     180
cgctttagcg gcagcggcag cggcaccgat tttaccctga ccattagcag cctgcagccg     240
gaagattttg cgacctatta ttgccagcat ttttggagca ccccgtttac ctttggccag     300
ggcaccaaac tggaaattaa a                                              321
```

<210> SEQ ID NO 35
<211> LENGTH: 107

```
<212> TYPE: PRT
<213> ORGANISM: Artificial Sequence
<220> FEATURE:
<223> OTHER INFORMATION: Human-adapted light chain LV3

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Arg Leu Ile
        35                  40                  45

Tyr Asn Ala Lys Thr Leu Ala Asp Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Leu Glu Ile Lys
            100                 105

<210> SEQ ID NO 36
<211> LENGTH: 321
<212> TYPE: DNA
<213> ORGANISM: Artificial Sequence
<220> FEATURE:
<223> OTHER INFORMATION: Human-adapted light chain LV3

<400> SEQUENCE: 36
gatattcaga tgacccagag cccgagcagc ctgagcgcga gcgtgggcga tcgcgtgacc      60
attacctgcc gcgcgagcgg caacattcat aactatctgg cgtggtatca gcagaaaccg     120
ggcaaagcgc cgaaacgcct gatttataac gcgaaaaccc tggcggatgg cgtgccgagc     180
cgctttagcg gcagcggcag cggcaccgaa tttaccctga ccattagcag cctgcagccg     240
gaagattttg cgacctatta ttgccagcat ttttggagca cccgtttac  ctttggccag     300 ggcaccaaac tggaaattaa a                                               321

<210> SEQ ID NO 37
<211> LENGTH: 107
<212> TYPE: PRT
<213> ORGANISM: Artificial Sequence
<220> FEATURE:
<223> OTHER INFORMATION: Human-adapted light chain LV5

<400> SEQUENCE: 37

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Thr Pro Phe
                85                  90                  95

Thr Phe Gly Gly Gly Thr Lys Val Glu Ile Lys
            100                 105
```

<210> SEQ ID NO 38
<211> LENGTH: 321
<212> TYPE: DNA
<213> ORGANISM: Artificial Sequence
<220> FEATURE:
<223> OTHER INFORMATION: Human-adapted light chain LV5

<400> SEQUENCE: 38

```
gatattcaga tgacccagag cccgagcagc ctgagcgcga gcgtgggcga tcgcgtgacc      60
attacctgcc gcgcgagcgg caacattcat aactatctgg cgtggtatca gcagaaaccg    120
ggcaaagtgc cgaaactgct gatttataac gcgaaaaccc tggcggatgg cgtgccgagc    180
cgctttagcg gcagcggcag cggcaccgat tttaccctga ccattagcag cctgcagccg    240
gaagatgtgg cgacctatta ttgccagcat ttttggagca ccccgtttac ctttggcggc    300
ggcaccaaag tggaaattaa a                                              321
```

<210> SEQ ID NO 39
<211> LENGTH: 107
<212> TYPE: PRT
<213> ORGANISM: Artificial Sequence
<220> FEATURE:
<223> OTHER INFORMATION: Human-adapted light chain LV7

<400> SEQUENCE: 39

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gly Asn Ile His Asn Tyr
            20                  25                  30
Leu Ala Trp Phe Gln Gln Lys Pro Gly Lys Ala Pro Lys Ser Leu Ile
        35                  40                  45
Tyr Asn Ala Lys Thr Leu Ala Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln His Phe Trp Ser Thr Pro Phe
                85                  90                  95
Thr Phe Gly Gln Gly Thr Lys Leu Glu Ile Lys
            100                 105
```

<210> SEQ ID NO 40
<211> LENGTH: 321
<212> TYPE: DNA
<213> ORGANISM: Artificial Sequence
<220> FEATURE:
<223> OTHER INFORMATION: Human-adapted light chain LV7

<400> SEQUENCE: 40

```
gatattcaga tgacccagag cccgagcagc ctgagcgcga gcgtgggcga tcgcgtgacc      60
attacctgcc gcgcgagcgg caacattcat aactatctgg cgtggtttca gcagaaaccg    120
ggcaaagcgc cgaaaagcct gatttataac gcgaaaaccc tggcggatgg cgtgccgagc    180
cgctttagcg gcagcggcag cggcaccgat tttaccctga ccattagcag cctgcagccg    240
gaagattttg cgacctatta ttgccagcat ttttggagca ccccgtttac ctttggccag    300
ggcaccaaac tggaaattaa a                                              321
```

<210> SEQ ID NO 41
<211> LENGTH: 327
<212> TYPE: PRT

<213> ORGANISM: Artificial Sequence
<220> FEATURE:
<223> OTHER INFORMATION: Human IgG4 heavy chain constant region variant

<400> SEQUENCE: 41

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 42
<211> LENGTH: 981
<212> TYPE: DNA
<213> ORGANISM: Artificial Sequence
<220> FEATURE:
<223> OTHER INFORMATION: Human IgG4 heavy chain constant region variant

<400> SEQUENCE: 42

```
gcgagcacca aaggcccgag cgtgtttccg ctggcgccgt gcagccgcag caccagcgaa      60
```

```
agcaccgcgg cgctgggctg cctggtgaaa gattattttc cggaaccggt gaccgtgagc    120
tggaacagcg gcgcgctgac cagcggcgtg cataccttc cggcggtgct gcagagcagc    180
ggcctgtata gcctgagcag cgtggtgacc gtgccgagca gcagcctggg caccaaaacc    240
tatacctgca acgtggatca taaaccgagc aacaccaaag tggataaacg cgtggaaagc    300
aaatatggcc cgccgtgccc gccgtgcccg gcgccggaag cggcgggcgg cccgagcgtg    360
tttctgtttc cgccgaaacc gaaagatacc ctgatgatta gccgcacccc ggaagtgacc    420
tgcgtggtgg tggatgtgag ccaggaagat ccggaagtgc agtttaactg gtatgtggat    480
ggcgtggaag tgcataacgc gaaaaccaaa ccgcgcgaag aacagtttaa cagcacctat    540
cgcgtggtga gcgtgctgac cgtgctgcat caggattggc tgaacggcaa agaatataaa    600
tgcaaagtga gcaacaaagg cctgccgagc agcattgaaa aaaccattag caaagcgaaa    660
ggccagccgc gcgaaccgca ggtgtatacc ctgccgccga gccaggaaga aatgaccaaa    720
aaccaggtga gcctgacctg cctggtgaaa ggcttttatc cgagcgatat tgcggtggaa    780
tgggaaagca acggccagcc ggaaaacaac tataaaacca cccgccggt gctggatagc    840 gatggcagct ttttttctgta tagccgcctg accgtggata aaagccgctg gcaggaaggc    900
aacgtgttta gctgcagcgt gatgcatgaa gcgctgcata accattatac ccagaaaagc    960
ctgagcctga gcctgggcaa a                                             981

<210> SEQ ID NO 43
<211> LENGTH: 107
<212> TYPE: PRT
<213> ORGANISM: Artificial Sequence
<220> FEATURE:
<223> OTHER INFORMATION: Human k constant region

<400> SEQUENCE: 43

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 44
<211> LENGTH: 324
<212> TYPE: DNA
<213> ORGANISM: Artificial Sequence
<220> FEATURE:
<223> OTHER INFORMATION: Human k constant region

<400> SEQUENCE: 44
gcgcgcaccg tggcggcgcc gagcgtgttt atttttccgc cgagcgatga acagctgaaa    60
agcggcaccg cgagcgtggt gtgcctgctg aacaactttt atccgcgcga agcgaaagtg   120
cagtggaaag tggataacgc gctgcagagc ggcaacagcc aggaaagcgt gaccgaacag   180
```

```
gatagcaaag atagcaccta tagcctgagc agcaccctga ccctgagcaa agcggattat    240
gaaaaacata aagtgtatgc gtgcgaagtg acccatcagg gcctgagcag cccggtgacc    300
aaaagcttta accgcggcga atgc                                          324
```

<210> SEQ ID NO 45
<211> LENGTH: 119
<212> TYPE: PRT
<213> ORGANISM: Artificial Sequence
<220> FEATURE:
<223> OTHER INFORMATION: Human-adapted heavy chain variant HBV1

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20

Gly Glu Ile Asn Pro Asn Asn Gly Arg Ile Asn Gly Asn Glu Lys Phe
        50                  55                  60

Lys Thr Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Val Gly Val Met Ile Thr Thr Phe Pro Tyr Trp Gly Gln Gly
                100                 105                 110

Thr Leu Val Thr Val Ser Ser
            115

<210> SEQ ID NO 48
<211> LENGTH: 357
<212> TYPE: DNA
<213> ORGANISM: Artificial Sequence
<220> FEATURE:
<223> OTHER INFORMATION: Human-adapted heavy chain variant HBV2

<400> SEQUENCE: 48
caggtgcagc tggtgcagag cggcgcggaa gtgaaaaaac cgggcgcgag cgtgaaagtg      60
agctgcaaag cgagcggcta ccctttacc acctattgga ttcattgggt gcgccaggcg

-continued

```
<400> SEQUENCE: 50
caggtgcagc tggtgcagag cggcgcggaa gtgaaaaaac cgggcgcgag cgtgaaagtg      60
agctgcaaag cgagcggcta cctttacc acctattgga ttcattgggt gcgccaggcg     120
ccgggccagc gcctggaatg gatgggcgaa attaacccga caacggccg cattaactat     180 gcggaaaaat ttaaaacccg cgtgaccatt acccgcgata ccagcgcgag caccgcgtat     240
atggaactga gcagcctgcg cagcgaagat accgcggtgt attattgcgc gcgcgtgggc     300
gtgatgatta ccacctttcc gtattggggc cagggcaccc tggtgaccgt gagcagc      357

<210> SEQ ID NO 51
<211> LENGTH: 119
<212> TYPE: PRT
<213> ORGANISM: Artificial Sequence
<220> FEATURE:
<223> OTHER INFORMATION: Human-adapted heavy chain variant HBV4

<400> SEQUENCE: 51

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Thr Tyr
             20                  25                  30

Trp Ile His Trp Val Arg Gln Ala Pro Gly Gln

```
Gln Val Gln Leu Val Gln Ser Gly Ala Glu Val Lys Pro Gly Ala
 1               5                  10                  15

Ser Val Lys Val Ser Cys Lys Ala Ser Gly Tyr Thr Phe Thr Tyr
            20                  25                  30

Trp Ile His Trp Val Arg Gln Ala Pro Gly Gln Arg Leu Glu Trp Met
            35                  40                  45

Gly Glu Ile Asn Pro Asn Asn Gly Arg Ile Asn Tyr Asn Glu Lys Phe
 50                  55                  60

Lys Thr Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Gly Val Ile Ile Thr Thr Phe Pro Tyr Trp Gly Gln Gly
            100                 105                 110

Thr Leu Val Thr Val Ser Ser
            115
```

```
<210> SEQ ID NO 54
<211> LENGTH: 357
<212> TYPE: DNA
<213> ORGANISM: Artificial Sequence
<220> FEATURE:
<223> OTHER INFORMATION: Human-adapted heavy chain variant HBV5

<400> SEQUENCE: 54
caggtgcagc tggtgcagag cggcgcggaa gtgaaaaaac cgggcgcgag cgtgaaagtg     60
agctgcaaag cgagcggcta cctttacc acctattgga ttcattgggt gcgccaggcg      120
ccgggccagc gcctggaatg gatgggcgaa attaacccga caacggccg cattaactat     180 aacgaaaaat ttaaaacccg cgtgaccatt acccgcgata ccagcgcgag caccgcgtat    240
atggaactga gcagcctgcg cagcgaagat accgcggtgt attattgcgc gcgcgtgggc    300
gtgattatta ccacctttcc gtattggggc cagggcaccc tggtgaccgt gagcagc       357
```

```
<210> SEQ ID NO 55
<211> LENGTH: 107
<212> TYPE: PRT
<213> ORGANISM: Artificial Sequence
<220> FEATURE:
<223> OTHER INFORMATION: Human-adapted light chain variant HBV6

<400> SEQUENCE: 55

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile Ser Asn Tyr
            20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Phe Trp Ser Thr Pro Phe
                 85                  90                  95

Thr Phe Gly Gln Gly Thr Lys Leu Glu Ile Lys
            100                 105
```

```
<210> SEQ ID NO 56
<211> LENGTH: 321
```

```
<212> TYPE: DNA
<213> ORGANISM: Artificial Sequence
<220> FEATURE:
<223> OTHER INFORMATION: Human-adapted light chain variant HBV6

<400> SEQUENCE: 56
gatattcaga tgacccagag cccgagcagc ctgagcgcga gcgtgggcga tcgcgtgacc      60
attacctgcc gcgcgagcgg caacattagc aactatctgg cgtggtatca gcagaaaccg     120
ggcaaagcgc cgaaactgct gatttataac gcgaaaaccc tggcggatgg cgtgccgagc     180
cgctttagcg gcagcggcag cggcaccgat tttaccctga ccattagcag cctgcagccg     240
gaagattttg cgacctatta ttgccagcat ttttggagca ccccgtttac ctttggccag     300
ggcaccaaac tggaaattaa a                                               321

<210> SEQ ID NO 57
<211> LENGTH: 107
<212> TYPE: PRT
<213> ORGANISM: Artificial Sequence
<220> FEATURE:
<223> OTHER INFORMATION: Human-adapted light chain variant HBV7

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile Ser Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Leu Glu Ile Lys
            100                 105

<210> SEQ ID NO 58
<211> LENGTH: 321
<212> TYPE: DNA
<213> ORGANISM: Artificial Sequence
<220> FEATURE:
<223> OTHER INFORMATION: Human-adapted light chain variant HBV7

<400> SEQUENCE: 58
gatattcaga tgacccagag cccgagcagc ctgagcgcga gcgtgggcga tcgcgtgacc      60
attacctgcc gcgcgagcgg caacattagc agctatctgg cgtggtatca gcagaaaccg     120
ggcaaagcgc cgaaactgct gatttataac gcgaaaaccc tggcggatgg cgtgccgagc     180
cgctttagcg gcagcggcag cggcaccgat tttaccctga ccattagcag cctgcagccg     240
gaagattttg cgacctatta ttgccagcat ttttggagca ccccgtttac ctttggccag     300
ggcaccaaac tggaaattaa a                                               321

<210> SEQ ID NO 59
<211> LENGTH: 107
<212> TYPE: PRT
<213> ORGANISM: Artificial Sequence
<220> FEATURE:
<223> OTHER INFORMATION: Human-adapted light chain variant HBV8
```

```
<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Leu Glu Ile Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Human-adapted light chain variant HBV8

<400> SEQUENCE: 60
gatattcaga tgacccagag cccgagcagc ctgagcgcga gcgtgggcga tcgcgtgacc        60
attacctgcc gcgcgagcgg cggcattagc agctatctgg cgtggtatca gcagaaaccg       120
ggcaaagcgc cgaaactgct gatttataac gcgaaaaccc tggcggatgg cgtgccgagc       180
cgctttagcg gcagcggcag cggcaccgat tttaccctga ccattagcag cctgcagccg       240
gaagattttg cgacctatta ttgccagcat ttttggagca ccccgtttac ctttggccag       300
ggcaccaaac tggaaattaa a                                                 321

<210> SEQ ID NO 61
<211> LENGTH: 6
<212> TYPE: PRT
<213> ORGANISM: Artificial Sequence
<220> FEATURE:
<221> NAME/KEY: unsure
<222> LOCATION: (5)
<223> OTHER INFORMATION: Heavy chain CDR1 wherein Xaa at position 5 can
      be Isoleucine or
<220> FEATURE:
<223> OTHER INFORMATION: Methionine

<400> SEQUENCE: 61

Thr Thr Tyr Trp Xaa His
1               5

<210> SEQ ID NO 62
<211> LENGTH: 17
<212> TYPE: PRT
<213> ORGANISM: Artificial Sequence
<220> FEATURE:
<221> NAME/KEY: unsure
<222> LOCATION: (11)
<223> OTHER INFORMATION: Heavy chain CDR2 wherein Xaa at position 11 can
      be Tyrosine or
<220> FEATURE:
<223> OTHER INFORMATION: Glycine
<221> NAME/KEY: unsure
<222> LOCATION: (12)
<223> OTHER INFORMATION: Heavy chain CDR2 wherein Xaa at position 12 can
      be Asparagine or
<220> FEATURE:
```

```
<223> OTHER INFORMATION: Alanine
<221> NAME/KEY: unsure
<222> LOCATION: (15)
<223> OTHER INFORMATION: Heavy chain CDR2 wherein Xaa at position 15 can
      be Phenylalanine or
<220> FEATURE:
<223> OTHER INFORMATION: Glycine

<400> SEQUENCE: 62

Glu Ile Asn Pro Asn Asn Gly Arg Ile Asn Xaa Xaa Glu Lys Xaa Lys
 1               5                  10                  15

Thr

<210> SEQ ID NO 63
<211> LENGTH: 10
<212> TYPE: PRT
<213> ORGANISM: Artificial Sequence
<220> FEATURE:
<221> NAME/KEY: unsure
<222> LOCATION: (4)
<223> OTHER INFORMATION: Heavy chain CDR3 wherein Xaa at position 4 can
      be Methionine or
<220> FEATURE:
<223> OTHER INFORMATION: Isoleucine

<400> SEQUENCE: 63

Val Gly Val Xaa Ile Thr Thr Phe Pro Tyr
 1               5                  10
```